(12) United States Patent
Stapper et al.

(10) Patent No.: US 7,259,177 B2
(45) Date of Patent: Aug. 21, 2007

(54) CYCLOALKYLMETHOXY-SUBSTITUTED ACETIC ACID DERIVATIVES, PROCESSES FOR THEIR PREPARATION AND THEIR USE AS PHARMACEUTICALS

(75) Inventors: Christian Stapper, Mainz (DE); Stefanie Keil, Hofheim (DE); Heiner Glombik, Hofheim (DE); Eugen Falk, Frankfurt (DE); Jochen Goerlitzer, Frankfurt am Main (DE); Dirk Gretzke, Frankfurt (DE); Hans-Ludwig Schaefer, Hochheim (DE); Wolfgang Wendler, Selters (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 476 days.

(21) Appl. No.: 10/788,996

(22) Filed: Feb. 27, 2004

(65) Prior Publication Data

US 2005/0101637 A1    May 12, 2005

Related U.S. Application Data

(60) Provisional application No. 60/487,510, filed on Jul. 15, 2003.

(30) Foreign Application Priority Data

Feb. 27, 2003   (DE) ................................ 103 08 355

(51) Int. Cl.
*A61K 31/42*   (2006.01)
*C07D 263/30*  (2006.01)

(52) U.S. Cl. ........................... 514/374; 548/235
(58) Field of Classification Search ................ 514/374; 548/235
See application file for complete search history.

(56) References Cited

U.S. PATENT DOCUMENTS

| | | | |
|---|---|---|---|
| 6,221,633 B1 | 4/2001 | Ertl et al. | |
| 6,221,897 B1 | 4/2001 | Frick et al. | |
| 6,245,744 B1 | 6/2001 | Frick et al. | |
| 6,277,831 B1 | 8/2001 | Frick et al. | |
| 6,342,512 B1 | 1/2002 | Kirsch et al. | |
| 6,506,757 B1 * | 1/2003 | Tajima et al. | 514/254.02 |
| 7,148,246 B2 * | 12/2006 | Gretzke et al. | 514/374 |

FOREIGN PATENT DOCUMENTS

| EP | 1 067 109 A1 | 1/2001 |
|---|---|---|
| EP | 1 108 713 A1 | 6/2001 |
| EP | 0 462 884 A1 | 12/2001 |
| EP | 1 354 879 A1 | 10/2003 |
| WO | WO94/18183 | 8/1994 |
| WO | WO94/18184 | 8/1994 |
| WO | WO96/38428 | 12/1996 |
| WO | WO97/26265 | 7/1997 |
| WO | WO97/41097 | 11/1997 |
| WO | WO98/08871 | 3/1998 |
| WO | WO98/19998 | 5/1998 |
| WO | WO99/03861 | 1/1999 |
| WO | WO99/15525 | 4/1999 |
| WO | WO99/61431 | 12/1999 |
| WO | WO99/62871 | 12/1999 |
| WO | WO99/62872 | 12/1999 |
| WO | WO99/67278 | 12/1999 |
| WO | WO99/67279 | 12/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 A1 | 12/2000 |
| WO | WO 01/04146 A2 | 1/2001 |
| WO | WO 01/09111 A1 | 2/2001 |
| WO | WO 01/21602 A1 | 3/2001 |
| WO | WO 01/40169 A1 | 6/2001 |
| WO | WO 01/40171 A1 | 6/2001 |
| WO | WO 01/72290 A2 | 10/2001 |

(Continued)

OTHER PUBLICATIONS

Asakawa A et al., Cocaine-Amphetamine-Regulated Transcript Influences Energy Metabolism Anxiety and Gastric Emptying in Mice, Hormone and Metabolic Research; vol. 33(9); 2001; pp. 554-558.

(Continued)

*Primary Examiner*—Kamal A. Saeed
(74) *Attorney, Agent, or Firm*—Craig M. Bell

(57) ABSTRACT

Provided herein are novel compounds of formula I below:

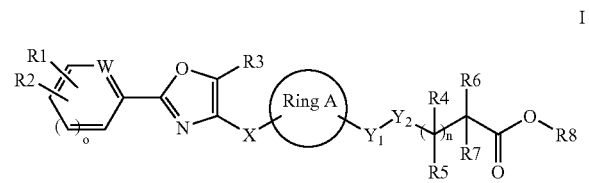

in which the radicals are as defined, their physiologically acceptable salts, processes for their preparation, as well as methods of treating and/or preventing disorders of disorders of fatty acid metabolism and glucose utilization disorders, and also of disorders in which insulin resistance is involved, in a patient.

10 Claims, No Drawings

FOREIGN PATENT DOCUMENTS

| | | |
|---|---|---|
| WO | WO 01/81327 A1 | 11/2001 |
| WO | WO 01/83451 A1 | 11/2001 |
| WO | WO 01/85695 A1 | 11/2001 |
| WO | WO 01/91752 A1 | 12/2001 |
| WO | WO 01/94300 A1 | 12/2001 |
| WO | WO 02/16331 A1 | 2/2002 |
| WO | WO 02/38541 A1 | 5/2002 |
| WO | WO 02/50027 | 6/2002 |
| WO | WO 02/051820 A1 | 7/2002 |
| WO | WO 02/096864 A1 | 12/2002 |
| WO | WO 03/020269 | 3/2003 |
| WO | WO 03/040174 A2 | 5/2003 |
| WO | WO 03/084922 | 10/2003 |
| WO | WO 03/084923 | 10/2003 |
| WO | WO 03/104188 | 12/2003 |

OTHER PUBLICATIONS

Berger Joel et al., The Mechanisms of Action of PPARs, Annul. Rev. Med.; vol. 53; 2002; pp. 409-435.

Fruchart Jean-Charles et al., PPARs, Metabolic Disease and Atherosclerosis, Pharmacological Research; vol. 44, No. 5; 2001; pp. 345-352.

Kersten Sander et al et al., Roles of PPARs in Health and Disease, Nature; vol. 405; May 25, 2000; pp. 421-424.

Kliewer Steven A et al., Peroxisome Proliferator-Activated Receptors: From Genes to Physiology, Recent Prog. Horm Res.; vol. 56; 2001; pp. 239-263.

Lee Daniel W et al., Leptin agonists as a potential approach to the treatment of obesity, Drugs of the Future; vol. 26(9); 2001; pp. 873-881.

Motojima Kiyoto, Peroxisome Proliferator-Activated Receptor (PPAR): Structure, Mechanisms of Activation and Diverse Functions, Cell Structure and Function; vol. 18; 1993; pp. 267-277.

Okada Hiroshi et al., Synthesis and Antitumor Activities of Prodrugs of Benzoylphenylureas, Chem. Pharm. Bull.; vol. 42(1); 1994; pp. 57-61.

Pineda Torra Ines et al., Peroxisome Proliferator-activated Receptors: from Transcriptional Control to Clinical Practice, Curr. Opin. Lipidol; vol. 12; 2001; pp. 245-254.

Pineda Torra Ines et al., Peroxisome proliferator-activated receptor alpha in metabolic disease, inflammation, atherosclerosis and aging, Curr. Opin. Lipidol; vol. 10; 1999; pp. 151-159.

Vidal-Puig A et al., Regulation of PPAR y Gene Expression by Nutrition and Obesity in Rodents, J. Clin. Invest.; vol. 97, No. 11, 1996; pp. 2553-2561.

Wilson Timothy M. et al., The PPARs: From Orphan Receptors to Drug Discovery, Journal of Medicinal Chemistry; vol. 43, No. 4; 2000; pp. 527-550.

Zunft H., J. F. et al., Carob Pulp Preparation for Treatment of Hypercholesterolemia, Advances in Natural Therapy; vol. 18, No. 5; Sep.-Oct. 2001; pp. 230-236.

* cited by examiner

CYCLOALKYLMETHOXY-SUBSTITUTED ACETIC ACID DERIVATIVES, PROCESSES FOR THEIR PREPARATION AND THEIR USE AS PHARMACEUTICALS

DOMESTIC PRIORITY CLAIM

This Application claims priority from U.S. Provisional Application No. 60/487,510 filed on Jul. 15, 2003.

PRIORITY CLAIM

This Application claims priority from German Application No. 10308355.3 filed on Feb. 27, 2003.

FIELD OF INVENTION

The invention relates to cycloalkylmethoxy-substituted acetic acid derivatives, processes for their preparation and to their use as pharmaceuticals, and to their physiologically acceptable salts and physiologically functional derivatives.

BACKGROUND OF THE INVENTION

Compounds of a similar structure have already been described in the prior art for the treatment of hyperlipidemia and diabetes (WO 2000/64876).

The citation of any reference herein should not be construed as an admission that such reference is available as "Prior Art" to the instant application.

SUMMARY OF THE INVENTION

The present invention extends to a compound having the formula I:

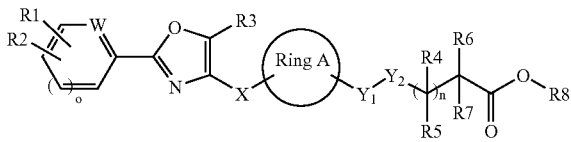

I in which:

Ring A is a $(C_3-C_8)$-cycloalkanediyl ring or a $(C_3-C_8)$-cycloalkenediyl ring,
wherein one or more carbon atoms of the $(C_3-C_8)$-cycloalkanediyl ring or the $(C_3-C_8)$-cycloalkenediyl ring may be replaced by oxygen atoms;

R1 and R2 are:
(a) Independently of one another H, F, Cl, Br, $CF_3$, $OCF_3$, $(C_1-C_6)$-alkyl, O—$(C_1-C_6)$-alkyl, $SCF_3$, $SF_5$, $OCF_2$—$CHF_2$, $(C_6-C_{10})$-aryl, $(C_6-C_{10})$-aryloxy, OH, $NO_2$; or
(b) together with the phenyl, pyridine, 1H-pyrrole, thiophene or furan ring form fused, partially or unsaturated bicyclic $(C_6-C_{10})$-aryl, $(C_5-C_{11})$-heteroaryl;

R3 is:
H, $(C_1-C_6)$-alkyl, $(C_3-C_8)$-cycloalkyl, $(C_1-C_3)$-alkyl-$(C_3-C_8)$-cycloalkyl, phenyl, $(C_1-C_3)$-alkyl-phenyl, $(C_5-C_6)$-heteroaryl, $(C_1-C_3)$-alkyl-$(C_5-C_6)$-heteroaryl, or $(C_1-C_3)$-alkyl fully or partially substituted by F;

W is:
(a) is CH or N if o=1, or
(b) is O, S or NR10 if o=0;

X is $(C_1-C_6)$-alkanediyl, wherein one or more carbon atoms of the $(C_1-C_6)$ alkanediyl may be replaced by oxygen atoms;
Y1 is $(CR13R14)_p$, wherein p is 1 or 2;
Y2 is CH2, O, S, SO, $SO_2$ or NR9;
n is 0-2;
R4 is H, $(C_1-C_6)$-alkyl; F if Y2 is not O; NR9
R5 is H, $(C_1-C_6)$-alkyl; F if Y2 is not O; NR9;
R6 is H, $(C_1-C_6)$-alkyl; or F if n is not 0;
R7 is:
H, F (if n is not 0), $(C_1-C_6)$-alkoxy, $(C_2-C_6)$-alkenyl, $(C_2-C_6)$-alkynyl, $(C_3-C_8)$-cycloalkyl, $(C_1-C_6)$-alkyl that may be unsubstituted or substituted by one or more radicals selected from the group consisting of:
hydroxyl, phenyl, $(C_5-C_{11})$-heteroaryl, $(C_1-C_6)$-alkoxy and NR11R12, or
phenyl that may be unsubstituted or substituted by one or more radicals from the group consisting of hydroxy, $(C_1-C_6)$-alkoxy, F and $CF_3$,
with the proviso that R7 is not NR11R12 or $(C_1-C_6)$-alkoxy if R6=F;
R6 and R7 are together with the carbon atom that carries them $(C_3-C_8)$-cycloalkyl;
R8 is H or $(C_1-C_6)$-alkyl;
R9 is:
H, $(C_1-C_6)$-alkyl, $(C_2-C_6)$-alkenyl, $(C_2-C_6)$-alkynyl, aryl-$(C_1-C_4)$-alkyl, CO—$(C_1-C_6)$-alkyl, CO—$(C_6-C_{10})$-aryl, CO—$(C_1-C_6)$-alkyl-$(C_6-C_{10})$-aryl, CO—$(C_5-C_{11})$-heteroaryl, C(O)—O—$(C_1-C_6)$-alkyl, C(O)—O—$(C_1-C_6)$-alkyl-$(C_6-C_{10})$-aryl, C(O)—O—$(C_6-C_{10})$-aryl, C(O)—O—$(C_5-C_{11})$-heteroaryl, $SO_2$—$(C_1-C_6)$-alkyl, $SO_2$—$(C_1-C_6)$-alkyl-$(C_6-C_{10})$-aryl, $SO_2$—$(C_1-C_6)$-alkyl-$SO_2$—$(C_1-C_6)$-alkyl, $SO_2$—$(C_6-C_{10})$-aryl, $SO_2$—$(C_5-C_{11})$-heteroaryl, wherein aryl or heteroaryl, or both may be unsubstituted or substituted by $(C_1-C_6)$-alkyl, O—$(C_1-C_6)$-alkyl, F, Cl, CO—$(C_1-C_6)$-alkyl;
R10 is H, $(C_1-C_6)$-alkyl or $(C_1-C_6)$-alkyl-phenyl;
R11 is H, $(C_1-C_6)$-alkyl or $(C_1-C_6)$-alkyl-phenyl;
R12 is H, $(C_1-C_6)$-alkyl or $(C_1-C_6)$-alkyl-phenyl;
R13 is H or $(C_1-C_6)$-alkyl; and
R14 is H or $(C_1-C_6)$-alkyl.

Furthermore, the present invention extends to a physiologically acceptable salt of a compound of the formula I as described above, to a solvate of a compound of the formula I as described above, and to a physiologically functional derivative of a compound of formula I as described above.

The present invention also extends to a compound of the formula I as described above, wherein:
Ring A is $(C_3-C_8)$-cycloalkanediyl or $(C_3-C_8)$-cycloalkenediyl, wherein one carbon atom of the $(C_3-C_8)$-cycloalkanediyl ring or the $(C_3-C_8)$ cycloalkenediyl ring may be replaced by an oxygen atom; and
X is $(C_1-C_6)$-alkanediyl, wherein the $C_1$ or $C_2$ carbon atom (to Ring A) may be replaced by an oxygen atom.

Naturally, the present invention extends to a physiologically acceptable salt of a compound of the formula I described above, a solvate of a compound of the formula I described above, and a physiologically functional derivative of a compound of the formula I described herein, wherein:
Ring A is $(C_3-C_8)$-cycloalkanediyl or $(C_3-C_8)$-cycloalkenediyl, wherein one carbon atom of the $(C_3-C_8)$-cycloalkanediyl ring or the $(C_3-C_8)$ cycloalkenediyl ring may be replaced by an oxygen atom; and
X is $(C_1-C_6)$-alkanediyl, wherein the $C_1$ or $C_2$ carbon atom (to Ring A) may be replaced by an oxygen atom.

The present invention further extends to a compound of formula I as described above, in which one or more radicals of the compound are as defined follows:
Ring A is a cyclohexane-1,3-diyl;
R1 is F, Br, $CF_3$, $OCF_3$, $(C_1-C_6)$-alkyl, O—$(C_1-C_6)$-alkyl, or phenyl;
R1 and R2 together with a phenyl ring of the compound form a naphthyl;
R1 is in the meta- or in the para-position;
R2 is hydrogen;
R3 is H, $(C_1-C_6)$-alkyl, $(C_3-C_8)$-cycloalkyl, $(C_1-C_3)$-alkyl-$(C_5-C_6)$-cycloalkyl, phenyl, or $(C_1-C_3)$-alkyl-phenyl;
W is CH if o=1;
X is $CH_2$—O or $CH_2$—O—$CH_2$;
n is 0;
R6 is H or $(C_1-C_6)$-alkyl;
R6 and R7 together with the carbon atom that carries them are $(C_3-C_6)$-cycloalkyl, and in particular a cyclopentyl; or
R7 is $(C_1-C_6)$-alkyl unsubstituted or substituted by one or more radicals selected from the group consisting of hydroxyl, phenyl, $(C_5-C_{11})$-heteroaryl, $(C_1-C_6)$-alkoxy and NR11R12, wherein:
R11 and R12 are H, or $(C_1-C_6)$-alkyl; or
R13 and R14 are hydrogen.

In addition, the present invention extends to a physiologically acceptable salt of a compound of the formula I described above, a solvate of a compound of the formula I described above, and a physiologically functional derivative of a compound of the formula I described above, wherein one or more radicals of the compound are as defined follows:
Ring A is a cyclohexane-1,3-diyl;
R1 is F, Br, $CF_3$, $OCF_3$, $(C_1-C_6)$-alkyl, O—$(C_1-C_6)$-alkyl, or phenyl;
R1 and R2 together with a phenyl ring of the compound form a naphthyl;
R1 is in the meta- or in the para-position;
R2 is hydrogen;
R3 is H, $(C_1-C_6)$-alkyl, $(C_3-C_8)$-cycloalkyl, $(C_1-C_3)$-alkyl-$(C_5-C_6)$-cycloalkyl, phenyl, or $(C_1-C_3)$-alkyl-phenyl;
W is CH if o=1;
X is $CH_2$—O or $CH_2$—O—$CH_2$;
n is 0;
R6 is H or $(C_1-C_6)$-alkyl;
R6 and R7 together with the carbon atom that carries them are $(C_3-C_6)$-cycloalkyl, and in particular a cyclopentyl; or
R7 is $(C_1-C_6)$-alkyl unsubstituted or substituted by one or more radicals selected from the group consisting of hydroxyl, phenyl, $(C_5-C_{11})$-heteroaryl, $(C_1-C_6)$-alkoxy and NR11R12, wherein:
R11 and R12 are H, or (C1-C6)-alkyl; or
R13 and R14 are hydrogen.

The present invention further extends to a compound of formula I as described herein, wherein R7 is $(C_1-C_4)$-alkyl, $(C_1-C_4)$-alkyl-O—$(C_1-C_4)$-alkyl or benzyl.

Moreover, the present invention extends to a physiologically acceptable salt of a compound of the formula I as described above, a solvate of a compound of the formula I described above, and a physiologically functional derivative of a compound of the formula I described above, in which R7 is $(C_1-C_4)$-alkyl, $(C_1-C_4)$-alkyl-O—$(C_1-C_4)$-alkyl or benzyl.

In a particular embodiment, the present invention extends to a compound of the formula I as described above, as well as a physiologically acceptable salt of the compound, a solvate of the compound, and a physiologically acceptable derivative of the compound, wherein R7 is $(C_1-C_4)$-alkyl or benzyl.

Furthermore, the present invention extends to a compound of the formula I as described above, in which
Ring A is cis-cyclohexane-1,3-diyl;
R1 and R2 are:
independently of one another H, F, $CF_3$, $(C_1-C_6)$-alkyl, O—$(C_1-C_6)$-alkyl, or phenyl; or
together with a phenyl ring of the compound form a naphthyl;
R3 is $(C_1-C_6)$-alkyl, $(C_3-C_8)$-cycloalkyl, or phenyl;
W is:
CH if o=1, or
O or S if o=0;
X is $CH_2$—O or $CH_2$—O—$CH_2$;
Y1 is $CH_2$;
Y2 is $CH_2$, O, S, SO, $SO_2$ or NR9;
n is 0;
R4 is H;
R5 is H;
R6 is H, $(C_1-C_6)$-alkyl, or benzyl;
R7 is H, $(C_1-C_6)$-alkyl, $(C_3-C_6)$-cycloalkyl, phenyl, or benzyl,
R6 and R7 together with the carbon atom that carries them are $(C_3-C_6)$-cycloalkyl;
R8 is H; and
R9 is:
H, or
$(C_1-C_6)$-alkyl, which may be unsubstituted or substituted by:
$(C_3-C_6)$-cycloalkyl, phenyl, $(C_5-C_6)$-heteroaryl; CO—$(C_1-C_6)$-alkyl, CO—$(C_1-C_6)$-alkyl-phenyl, CO-phenyl, C(O)—O—$(C_1-C_6)$-alkyl, CO—NH-phenyl, $SO_2$—$(C_1-C_4)$-alkyl, $SO_2$—$(C_1-C_4)$-alkyl-$SO_2$—$(C_1-C_4)$-alkyl, $SO_2$-tolyl, or a combination thereof, wherein the phenyl of the substituent for its part may be substituted by O—$(C_1-C_3)$-alkyl.

Naturally, the present invention extends to a physiologically acceptable salt, a solvate and a physiologically functional derivative of a compound of the formula I described above, in which
Ring A is cis-cyclohexane-1,3-diyl;
R1 and R2 are:
independently of one another H, F, $CF_3$, $(C_1-C_6)$-alkyl, O—$(C_1-C_6)$-alkyl, or phenyl; or
R1 and R2 together with a phenyl ring of the compound form a naphthyl;
R3 is $(C_1-C_6)$-alkyl, $(C_3-C_8)$-cycloalkyl, or phenyl;
W is:
CH if o=1, or
O or S if o=0;
X is $CH_2$—O or $CH_2$—O—$CH_2$;
Y1 is $CH_2$;
Y2 is $CH_2$, O, S, SO, $SO_2$ or NR9;
n is 0;
R4 is H;
R5 is H;
R6 is H, $(C_1-C_6)$-alkyl, or benzyl;
R7 is H, $(C_1-C_6)$-alkyl, $(C_3-C_6)$-cycloalkyl, phenyl, or benzyl,
R6 and R7 together with the carbon atom that carries them are $(C_3-C_6)$-cycloalkyl;
R8 is H; and
R9 is:
H, or
$(C_1-C_6)$-alkyl, which may be unsubstituted or substituted by:

($C_3$-$C_6$)-cycloalkyl, phenyl, ($C_5$-$C_6$)-heteroaryl; CO—($C_1$-$C_6$)-alkyl, CO—($C_1$-$C_6$)-alkyl-phenyl, CO-phenyl, C(O)—O—($C_1$-$C_6$)-alkyl, CO—NH-phenyl, $SO_2$—($C_1$-$C_4$)-alkyl, $SO_2$—($C_1$-$C_4$)-alkyl-$SO_2$—($C_1$-$C_4$)-alkyl, $SO_2$-tolyl, or a combination thereof, wherein the phenyl of the substituent for its part may be substituted by O—($C_1$-$C_3$)-alkyl.

Furthermore, the present invention extends to a compound as described above, as well as to a physiological salt of the compound, a solvate of the compound, or a physiologically functional derivative of the compound, wherein the alkyl radicals in the substituents R1, R2, R3, R4, R5, R6, R7, R8, R9, R10, R11, R12, R13 and R14 of the compound may be either straight-chain or branched.

Furthermore, the present invention extends to a pharmaceutical composition comprising a compound of formula I as described above and a pharmaceutically acceptable carrier. Also encompassed by the present invention is a pharmaceutical composition comprising a physiologically acceptable salt of a compound of formula I described above, a solvate of a compound of formula I described above, or a physiologically functional derivative of a compound of formula I described above, and a pharmaceutically acceptable carrier.

In another embodiment, the present invention extends to a method of treating and/or preventing a disorder or condition in a patient comprising administering a therapeutically effective amount of a compound of formula I described above, a physiologically effective salt of a compound of formula I described above, a solvate of a compound of formula I described above, or a physiologically acceptable derivative of a compound of formula I described above, to the patient. Particular examples of disorders and conditions that can be treated and/or prevented with the administration of a compound of the present invention are described infra.

The present invention further extends to a method for treating and/or preventing a disorder of fatty acid metabolism or glucose utilization in a patient, comprising administering a therapeutically effective amount of a compound of the formula I described above.

Moreover, the present invention extends to a method for treating and/or preventing a disorder involving insulin resistance in a patient, comprising administering a therapeutically effective amount of a compound of the formula I above to the patient.

The present invention also extends to a method for treating and/or preventing diabetes mellitus and its sequelae in a patient, comprising administering a therapeutically effective amount of a compound of the formula I to the patient.

In another emobidment, the present invention extends to a method for treating and/or preventing dyslpidemias and their sequelae in a patient, comprising administering a therapeutically effective amount of a compound of formula I above to the patient.

Similarly, the present invention extends to a method for treating and/or preventing a physiological state associated with a metabolic syndrome in a patient, comprising administering a therapeutically effective amount of a compound of formula I to the patient.

Furthermore, the present invention extends to a for treating a patient as described above, wherein a therapeutically effective amount of a second active compound for treating and/or preventing the particular disorder or condition is administered.

Accordingly, It is an aspect of the present invention to provide compounds that permit a therapeutically exploitable modulation of the lipid and/or carbohydrate metabolism and are thus suitable for the prevention and/or treatment of disorders such as type 2 diabetes and atherosclerosis and their multifarious sequelae.

This and other aspects of the present invention will be better appreciated by reference to the following Detailed Description.

DETAILED DESCRIPTION OF THE INVENTION

The present invention is based upon the discovery of heretofore unknown compounds that surprisingly and unexpectedly, are modulators of the activity of peroxisome proliferator-activated receptors (PPARs). PPARs are transcription factors which can be activated by ligands and belong to the class of nuclear hormone receptors. There are three PPAR isoforms, PPARalpha, PPARgamma and PPAR-delta, which are encoded by different genes (Peroxisome proliferator-activated receptor (PPAR): structure, mechanisms of activation and diverse functions: Motojima K, Cell Struct Funct. 1993 October; 18(5): 267-77).

Two variants of PPARgamma exist, PPARgamma$_1$ and gamma$_2$, which are the result of alternative use of promoters and differential mRNA splicing (Vidal-Puig et al. J. Clin. Invest., 97:2553-2561,1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

Broadly, the present invention extends to a compound having the formula I:

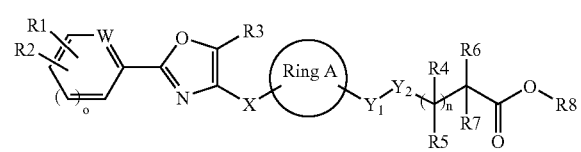

in which:

Ring A is a ($C_3$-$C_8$)-cycloalkanediyl ring or a ($C_3$-$C_8$)-cycloalkenediyl ring, wherein one or more carbon atoms of the ($C_3$-$C_8$)-cycloalkanediyl ring or the ($C_3$-$C_8$)-cycloalkenediyl ring may be replaced by oxygen atoms;

R1 and R2 are:

(a) Independently of one another H, F, Cl, Br, $CF_3$, $OCF_3$, ($C_1$-$C_6$)-alkyl, O—($C_1$-$C_6$)-alkyl, $SCF_3$, $SF_5$, $OCF_2$—$CHF_2$, ($C_6$-$C_{10}$)-aryl, ($C_6$-$C_{10}$)-aryloxy, OH, $NO_2$; or (b) together with the phenyl, pyridine, 1H-pyrrole, thiophene or furan ring form fused, partially or unsaturated bicyclic ($C_6$-$C_{10}$)-aryl, ($C_5$-$C_{11}$)-heteroaryl;

R3 is:

H, ($C_1$-$C_6$)-alkyl, ($C_3$-$C_8$)-cycloalkyl, ($C_1$-$C_3$)-alkyl-($C_3$-$C_8$)-cycloalkyl, phenyl, ($C_1$-$C_3$)-alkyl-phenyl, ($C_5$-$C_6$)-heteroaryl, ($C_1$-$C_3$)-alkyl-($C_5$-$C_6$)-heteroaryl, or ($C_1$-$C_3$)-alkyl fully or partially substituted by F;

W is:

(a) is CH or N if o=1, or (b) is O, S or NR10 if o=0;

X is ($C_1$-$C_6$)-alkanediyl, wherein one or more carbon atoms of the ($C_1$-$C_6$) alkanediyl may be replaced by oxygen atoms;

Y1 is $(CR13R14)_p$, wherein p is 1 or 2;

Y2 is CH2, O, S, SO, $SO_2$ or NR9;

n is 0-2;

R4 is H, ($C_1$-$C_6$)-alkyl, NR9, or F if Y2 is not O;

R5 is H, ($C_1$-$C_6$)-alkyl, NR9, or F if Y2 is not O;

R6 is H, ($C_1$-$C_6$)-alkyl; or F if n is not 0;

R7 is:

H, F (if n is not 0), ($C_1$-$C_6$)-alkoxy, ($C_2$-$C_6$)-alkenyl, ($C_2$-$C_6$)-alkynyl, ($C_3$-$C_8$)-cycloalkyl, ($C_1$-$C_6$)-alkyl that may be unsubstituted or substituted by one or more radicals selected from the group consisting of:

hydroxyl, phenyl, ($C_5$-$C_{11}$)-heteroaryl, ($C_1$-$C_6$)-alkoxy and NR11R12, or phenyl that may be unsubstituted or substituted by one or more radicals from the group consisting of hydroxy, ($C_1$-$C_6$)-alkoxy, F and $CF_3$, with the proviso that R7 is not NR11R12 or ($C_1$-$C_6$)-alkoxy if R6=F;

R6 and R7 are together with the carbon atom that carries them ($C_3$-$C_8$)-cycloalkyl;

R8 is H or ($C_1$-$C_6$)-alkyl;

R9 is:

H, ($C_1$-$C_6$)-alkyl, ($C_2$-$C_6$)-alkenyl, ($C_2$-$C_6$)-alkynyl, aryl-($C_1$-$C_4$)-alkyl, CO—($C_1$-$C_6$)-alkyl, CO—($C_6$-$C_{10}$)-aryl, CO—($C_1$-$C_6$)-alkyl-($C_6$-$C_{10}$)-aryl, CO—($C_5$-$C_{11}$)-heteroaryl, C(O)—O—($C_1$-$C_6$)-alkyl, C(O)—O—($C_1$-$C_6$)-alkyl-($C_6$-$C_{10}$)-aryl, C(O)—O—($C_6$-$C_{10}$)-aryl, C(O)—O—($C_5$-$C_{11}$)-heteroaryl, $SO_2$—($C_1$-$C_6$)-alkyl, $SO_2$—($C_1$-$C_6$)-alkyl; ($C_6$-$C_{10}$)-aryl, $SO_2$—($C_1$-$C_6$)-alkyl-$SO_2$—($C_1$-$C_6$)-alkyl, $SO_2$—($C_6$-$C_{10}$)-aryl $SO_2$—($C_5$-$C_{11}$)-heteroaryl, wherein aryl or heteroaryl, or both may be unsubstituted or substituted by ($C_1$-$C_6$)-alkyl, O—($C_1$-$C_6$)-alkyl, F, Cl, CO—($C_1$-$C_6$)-alkyl;

R10 is H, ($C_1$-$C_6$)-alkyl or ($C_1$-$C_6$)-alkyl-phenyl;

R11 is H, ($C_1$-$C_6$)-alkyl or ($C_1$-$C_6$)-alkyl-phenyl;

R12 is H, ($C_1$-$C_6$)-alkyl or ($C_1$-$C_6$)-alkyl-phenyl;

R13 is H or ($C_1$-$C_6$)-alkyl; and

R14 is H or ($C_1$-$C_6$)-alkyl;

a physioloigically acceptable salt of the compound;

a solvate of the compound, or a physiologically active derivative of the compound.

Numerous terms and phrases are used throughout the instant specification and claims. Accordingly:

As used herein, "aryl" refers an aromatic carbocyclic mono- or bicyclic ring system which comprises 6 to 10 atoms in the ring or rings.

As used herein, "heteroaryl" refers to a mono- or bicyclic aromatic ring system having 4 to 11 ring members, in which at least one atom in the ring system is a heteroatom from the series N, O and S.

As used herein, the term "a" refers to one or more than one.

In addition, a compound of the formula I described above (also referred to as a compound of the present invention or a compound of the invention) comprises at least two centers of asymmetry and may comprise more in addition. Thus, a compound of the present invention may exist in the form of its racemate, as a racemic mixture, as a pure enantiomer, a diastereomer or as a mixture of diastereomers. The present invention encompasses all these isomeric forms of a compound of the formula I.

These isomeric forms can be obtained by known methods using routine laboratory techniques, even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of a compound of the present invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

As used herein, the term "physiologically functional derivative" refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of a compound of the present invention, as described, for example, in H. Okada et al., Chem. Pharm. Bull. 1994, 42, 57-61. Such prodrugs can be metabolized in vivo to a compound of the invention. These prodrugs may themselves be active or not.

A compound of the present invention may also exist in various polymorphous forms, for example as amorphous and crystalline polymorphous forms. All polymorphous forms of a compound of the present invention belong within the framework of the present invention and are a further aspect of the present invention.

All references to "compound(s) of formula I" hereinafter refer to compound(s) of the formula I as described above, and their salts, solvates and physiologically functional derivatives as described herein.

Formulations

As explained above, the present invention extends to a pharmaceutical composition comprising a compound of the present invention and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human. In particular, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient.

These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Methods for Treating and/or Preventing Disease or Condition

This invention relates further to the use of compounds of the formula I and their pharmaceutical compositions as PPAR ligands. The PPAR ligands of the invention are suitable as modulators of PPAR activity. As explained above, PPARs are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct. 1993 October; 18(5): 267-77).

Two variants of PPARgamma exist, PPARgamma$_1$ and gamma$_2$, which are the result of alternative use of promoters and differential mRNA splicing (Vidal-Puig et al. J. Clin. Invest., 97:2553-2561,1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

The present invention relates to compounds of the formula I suitable for modulating the activity of PPARs, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu.

Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 345-52; 2001; Sander Kersten, Beatrice Desvergne & Walter Wahli: Roles of PPARs in health and disease, NATURE, VOL 405, 25 MAY 2000; 421-4; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Thus, the present invention extends to a method of treating and/or preventing a disease or condition in a patient, comprising administering a therapeutically effective amount of a compound of formula I to the patient.

As used herein, the phrase "therapeutically effective amount" is used herein to mean an amount sufficient to cause an improvement in a clinically significant condition in the patient or even prevent a disease, disorder or condition in a patient. The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of a disease or condition set forth below, a compound of formula I may be used as the compound itself, but they are preferably in the form of a pharmaceutical composition with a pharmaceutically acceptable carrier.

Numerous diseases, disorders or conditions can be treated or prevented with a method of the present invention. Particular examples include, but certainly are not limited to:

1. disorders of fatty acid metabolism and glucose utilization disorders
   disorders in which insulin resistance is involved
2. Diabetes mellitus, especially type 2 diabetes, including the prevention of the sequelae associated therewith. Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Other disorders or conditions in which inflammatory reactions or cell differentiation may for example be involved are:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   pancreatitis
   other inflammatory states
   retinopathy
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc acute and chronic myeloproliferative disorders and lymphomas
angiogenesis
neurodegenerative disorders
Alzheimer's disease
multiple sclerosis
Parkinson's disease
erythematoi-squamous dermatoses such as, for example, psoriasis
acne vulgaris
other skin disorders and dermatological conditions which are modulated by PPAR
eczemas and neurodermitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal papillomata, viral warts such as, for example, molluscum contagiosum, leukoplakia
papular dermatoses such as, for example, Lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

COMBINATIONS WITH OTHER MEDICAMENTS

In a method of the present invention for treating and/or preventing a disease, disorder, or condition in a patient, a compound of the formula I can be administered alone or in combination with one or more further pharmacologically active substances which have, for example, favorable effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
They can be combined with a compound of the formula I in particular for a synergistic improvement in the effect.

Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantuso® (see www-.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the present invention, a compound of the formula I is administered in combination with insulin.

In one embodiment of the present invention, a compound of the formula I is administered in combination with substances which influence hepatic glucose production such as, for example, glycogen phosphorylase inhibitors (see: WO 01/94300, WO 02/096864, WO 03/084923, WO 03/084922, WO 03/104188).

In one embodiment of the present invention, a compound of the formula I is administered in combination with a sulfonylurea such as, for example, tolbutamide, glibenclamide, glipizide or glimepiride.

In one embodiment of the present invention, a compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the present invention, a compound of the formula I is administered in combination with a biguanide such as, for example, metformin.

In a further embodiment of the present invention, a compound of the formula I is administered in combination with a meglitinide such as, for example, repaglinide.

In one embodiment of the present invention, a compound of the formula I is administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the present invention, a compound of the formula I is administered in combination with a DPPIV inhibitor as described, for example, In WO98/19998, WO99/61431, WO99/67278, WO99/67279, WO01/72290, WO 02/38541, WO03/040174, in particular P 93/01 (1-cy-clopentyl-3-methyl-1-oxo-2-pentanammonium chloride), P-31/98, LAF237 (1-[2-[3-hydroxyadamant-1-ylamino) acetyl]pyrrolidine-2-(S)-carbonitrile), TS021 ((2S, 4S)-4-fluoro-1-[[(2-hydroxy-1,1-dimethylethyl)amino]-acetyl] pyrrolidine-2-carbonitrile monobenzenesulfonate).

In one embodiment of the present invention, a compound of the formula I is administered in combination with a PPARgamma agonist such as, for example, rosiglitazone, pioglitazone.

In one embodiment of the present invention, a compound of the formula I is administered in combination with compounds with an inhibitory effect on SGLT-1 and/or 2, as disclosed directly or indirectly for example in PCT/EP03/06841, PCT/EP03/13454 and PCT/EP03/13455.

In one embodiment of the present invention, a compound of the formula I is administered in combination with an α-glucosidase inhibitor such as, for example, miglitol or acarbose.

In one embodiment of the present invention, a compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the present invention, a compound of the formula I is administered in combination with an HMGCoA reductase inhibitor such as lovastatin, fluvastatin, pravastatin, simvastatin, ivastatin, itavastatin, atorvastatin, rosuvastatin.

In one embodiment of the present invention, a compound of the formula I is administered in combination with a bile acid reabsorption inhibitor (see, for example, U.S. Pat. Nos. 6,245,744, 6,221,897, 6,277,831, EP 0683 773, EP 0683 774).

In one embodiment of the present invention, a compound of the formula I is administered in combination with a polymeric bile acid adsorbent such as, for example, cholestyramine, colesevelam.

In one embodiment of the present invention, a compound of the formula I is administered in combination with a cholesterol absorption inhibitor as described for example in WO 0250027, or ezetimibe, tiqueside, pamaqueside.

In one embodiment of the present invention, a compound of the formula I is administered in combination with an LDL receptor inducer (see, for example, U.S. Pat. No. 6,342,512).

In one embodiment of the present invention, a compound of the formula I is administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Hoechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the present invention, a compound of the formula I is administered in combination with a PPARalpha agonist.

In one embodiment of the present invention, a compound of the formula I is administered in combination with a mixed PPAR alpha/gamma agonist such as, for example, AZ 242 (Tesaglitazar, (S)-3-(4-[2-(4-methanesulfonyloxyphenyl) ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the present invention, a compound of the formula I is administered in combination with a fibrate such as, for example, fenofibrate, gemfibrozil, clofibrate, bezafibrate.

In one embodiment of the present invention, a compound of the formula I is administered in combination with nicotinic acid or niacin.

In one embodiment of the present invention, a compound of the formula I is administered in combination with a CETP inhibitor, e.g. CP-529, 414 (torcetrapib).

In one embodiment of the present invention, a compound of the formula I is administered in combination with an ACAT inhibitor.

In one embodiment of the present invention, a compound of the formula I is administered in combination with an MTP inhibitor such as, for example, implitapide.

In one embodiment of the present invention, a compound of the formula I is administered in combination with an antioxidant.

In one embodiment of the present invention, a compound of the formula I is administered in combination with a lipoprotein lipase inhibitor.

In one embodiment of the present invention, a compound of the formula I is administered in combination with an ATP citrate lyase inhibitor.

In one embodiment of the present invention, a compound of the formula I is administered in combination with a squalene synthetase inhibitor.

In one embodiment of the present invention, a compound of the formula I is administered in combination with a lipoprotein(a) antagonist.

Antiobesity Agents

In another embodiment of the invention, a compound of the formula I is administered in combination with a lipase inhibitor such as, for example, orlistat.

In one embodiment of the present invention, the further active ingredient is fenfluramine or dexfenfluramine.

In another embodiment of the present invention, the further active ingredient is sibutramine.

In a further embodiment, a compound of the formula I is administered in combination CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro- 3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the present invention, the further active ingredient is leptin.

In one embodiment of the present invention, the further active ingredient is dexamphetamine, amphetamine, mazindole or phentermine.

In one embodiment of the present invention, a compound of the formula I is administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment of the present invention, a compound of the formula I is administered in combination with medicaments having an antiinflammatory effect.

In one embodiment of the present invention, a compound of the formula I is administered in combination with medicaments which are employed for cancer therapy and cancer prevention.

It will be appreciated that every suitable combination of a compound of the present invention with one or more of the aforementioned compounds and optionally one or more other pharmacologically active substances is regarded as falling within the protection conferred by the present invention.

The present invention may be better understood by reference to the following non-limiting Examples, which are provided as exemplary of the invention. The following Examples are presented in order to more fully illustrate the particular embodiments of the present invention. They should in no way be construed, however, as limiting the broad scope of the invention.

Assays (A) Determination of EC50 Values of PPAR Agonists in the Cellular PPARalpha Assay Principle The potency of substances that bind to human PPARα and activate in an agonistic manner is analyzed using a stably transfected HEK cell line (HEK=human embryo kidney) which is referred to here as PPARalpha reporter cell line. It contains two genetic elements, a luciferase reporter element (pΔM-GAL4-Luc-Zeo) and a PPARalpha fusion protein (GR-GAL4-humanPPARα-LBD) that mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is integrated in the genome of the cell line. There is only little expression of the luciferase reporter gene without addition of a PPARalpha ligand if fatty acid-depleted fetal calf serum (cs-FCS) is used in the assay. PPARα ligands bind and activate the PPARα fusion protein and thereby bring about expression of the luciferase reporter gene. The luciferase which is formed can be detected by means of chemiluminescence via an appropriate substrate.

Construction of the Cell Line

The PPARalpha reporter cell line was prepared in 2 stages. Firstly, the luciferase reporter element was constructed and stably transfected into HEK cells. For this purpose, five binding sites of the yeast transcription factor GAL4 (each 5'-CGGAGTACTGTCCTCCGAG-3' (SEQ ID NO:1)) were cloned in 5'-upstream of a 68 bp-long minimal MMTV promoter (Genbank Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete Photinus pyralis gene (Genbank Accession # M15077) was cloned in 3'-downstream of the GAL4-MMTV element. After sequencing, the luceriferase reporter element consisting of five GAL4 binding sites, MMTV promoter and luciferase gene was recloned into a plasmid which confers zeocin resistance in order to obtain the plasmid pΔM-GAL4-Luc-Zeo. This vector was transfected into HEK cells in accordance with the statements in Ausubel, F. M. et al. (Current protocols in molecular biology, Vol.1-3, John Wiley & Sons, Inc., 1995). Then zeocin-containing medium (0.5 mg/ml) was used to select a suitable stable cell clone that showed very low basal expression of the luceriferase gene. In a second step, the PPARalpha fusion protein (GR-GAL4-humanPPARalpha-LBD) was introduced into the stable cell clone described. For this purpose, initially the cDNA coding for the N-terminal 76 amino acids of the glucocorticoid receptor (Genbank Accession # P04150) was linked to the cDNA section coding for amino acids 1-147 of the yeast transcription factor GAL4 (Genbank Accession # P04386). The cDNA of the ligand-binding domain of the human PPARalpha receptor (amino acids S167-Y468; Genbank Accession # S74349) was cloned in at the 3'-end of this GR-GAL4 construct. The fusion construct prepared in this way (GR-GAL4-humanPPARalpha-LBD) was recloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line that contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay described below:

Day 1

The PPARα reporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin).

Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% CO2 for 24 h.

Day 3

The PPARα reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

The PPARalpha EC50 values for the compounds of Examples 1 to 85 in this assay are in the range from 0.07 nm to >10 µM.

The results for the activity of some compounds of the invention of the formula I are indicated in Table I below:

TABLE 1

| Example No. | EC50 PPARalpha [nM] |
|---|---|
| 4 | 25 |
| 8a | 1.8 |
| 9 | 4.3 |
| 16 | 4.0 |
| 22 | 0.07 |
| 24 | 0.3 |
| 33 | 17 |
| 38 | 8.5 |
| 42 | 79 |
| 51 | 12 |
| 64 | 0.4 |
| 74 | 0.4 |

It is evident from Table I that the compounds of the invention of the formula I active the PPARalpha receptor and thus bring about for example in Analogy to fibrates in clinical use a lowering of triglycerides in the body (see, for example, J.-Ch. Fruchard et al.: PPARS, Metabolic Disease and Atherosclerosis, Pharmacological Research, Vol. 44, No. 5, 345-52, 2001; S. Kersten et al.: Roles of PPARs in health and disease, NATURE, VOL 405, 25 MAY 2000, 421-4; I. Pineda et al.: Peroxisome proliferator-activated receptors: from transcriptional control to clinical practice, Curr Opin Lipidol 12:2001, 245-254).

(B) Determination of EC50 Values of PPAR Agonists in the Cellular PPARgamma Assay Principle A transient transfection system is employed to determine the cellular PPARgamma activity of PPAR agonists. It is based on the use of a luciferase reporter plasmid (pGL3basic-5xGAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARγ assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5xGAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3' (SEQ ID NO:2)), together with a 160 bp-long thymidine kinase promoter section (Genbank Accession # AF027128) 5'-upstream into pGL3basic. 3'-downstream of the thymidine kinase promoter is the complete luciferase gene from Photi nus pyralis (Genbank Accession # M15077), which is already a constituent of the plasmid pGL3basic used. The cloning and sequencing of the reporter plasmid pGL3basic-5xGAL4-TK took place in analogy to the description in Sambrook J. et. al. (Molecular cloning, Cold Spring Harbor Laboratory Press, 1989).

The PPARgamma expression plasmid pcDNA3-GAL4-humanPPARγLBD was prepared by first cloning the cDNA coding for amino acids 1-147 of the yeast transcription factor GAL4 (Genbank Accession # P04386) into the plasmid pcDNA3 (from Invitrogen) 3'-downstream of the cytomegalovirus promoter. Subsequently, the cDNA of the ligand-binding domain (LBD) of the human PPARγ receptor (amino acids I152-Y475; Accession # g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5xGAL4-TK and the PPARγ expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (# 41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM, is prepared. The following amounts are used to make up 3 ml of solution A for each 96 well microtiter plate for an assay: 2622 µl of antibiotic- and serum-free DMEM (# 41965-039, Invitrogen), 100 µl of reference plasmid pRL-CMV (1 ng/µl), 100 µl of luciferase reporter plasmid pGL3basic-5xGAL4-TK (10 ng/µl), 100 µl of PPARγ expression plasmid pcDNA3-GAL4-humanPPARγLBD (100 ng/µl) and 78 µl of plasmid pBluescript SK(+) (500 ng/µl). Then 2 ml of solution B are prepared by mixing 1.9 ml of DMEM (# 41965-039, Invitrogen) with 100 µl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min.

80%-confluent HEK cells from a cell culture bottle with a capacity of 175 cm$^2$ are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (# 41965-039, Invitrogen), which is mixed with 10% FCS (# 16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 µp of the suspension are seeded in each well of a 96 well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM (# 41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 µM to 100 pM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. Each plate is charged with a standard PPARγ agonist, which is likewise diluted in 11 different concentrations, in order to demonstrate the functioning of the assay in each individual plate. The assay plates are incubated in an incubator at 37° C. and 5% $CO_2$.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (Photinus pyralis) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid pRL-CMV. After incubation at room temperature in the dark for a further 10 minutes, a chemiluminescence mediated by the Renilla luciferase is again measured for 1 sec/well in the measuring instrument.

Evaluation

The crude data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS).

PPARgamma EC50 values in the range from 0.08 nM to >10 µM were measured for the PPAR agonists described in this application.

As explained above, the examples below serve to illustrate the invention, but without limiting it.

TABLE II

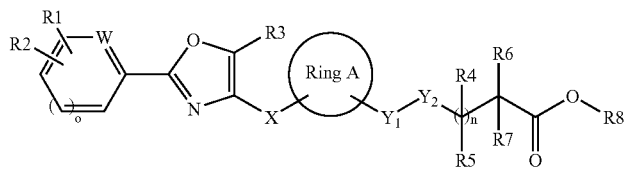

Herein below:
Ring A = cis-cyclohexane-1,3-diyl, R4 = R5 = H and R8 = H.

| Ex. | R1 | R2 | R3 | W | X | Y1 | Y2 | n | R6 | R7 | R9 |
|---|---|---|---|---|---|---|---|---|---|---|---|
| 1 | p-CH3 | H | CH3 | CH | CH2O | CH2 | O | 0 | H | n-C3H7 | — |
| 2 | p-CH3 | H | CH3 | CH | CH2O | CH2 | O | 0 | H | CH3 | — |
| 3 | p-CH3 | H | CH3 | CH | CH2O | CH2 | O | 0 | H | C2H5 | — |
| 4 | p-CH3 | H | CH3 | CH | CH2O | CH2 | O | 0 | H | PhCH2 | — |
| 5 | m-OCH3 | H | CH3 | CH | CH2O | CH2 | O | 0 | H | CH3 | — |
| 6 | m-CH3 | H | CH3 | CH | CH2O | CH2 | O | 0 | H | CH3 | — |
| 7 | m-CF3 | H | CH3 | CH | CH2O | CH2 | O | 0 | H | CH3 | — |
| 8 | p-CH3 | H | CH3 | CH | CH2O | CH2 | O | 0 | CH3 | CH3 | — |
| 8a | p-CH3 | H | CH3 | CH | CH2O | CH2 | O | 0 | CH3 | CH3 | — |
| 9 | p-CH3 | H | CH3 | CH | CH2O | CH2 | O | 0 | cyclopentyl | | — |
| 10 | p-F | H | CH3 | CH | CH2O | CH2 | O | 0 | CH3 | CH3 | — |
| 11 | m-OCH3 | H | CH3 | CH | CH2O | CH2 | O | 0 | CH3 | CH3 | — |
| 12 | m-CF3 | H | CH3 | CH | CH2O | CH2 | O | 0 | CH3 | CH3 | — |
| 13 | 5-CH3 | H | CH3 | O | CH2O | CH2 | O | 0 | CH3 | CH3 | — |
| 14 | p-OCH3 | m-OCH3 | CH3 | CH | CH2O | CH2 | O | 0 | CH3 | CH3 | — |
| 15 | p-CH3 | H | Ph | CH | CH2O | CH2 | O | 0 | CH3 | CH3 | — |
| 16 | p-CF3 | H | CH3 | CH | CH2O | CH2 | O | 0 | CH3 | CH3 | — |
| 17 | p-OCH3 | H | CH3 | CH | CH2O | CH2 | O | 0 | CH3 | CH3 | — |
| 18 | H | H | CH3 | S | CH2O | CH2 | O | 0 | CH3 | CH3 | — |
| 19 | m-OCF3 | H | CH3 | CH | CH2O | CH2 | O | 0 | CH3 | CH3 | — |
| 20 | p-i-C3H7 | H | CH3 | CH | CH2O | CH2 | O | 0 | CH3 | CH3 | — |
| 21 | m-CH3 | H | CH3 | CH | CH2O | CH2 | O | 0 | CH3 | CH3 | — |
| 22 | p-CH3 | H | CH3 | CH | CH2O | CH2 | S | 0 | H | H | — |
| 23 | p-CH3 | H | CH3 | CH | CH2O | CH2 | S | 0 | H | CH3 | — |
| 24 | p-CH3 | H | CH3 | CH | CH2O | CH2 | S | 0 | H | C2H5 | — |
| 25 | p-CH3 | H | CH3 | CH | CH2O | CH2 | S | 0 | H | n-C5H11 | — |
| 26 | p-CH3 | H | CH3 | CH | CH2O | CH2 | S | 0 | H | i-C3H7 | — |
| 27 | p-CH3 | H | CH3 | CH | CH2O | CH2 | S | 0 | CH3 | CH3 | — |
| 28 | p-CH3 | H | CH3 | CH | CH2O | CH2 | S | 0 | H | Ph | — |
| 29 | p-CH3 | H | CH3 | CH | CH2O | CH2 | S | 0 | H | cycl-C6H11 | — |
| 30 | p-CH3 | H | CH3 | CH | CH2O | CH2 | S | 0 | H | n-C3H7 | — |
| 31 | p-CH3 | H | CH3 | CH | CH2O | CH2 | S | 0 | cyclobutyl | | — |
| 32 | p-CH3 | H | CH3 | CH | CH2O | CH2 | SO | 0 | H | H | — |
| 33 | p-CH3 | H | CH3 | CH | CH2O | CH2 | SO | 0 | H | n-C5H11 | — |
| 34 | p-CH3 | H | CH3 | CH | CH2O | CH2 | SO | 0 | CH3 | CH3 | — |
| 35 | p-CH3 | H | CH3 | CH | CH2O | CH2 | SO | 0 | H | i-C3H7 | — |
| 36 | p-CH3 | H | CH3 | CH | CH2O | CH2 | SO | 0 | H | n-C3H7 | — |
| 37 | p-CH3 | H | CH3 | CH | CH2O | CH2 | SO2 | 0 | H | H | — |
| 38 | p-CH3 | H | CH3 | CH | CH2O | CH2 | SO2 | 0 | H | n-C5H11 | — |
| 39 | p-CH3 | H | CH3 | CH | CH2O | CH2 | SO2 | 0 | CH3 | CH3 | — |
| 40 | p-CH3 | H | CH3 | CH | CH2O | CH2 | SO2 | 0 | H | i-C3H7 | — |
| 41 | p-CH3 | H | CH3 | CH | CH2O | CH2 | SO2 | 0 | H | n-C3H7 | — |
| 42 | p-CH3 | H | CH3 | CH | CH2O | CH2 | NH | 0 | H | (S)-i-C3H7 | — |
| 43 | p-CH3 | H | CH3 | CH | CH2O | CH2 | NR9 | 0 | H | (S)-i-C3H7 | COCH3 |
| 44 | p-CH3 | H | CH3 | CH | CH2O | CH2 | NR9 | 0 | H | (S)-i-C3H7 | COPh |
| 45 | p-CH3 | H | CH3 | CH | CH2O | CH2 | NR9 | 0 | H | (S)-i-C3H7 | SO2CH3 |
| 46 | p-CH3 | H | CH3 | CH | CH2O | CH2 | NR9 | 0 | H | (S)-i-C3H7 | SO2CH2—SO2CH3 |
| 47 | p-CH3 | H | CH3 | CH | CH2O | CH2 | NR9 | 0 | H | (S)-i-C3H7 | SO2(p-Tol) |
| 48 | p-CH3 | H | CH3 | CH | CH2O | CH2 | NR9 | 0 | H | (S)-i-C3H7 | COOMe |
| 49 | p-CH3 | H | CH3 | CH | CH2O | CH2 | NR9 | 0 | H | H | H |
| 50 | p-CH3 | H | CH3 | CH | CH2O | CH2 | NR9 | 0 | H | (S)-i-C3H7 | CH3 |
| 51 | p-CH3 | H | CH3 | CH | CH2O | CH2 | NR9 | 0 | H | (S)-i-C3H7 | CH2Ph |
| 52 | p-CH3 | H | CH3 | CH | CH2O | CH2 | NR9 | 0 | H | H | CH2Ph |
| 53 | p-CH3 | H | CH3 | CH | CH2O | CH2 | NR9 | 0 | H | H | 2-thienylmethyl |
| 54 | p-CH3 | H | CH3 | CH | CH2O | CH2 | NR9 | 0 | H | H | CH2(C6H11) |
| 55 | p-CH3 | H | CH3 | CH | CH2OCH2 | CH2 | O | 0 | CH3 | CH3 | — |
| 56 | p-CH3 | H | CH3 | CH | CH2OCH2 | CH2 | O | 0 | CH3 | C2H5 | — |
| 57 | p-Ph | H | CH3 | CH | CH2OCH2 | CH2 | O | 0 | CH3 | CH3 | — |
| 58 | H | H | CH3 | CH | CH2OCH2 | CH2 | O | 0 | CH3 | CH3 | — |
| 59 | 2-naphthyl | | CH3 | CH | CH2OCH2 | CH2OCH2 | O | 0 | CH3 | CH3 | — |
| 60 | m-OMe | H | C2H5 | CH | CH2OCH2 | CH2 | O | 0 | CH3 | CH3 | — |
| 61 | p-i-C3H7 | H | CH3 | CH | CH2OCH2 | CH2 | O | 0 | CH3 | CH3 | — |
| 62 | p-CH3 | H | Cy | CH | CH2OCH2 | CH2 | O | 0 | CH3 | CH3 | — |
| 63 | p-i-C3H7 | H | C2H5 | CH | CH2OCH2 | CH2 | O | 0 | CH3 | CH3 | — |

TABLE II-continued

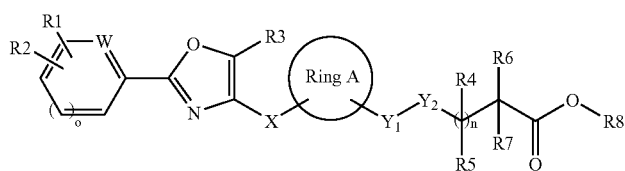

Herein below:

Ring A = cis-cyclohexane-1,3-diyl, R4 = R5 = H and R8 = H.

| Ex. | R1 | R2 | R3 | W | X | Y1 | Y2 | n | R6 | R7 | R9 |
|---|---|---|---|---|---|---|---|---|---|---|---|
| 64 | 2-naphthyl | | C2H5 | CH | CH2OCH2 | CH2OCH2 | O | 0 | CH3 | CH3 | — |
| 65 | p-CH3 | H | C2H5 | CH | CH2OCH2 | CH2 | O | 0 | CH3 | CH3 | — |
| 66 | m-CF3 | H | i-C3H7 | CH | CH2OCH2 | CH2 | O | 0 | CH3 | CH3 | — |
| 67 | m-OCH3 | H | CH3 | CH | CH2O | CH2 | CH2 | 0 | H | H | — |
| 68 | m-OCH3 | H | CH3 | CH | CH2O | CH2 | CH2 | 0 | H | CH3 | — |
| 69 | m-OCH3 | H | CH3 | CH | CH2O | CH2 | CH2 | 0 | H | C2H5 | — |
| 70 | m-OCH3 | H | CH3 | CH | CH2O | CH2 | CH2 | 0 | H | n-C3H7 | — |
| 71 | p-CH3 | H | CH3 | CH | CH2O | CH2 | CH2 | 0 | CH3 | CH3 | — |
| 72 | m-CF3 | H | CH3 | CH | CH2O | CH2 | CH2 | 0 | CH3 | CH3 | — |
| 73 | p-CH3 | H | CH3 | CH | CH2O | CH2 | CH2 | 0 | H | i-C3H7 | — |
| 74 | m-OCH3 | H | CH3 | CH | CH2O | CH2 | CH2 | 0 | H | i-C3H7 | — |
| 75 | p-CH3 | H | CH3 | CH | CH2O | CH2 | CH2 | 0 | H | PhCH2 | — |
| 76 | p-CH3 | H | CH3 | CH | CH2O | CH2 | CH2 | 0 | H | i-C4H9 | — |
| 77 | m-CF3 | H | CH3 | CH | CH2O | CH2 | CH2 | 0 | n-C3H7 | n-C3H7 | — |
| 78 | p-CH3 | H | CH3 | CH | CH2O | CH2 | CH2 | 0 | cyclopentyl | | — |
| 79 | m-CH3 | H | CH3 | CH | CH2O | C2H4 | NR9 | 0 | H | (S)-i-C3H7 | 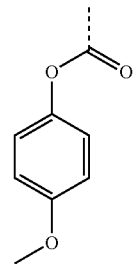 |
| 80 | m-CH3 | H | CH3 | CH | CH2O | C2H4 | NR9 | 0 | cyclopentyl | | 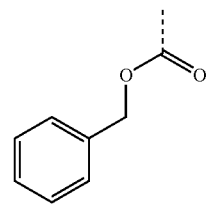 |

TABLE II-continued

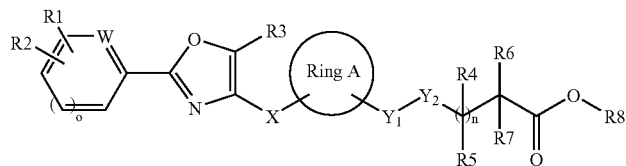

Herein below:
Ring A = cis-cyclohexane-1,3-diyl, R4 = R5 = H and R8 = H.

| Ex. | R1 | R2 | R3 | W | X | Y1 | Y2 | n | R6 | R7 | R9 |
|---|---|---|---|---|---|---|---|---|---|---|---|
| 81 | m-CH3 | H | CH3 | CH | CH2O | C2H4 | NR9 | 0 | | cyclopentyl | 4-methoxybenzyl carbamate |
| 82 | m-CH3 | H | CH3 | CH | CH2O | C2H4 | NR9 | 0 | (R)-PhCH2 | Me | 4-methoxybenzyl carbamate |
| 83 | m-CH3 | H | CH3 | CH | CH2O | C2H4 | NR9 | 0 | H | H | benzyl carbamate |
| 84 | m-CH3 | H | CH3 | CH | CH2O | C2H4 | NR9 | 0 | H | H | phenylacetyl |
| 85 | m-CH3 | H | CH3 | CH | CH2O | C2H4 | NR9 | 0 | H | H | phenylcarbamoyl |

The broken line indicates the point of attachment.

Processes

The compounds of the formula I according to the invention can be obtained according to the reaction schemes below:

Process A:

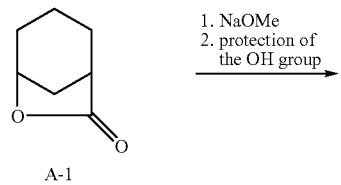

A-1

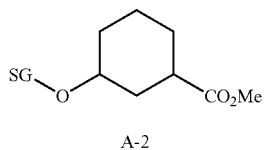

A-2

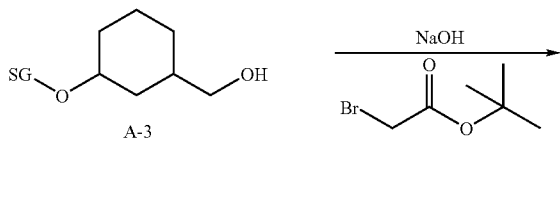

A-3

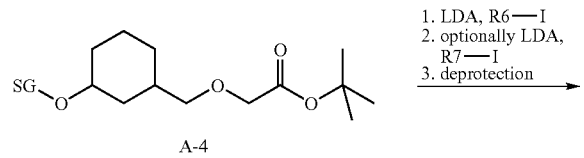

A-4

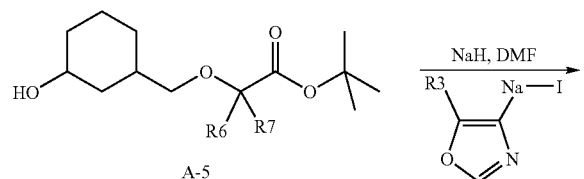

A-5

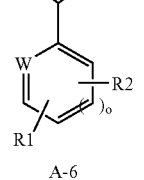

A-6

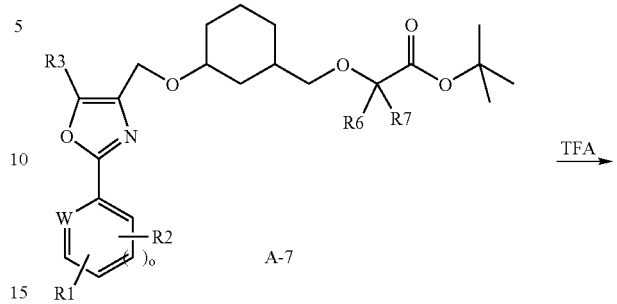

A-7

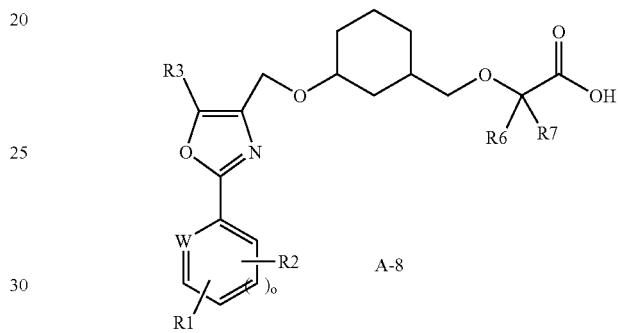

A-8

The compound A-1 is reacted in an alcohol R-8OH. The resulting product is protected on the secondary hydroxyl group (for example by stirring with TBDPSCl and imidazole in DMF at room temperature), giving the compound A-2, where R8 has the meaning described above. A-2 is, in an ethereal solvent and using lithium aluminum hydride, reduced to give compound A-3. Compound A-3 is reacted in a two-phase system of toluene and 50% strength sodium hydroxide solution at 10° C. with tert-butyl bromoacetate and tetrabutylammonium hydrogensulfate to give compound A-4.

Compound A-4 is, in tetrahydrofuran, reacted with lithium diisopropylamide and an alkyl iodide of the formula R6-I, where R6 has the meaning described above. In some examples, the compound obtained in this manner is, in tetrahydrofuran, reacted with lithium diisopropylamide and a further alkyl iodide of the formula R7-I, where R7 has the meaning described above. The protective group is removed, giving the compound of the formula A-5.

Compound A-5 is, in methyl tert-butyl ether or dimethylformamide, converted into compound A-7 using sodium hydride and the compound A-6 (see process A) where R1, R2, R3 and W have the meanings described above.

The product A-7 is stirred in trifluoroacetic acid or HCl/dioxane for a number of hours. This yields the compound of the formula A-8.

According to this process, it is possible to synthesize examples 31 to 51.

Process B:
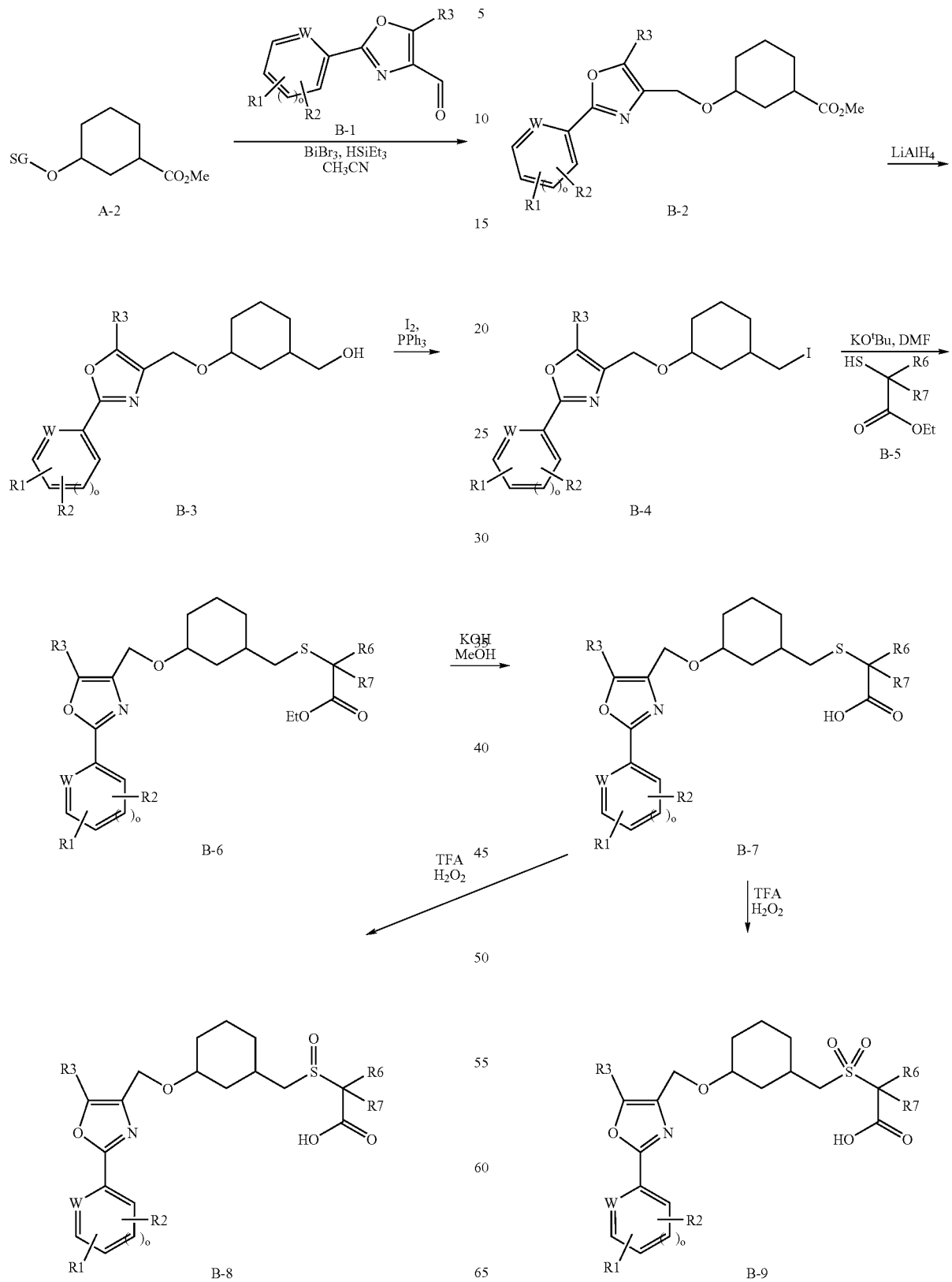

Compound A-2 where SG=tert-butyldimethylsilyl is, in acetonitrile and at room temperature, converted into compound B-2 using bismuth tribromide, triethylsilane and a compound of the formula B-1 in which R1, R2, W and R3 have the meanings described above.

Using lithium aluminum hydride in diethyl ether or THF, the compound B-2 is reduced to give compound B-3. Compound B-3 is reacted at room temperature with triphenylphosphine and iodine in toluene to give compound B-4.

Using the compound of the formula B-5 where R6 and R7 have the meanings described above, the compound B-4 is converted into compound B-6. The ester is hydrolyzed by stirring compound B-6 in a mixture of methanol and concentrated aqueous potassium hydroxide solution or lithium hydroxide in THF/methanol/water for a number of hours. This gives the compound B-7.

In some examples, the compound B-7 is oxidized at room temperature using one equivalent of hydrogen peroxide in trifluoroacetic acid to give the compound of the formula B-8 in which R1, R2, R3, R6, W and R7 have the meanings described above.

In some examples, the compound B-7 is oxidized at room temperature with three equivalents of hydrogen peroxide in trifluoroacetic acid to give the compound of the formula B-9 in which R1, R2, R3, R6, W and R7 have the meanings described above.

According to this process, it is possible to synthesize examples 52 to 71.

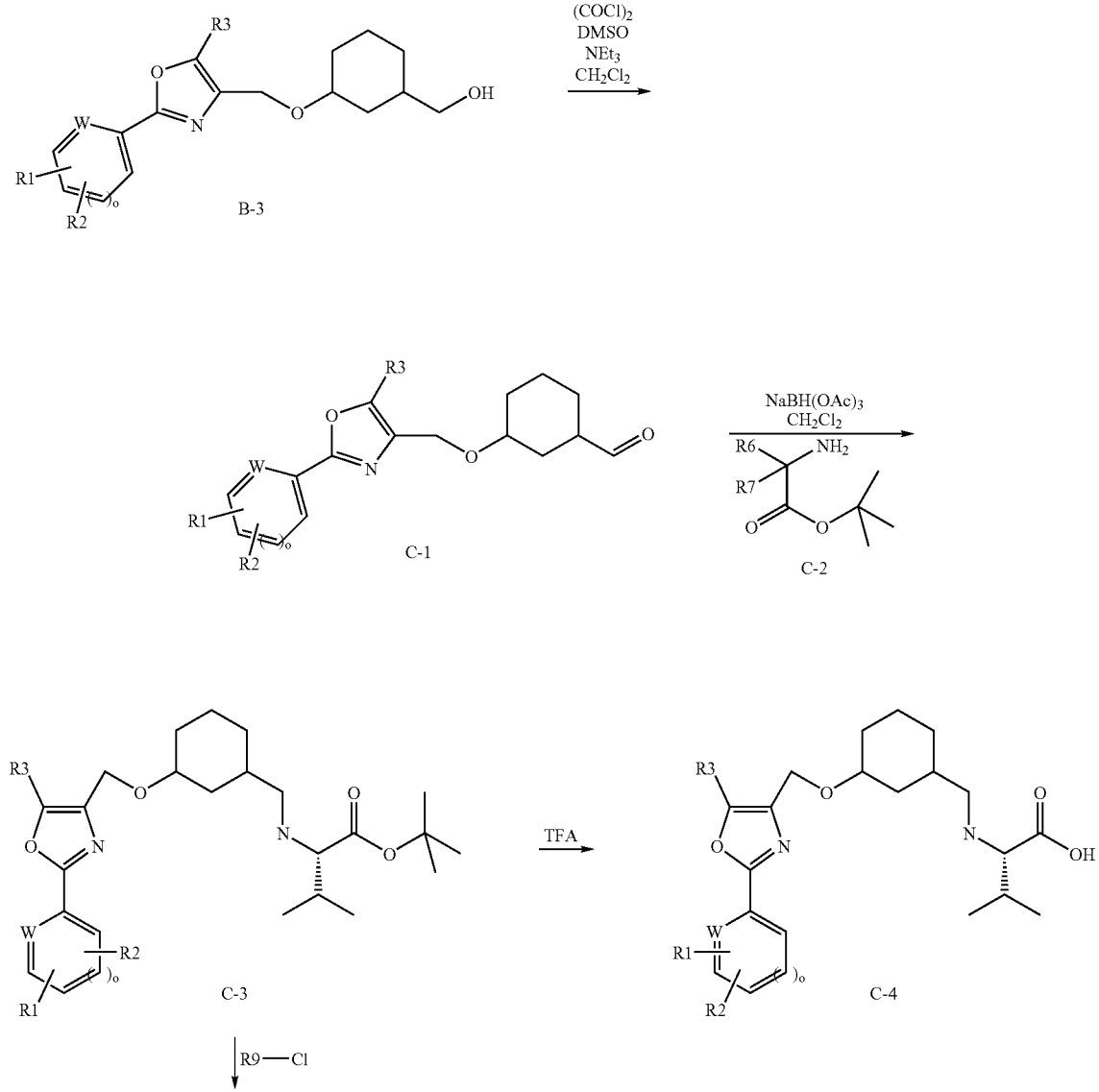

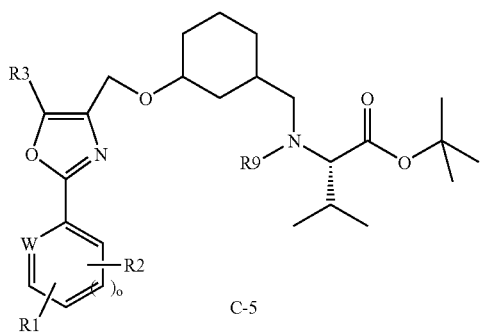

C-5

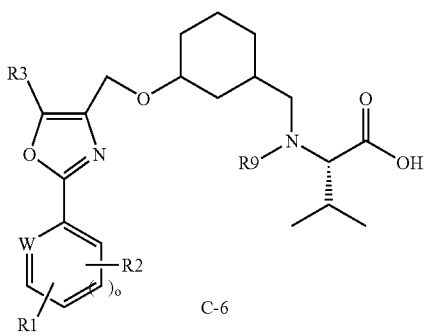

C-6

The compound B-3 (see process B) is oxidized at −78° C. with oxalyl chloride, triethylamine and dimethyl sulfoxide in dichloromethane to give aldehyde C-1. This compound is, using sodium triacetoxyborohydride and the compound of the formula C-2 where R6 and R7 have the meanings described above, converted into compound C-3.

Compound C-3 is converted into compound C-4 by stirring in trifluoroacetic acid for a number of hours.

In some examples, the compound C-3 is reacted with acyl chlorides, sulfonyl chlorides or chloroformic esters of the formula R9-Cl where R9 has the meaning described above in dichloromethane in the presence of pyridine to give the compound C-5.

By stirring in trifluoroacetic acid for a number of hours, the compound C-5 is converted into compound C-6.

According to this process, it is possible to synthesize examples 72 to 78.

Process: D

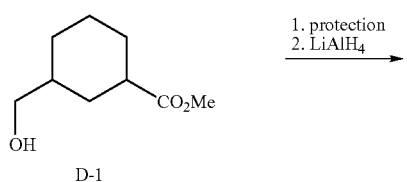

D-1

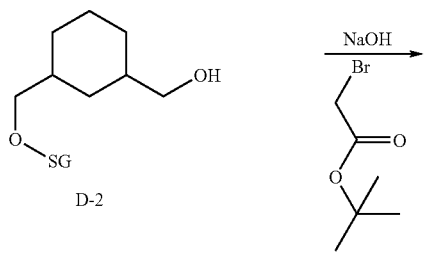

D-2

-continued

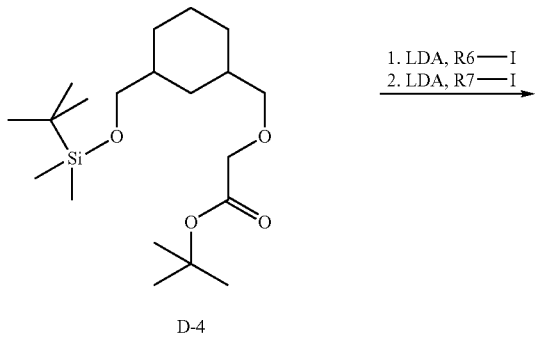

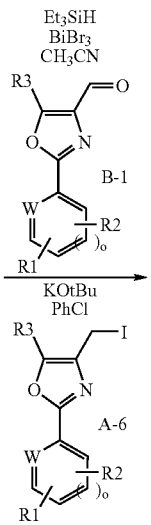

By stirring in trifluoroacetic acid, the compound D-6 is converted into compound D-7.

Using this process, it is possible to synthesize examples 79 and 80.

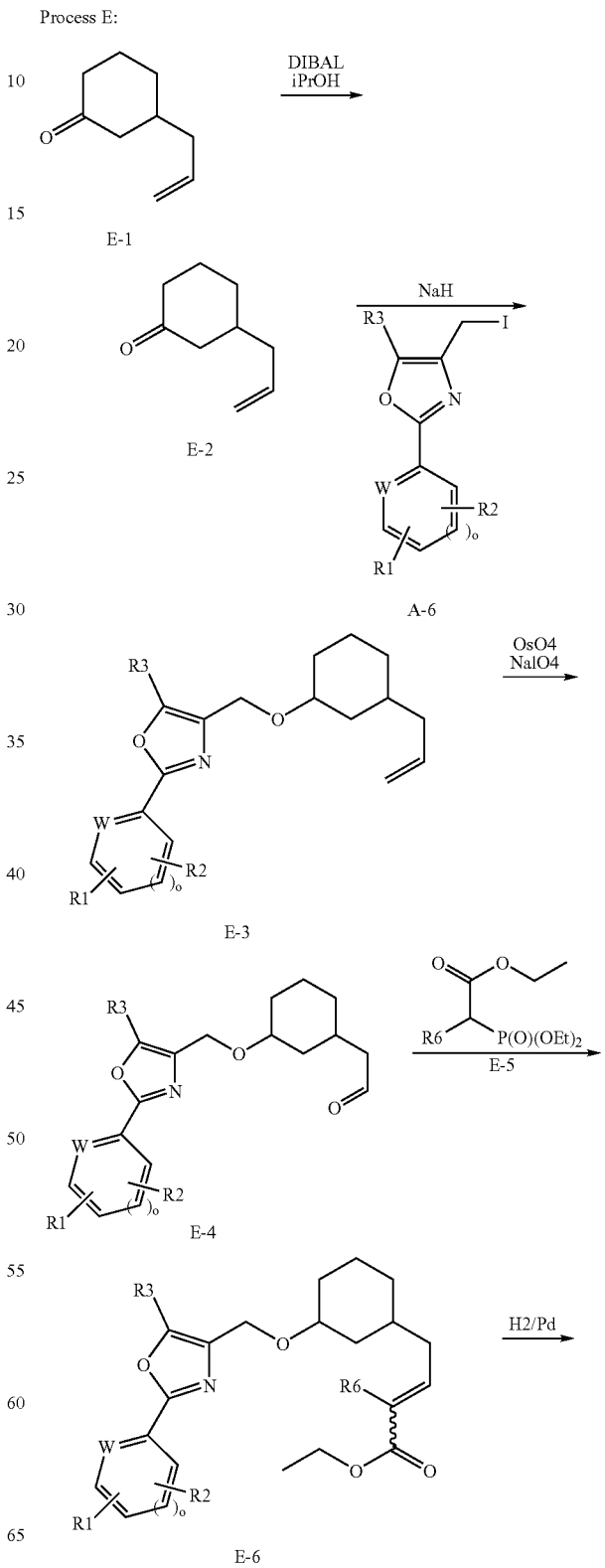

The compound D-1 is protected on the hydroxyl group with a suitable protective group, for example with the methoxymethyl protective group. The carboxyl group is then converted with lithium aluminum hydride in diethyl ether into compound D-2. This compound is reacted with tert-butyl bromoacetate and tetrabutylammonium hydrogensulfate in a two-phase system of toluene/50% strength aqueous sodium hydroxide solution to give compound D-3.

Compound D-3 is deprotected (using, for example, concentrated hydrochloric acid in tetrahydrofuran in the case of the methoxymethyl protective group) and then converted with tert-butyldimethylsilyl chloride and imidazole in dimethylformamide into compound D-4.

Compound D-4 is deprotonated at 0° C. using lithium diisopropylamide in tetrahydrofuran and reacted with an alkyl iodide of the formula R6-I, where R6 has the meaning described above. The resulting compound is then deprotonated at 0° C. using lithium diisopropylamide in tetrahydrofuran and reacted with an alkyl iodide of the formula R7-I, where R7 has the meaning described above, to give the compound D-5.

Compound D-5 is reacted with bismuth tribromide, triethylsilane and the compound B-1 (see process B) in acetonitrile at room temperature or—after removal of the silyl protective group using TBAF in THF—with potassium tert-butoxide and the compound A-6 (see process A) to give the compound D-6.

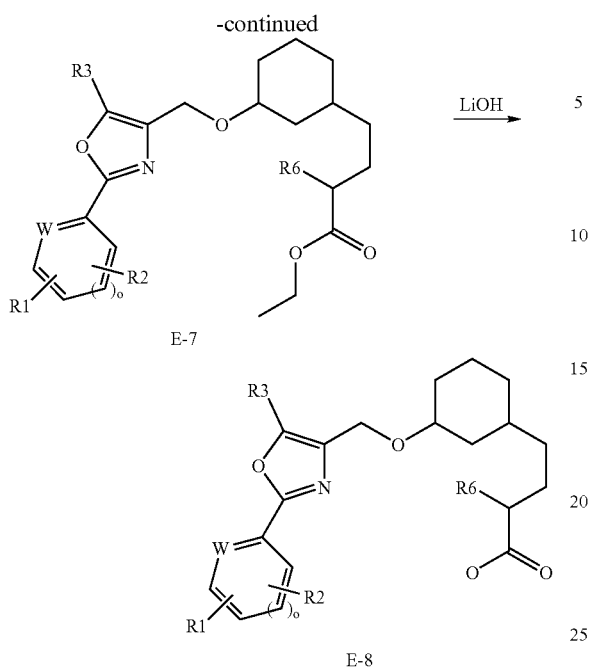

E-7

E-8

Using diisobutylaluminum hydride and isopropanol in diethyl ether, the compound E-1 is reduced to give compound E-2. This is reacted with the compound of the formula A-6 and sodium hydride in dimethylformamide to give compound E-3.

Using osmium tetroxide and sodium periodate in diethyl ether, compound E-3 is converted into aldehyde E-4. In a Horner-Emmons-Wadsworth reaction, using a triethyl phosphonoacetate of the formula E-5 in which R6 is as defined above, this compound is converted into compound E-6.

Using hydrogen, the compound E-6 is hydrogenated over palladium/carbon to give compound E-7, and the ester is then hydrolyzed using lithium hydroxide to give the acid E-8.

According to this process, it is possible to synthesize examples 81 to 84.

Process F:

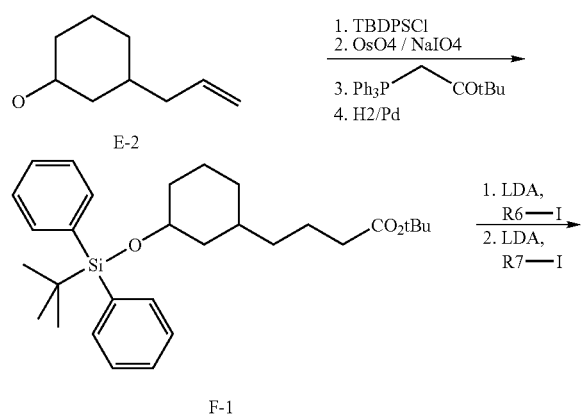

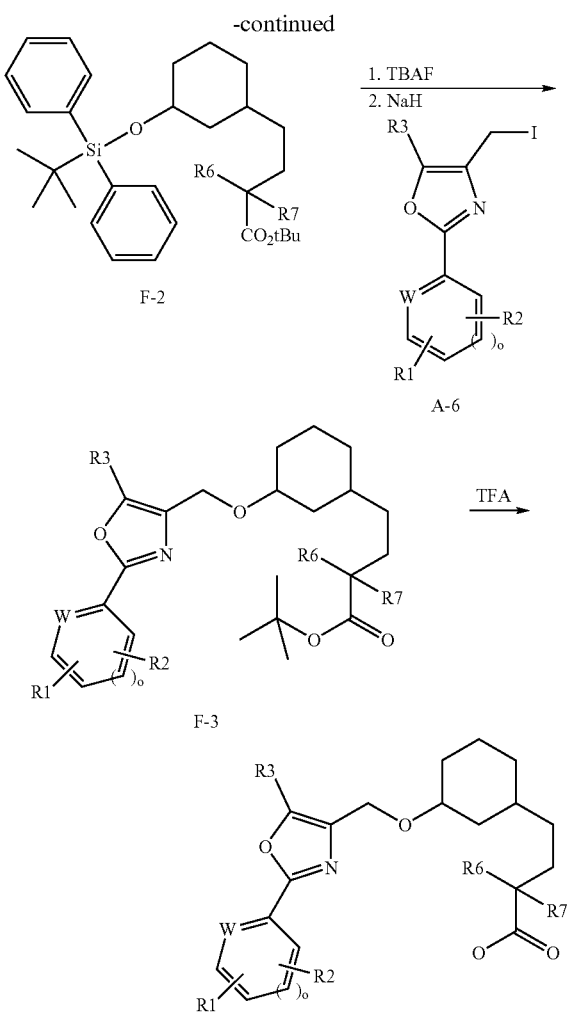

Using tert-butyldiphenylsilyl chloride and imidazole as base in dimethylformamide, the compound E-2 is reacted, worked up and then reacted with osmium tetroxide and sodium periodate in diethyl ether. The resulting compound is reacted with tert-butyl triphenylphosphoranylidene-acetate and n-butyllithium in a Wittig reaction and then hydrogenated with hydrogen over palladium/carbon to give compound F-1.

At 0° C., the compound F-1 is deprotonated using lithium diisopropylamide in tetrahydrofuran and reacted with an alkyl iodide of the formula R6-I, where R6 is as defined above. The resulting compound is then deprotonated using lithium diisopropylamide in tetrahydrofuran at 0° C. and reacted with an alkyl iodide of the formula R7-I where R7 is as defined above to give the compound F-2.

For deprotection, the compound F-2 is reacted with tetrabutylammonium fluoride in tetrahydrofuran. The resulting alcohol is then reacted with sodium hydride and the compound A-6 in dimethylformamide to give compound F-3.

The tert-butyl ester is cleaved by stirring compound F-3 for a number of hours in trifluoroacetic acid, giving the compound F-4.

Examples 85 to 92 were synthesized according to this process.

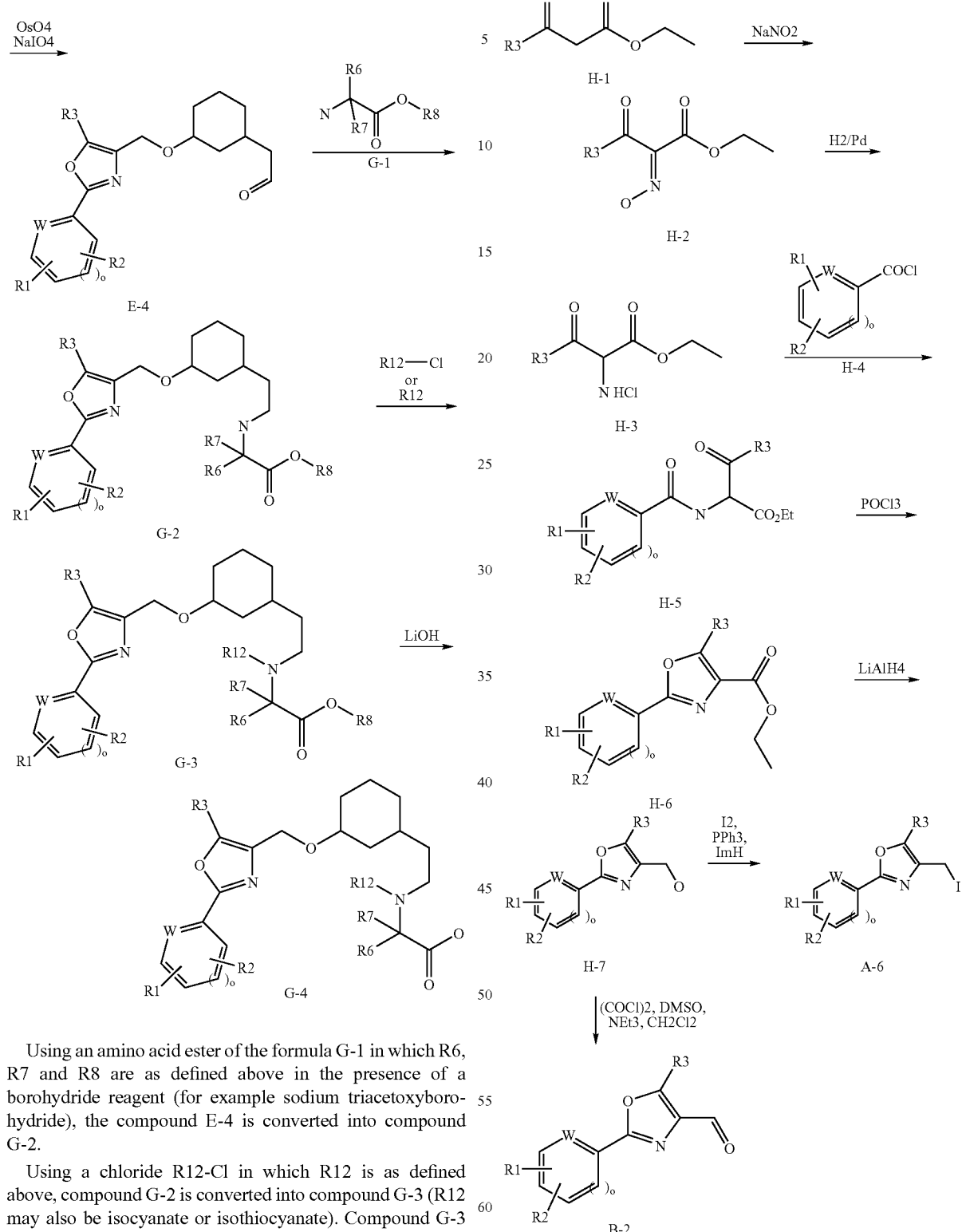

Using an amino acid ester of the formula G-1 in which R6, R7 and R8 are as defined above in the presence of a borohydride reagent (for example sodium triacetoxyborohydride), the compound E-4 is converted into compound G-2.

Using a chloride R12-Cl in which R12 is as defined above, compound G-2 is converted into compound G-3 (R12 may also be isocyanate or isothiocyanate). Compound G-3 is then hydrolyzed with LiOH to give compound G-4.

Process H:

This process is used for the synthesis of building blocks A-6 and B-2 in which R1, R2, W and R3 are as defined above.

Using sodium nitrite and hydrochloric acid, the ester H-1 in which R3 is as defined above is converted into oxime H-2 which is reduced by hydrogenation with hydrogen over palladium/carbon to give amine H-3.

Using acid chlorides of the formula H-4 in which R1, W and R2 are as defined above and base (for example triethylamine), the compound H-3 is converted into compound H-5.

By heating in phosphoryl chloride, the compound H-5 is converted into compound H-6.

The ester H-6 is reduced with lithium aluminum hydride in diethyl ether to give alcohol H-7. This is converted into the iodide A-6 using iodine, imidazole (ImH) and triphenylphosphine.

Alternatively, the compound H-7 is oxidized using oxalyl chloride, dimethyl sulfoxide and triethylamine in dichloromethane at −78° C. to give aldehyde B-1.

Process J:

This process is used for synthesizing the building block A-6 in which R1, R2, W and R3 are as defined above.

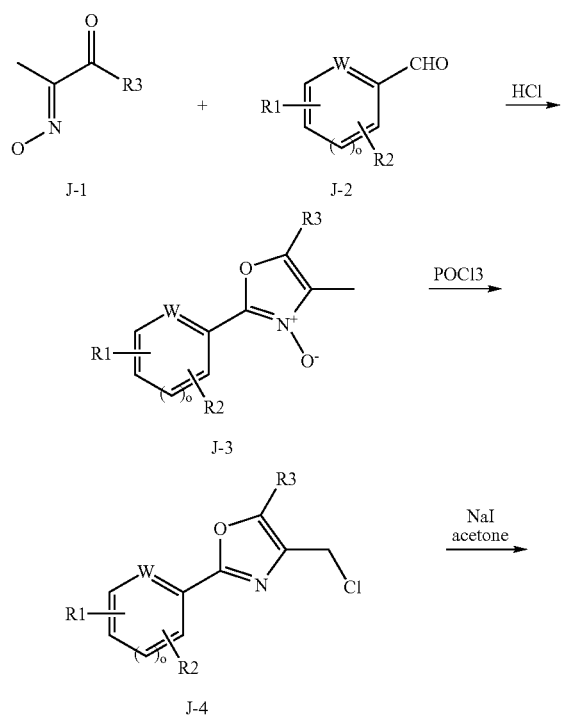

In ethanol and using hydrogen chloride, the compound J-1 is reacted with the aldehyde J-2 in which R1, R2, W and R3 are as defined above, to give the compound J-3.

The compound J-3 is heated to the boil in phosphoryl chloride, giving the compound J-4. This is heated to the boil with sodium iodide in acetone. This gives the compound A-6.

The abbreviations used denote:

| | |
|---|---|
| Ac | Acetyl |
| Bn | Benzyl |
| iBu | Isobutyl |
| tBu | tert-Butyl |
| BuLi | n-Butyllithium |
| Bz | Benzoyl |
| Cy | Cyclohexyl |
| TLC | Thin-layer chromatography |
| DCI | Direct chemical ionization (in MS) |
| DCM | Dichloromethane |
| DMAP | 4-N,N-Dimethylaminopyridine |
| DMF | N,N-Dimethylformamide |
| DMSO | Dimethyl sulfoxide |
| EA | Ethyl acetate |
| EDC | N'-(3-Dimethylaminopropyl)-N-ethylcarbodiimide × HCl |
| EI | Electron impact ionization (in MS) |
| eq | Equivalent |
| ESI | Electrospray ionization (in MS) |
| Et | Ethyl |
| sat. | Saturated |
| h | Hour |
| HATU | O-(7-Azabenzotriazol-1-yl)-N,N,N',N'-tetramethyluronium hexafluorophosphate |
| HOBt | 1-Hydroxy-1H-benzotriazole × $H_2O$ |
| HPLC | High pressure, high performance liquid chromatography |
| LC-MS | Liquid chromatography-coupled mass spectroscopy |
| Me | Methyl |
| MS | Mass spectroscopy |
| MsCl | Methanesulfonyl chloride |
| NMR | Nuclear magnetic resonance spectroscopy |
| Pd/C | Palladium on carbon |
| iPr | Isopropyl |
| nPr | n-Propyl |
| Rf | Retention time (in TLC) |
| RT | Room temperature |
| TBAF | Tetrabutylammonium fluoride |
| TBAI | Tetrabutylammonium iodide |
| TBDPSCl | tert-Butyldiphenylsilyl chloride |
| TBDMSCl | tert-Butyldimethylsilyl chloride |
| THF | Tetrahydrofuran |
| Tr | Trityl |

It is possible to prepare other compounds by the processes mentioned above.

Building Block Synthesis According to Process H:

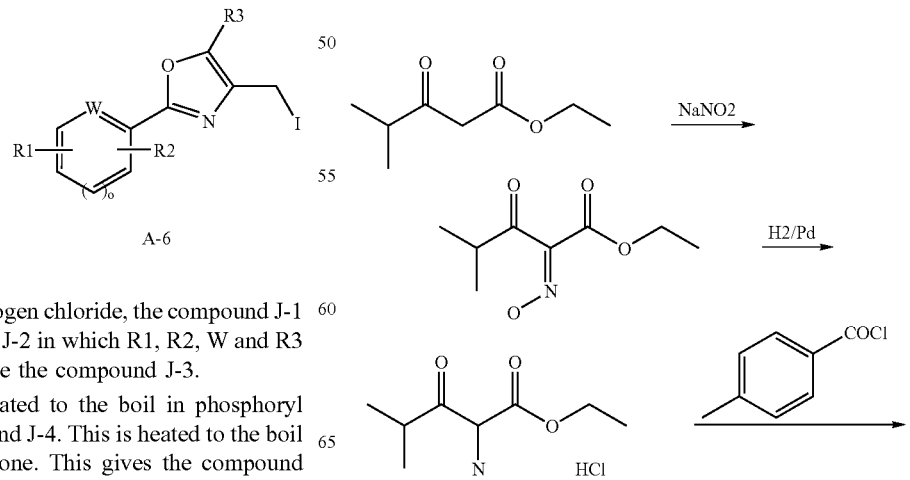

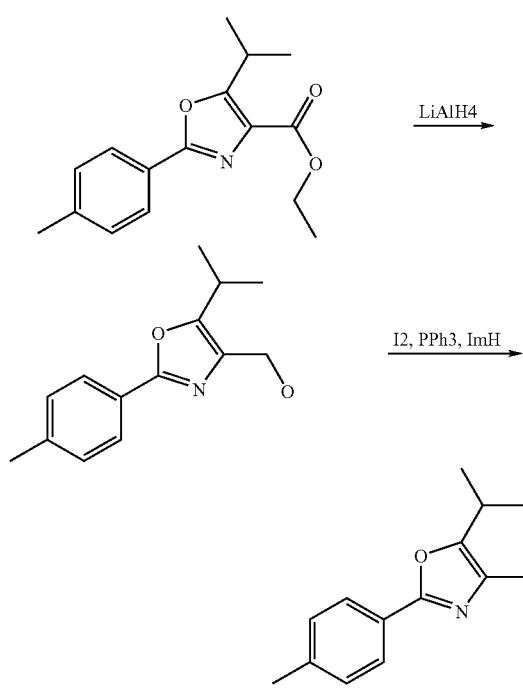

Ethyl 2-hydroxyimino-4-methyl-3-oxopentanoate

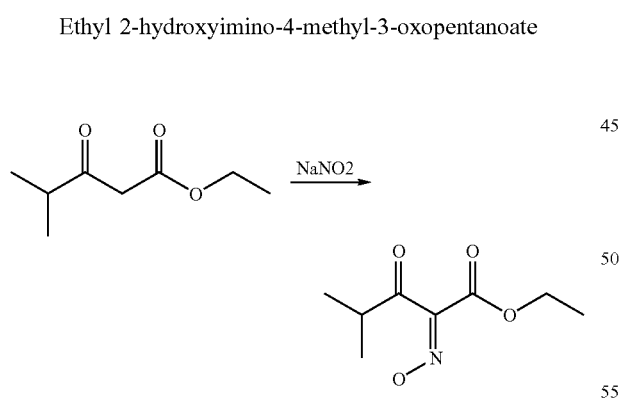

42.4 g of ethyl 4-methyl-3-oxopentanoate are dissolved in 100 ml of glacial acetic acid, and 21 g of sodium nitrite, dissolved in 100 ml of water, are added at 5° C. Over a period of one hour, the mixture is allowed to warm to room temperature, 100 ml of water are added and the mixture is stirred at room temperature for another hour. The mixture is extracted three times with in each case 150 ml of methyl tert-butyl ether, 200 ml of water are added to the combined organic phases and the mixture is neutralized by addition of solid NaHCO3. The organic phase is removed, washed with saturated NaCl solution and dried over MgSO4, and the solvent is removed under reduced pressure. This gives 46 g of ethyl 2-hydroxyimino-4-methyl-3-oxopentanoate as an oil. C8H13NO4 (187.20), MS (ESI)=188 (M+H$^+$).

Ethyl 2-amino-4-methyl-3-oxopentanoate hydrochloride

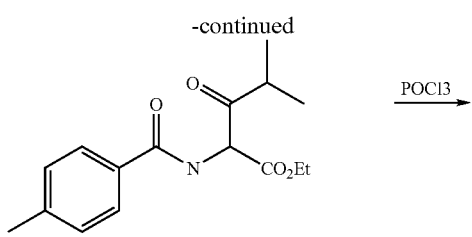

10 g of HCl are introduced into 200 ml of ethanol. 46 g of ethyl 2-hydroxy-imino-4-methyl-3-oxopentanoate are dissolved in this mixture, 5 g of Pd (10% on carbon) are added and the mixture is stirred under atmosphere of hydrogen (5 bar) for 8 hours. The reaction mixture is filtered through Celite and the solvent is removed under reduced pressure. This gives 45 g of ethyl 2-amino-4-methyl-3-oxopentanoate hydrochloride as a white solid. C8H15NO3*HCl (209.5), MS (ESI)=188 (M+H$^+$).

Ethyl 4-methyl-2-(4-methylbenzoylamino)-3-oxopentanoate 10 g of ethyl 2-amino-4-methyl-3-oxopentanoate hydrochloride and 7.4 g of 4-methylbenzoyl chloride are dissolved in 250 ml of dichloromethane, and 13.3 ml of triethylamine are slowly added dropwise at 0° C. The mixture is stirred at room temperature for one hour and then washed with water, the organic phase is separated off and dried over MgSO4 and the solvent is then removed under reduced pressure. This gives 13 g of ethyl 4-methyl-2-(4-methylbenzoylamino)-3-oxopentanoate as an oil. C16H21NO4 (291.35), MS (ESI) =292 (M+H$^+$).

Ethyl 5-isopropyl-2-p-tolyloxazole-4-carboxylate

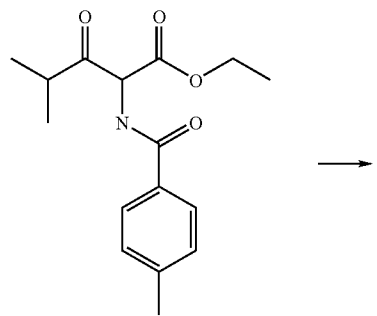

13 g of ethyl 4-methyl-2-(4-methylbenzoylamino)-3-oxo-pentanoate in 80 ml of phosphorus oxychloride are heated to the boil under reflux for 2 h. The phosphorus oxychloride is removed under reduced pressure and the resulting residue is dissolved in 200 ml of dichloromethane, washed three times with saturated NaHCO$_3$ solution and dried over MgSO4, and the solvent is then removed under reduced pressure. This gives 11 g of ethyl 5-isopropyl-2-p-tolyloxazole-4-carboxylate as a brownish sold. C16H19NO3 (273.33), MS (ESI) =292 (M+H$^+$), Rf(n-heptane:ethyl acetate)=2:1)=0.43.

(5-Isopropyl-2-p-tolyloxazol-4-yl)methanol

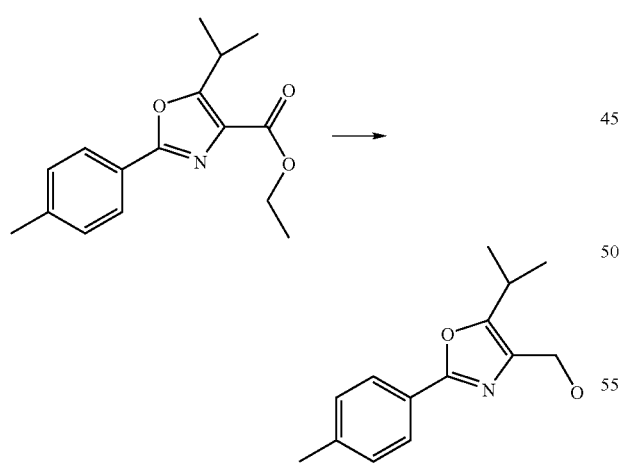

11 g of ethyl 5-isopropyl-2-p-tolyloxazole-4-carboxylate are dissolved in 100 ml of tetrahydrofuran, and 40 ml of a 1 molar solution of lithium aluminum hydride in tetrahydrofuran are added at 0° C. After 30 min, 1N of HCl are added to the reaction mixture, and the mixture is extracted five times with ethyl acetate. The combined organic phases are dried over MgSO4 and the solvent is then removed under reduced pressure. The residue is purified on silica gel using the mobile phase n-heptane:ethyl acetate=6:1=>1:1. This gives 4.3 g of (5-isopropyl-2-p-tolyloxazol-4-yl)methanol as a light-yellow solid.
C14H17NO2 (231.30), MS (ESI)=232 (M+H$^+$), Rf(n-heptane:ethyl acetate)=1:1)=0.17.

4-Iodomethyl-5-isopropyl-2-p-tolyloxazole

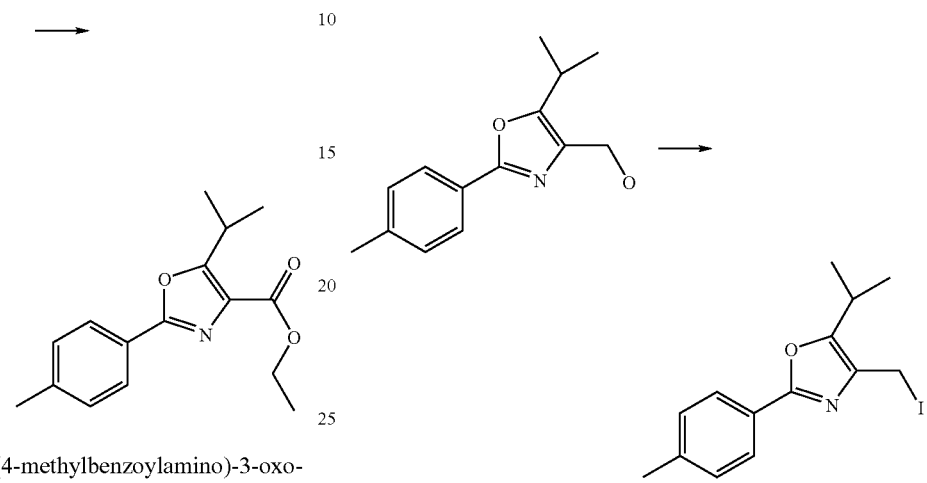

500 mg of (5-isopropyl-2-p-tolyloxazol-4-yl)methanol, together with 690 mg of triphenylphosphine and 600 mg of imidazole, are dissolved in 20 ml of toluene. 715 mg of iodine are added, and the mixture is stirred at room temperature for 1 hour. 10 ml of saturated sodium carbonate solution and 500 mg of iodine are then added. After 10 minutes, the organic phase is separated off, washed twice with saturated Na2S2O3 solution and dried over MgSO4, and the solvents are then removed under reduced pressure. The residue is purified on silica gel using the mobile phase n-heptane:ethyl acetate=10:1. This gives 400 mg of 4-iodomethyl-5-isopropyl-2-p-tolyl-oxazole as a white solid. C14H16INO (341.19), MS (ESI): 342 (M+H$^+$), Rf(n-heptane:ethyl acetate=1:1)=0.75.

Analogously to the building block synthesis according to process K, ethyl 2-amino-4-methyl-3-oxopentanoate hydrochloride and 3-methoxybenzoyl chloride gave 4-iodomethyl-2-(3-methoxyphenyl)-5-isopropyloxazole.

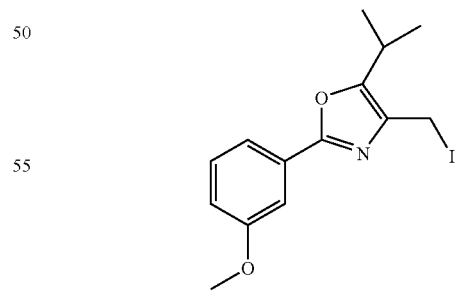

C14H16INO2 (357.19), MS (ESI): 358 (M+H$^+$), Rf(n-heptane:ethyl acetate=1:1)=0.60.

Analogously to the building block synthesis of 4-iodomethyl-5-isopropyl-2-p-tolyloxazole, ethyl 4,4,4-trifluoro-3-oxobutyrate and 3-methoxybenzoyl chloride gave 4-iodomethyl-2-(3-methoxyphenyl)-5-trifluoromethyloxazole.

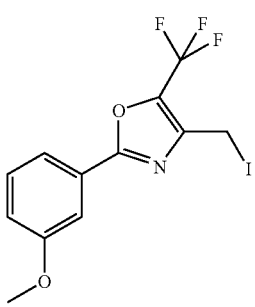

C12H9F3INO2 (383.11), MS (ESI): 384 (M+H⁺).

Analogously to the building block synthesis of 4-iodomethyl-5-isopropyl-2-p-tolyloxazole, ethyl 4,4,4-trifluoro-3-oxobutyrate and 3-trifluoromethyl-benzoyl chloride gave 4-iodomethyl-2-(3-trifluoromethylphenyl)-5-trifluoro-methyloxazole.

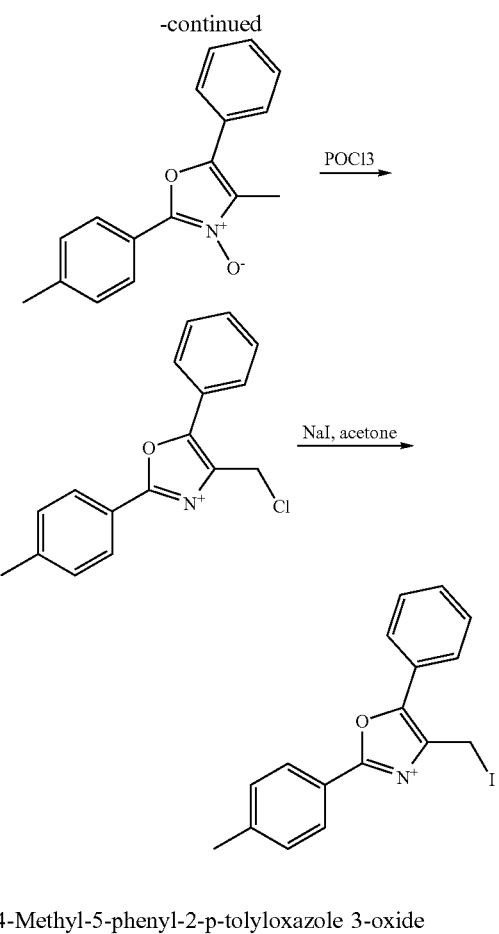

C12H6F6INO (421.08), MS (ESI): 422 (M+H⁺).

Analogously to the building block synthesis of 4-iodomethyl-5-isopropyl-2-p-tolyloxazole, ethyl 4,4,4-trifluoro-3-oxobutyrate and 4-methylbenzoyl chloride gave 4-iodomethyl-5-trifluoromethyl-2-p-tolyloxazole.

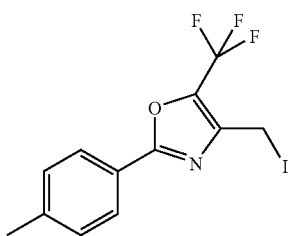

C12H9F3INO (367.11), MS (ESI): 368 (M+H⁺).

Building Block Synthesis According to Process J:

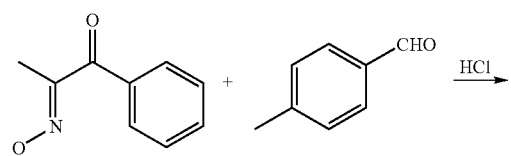

4-Methyl-5-phenyl-2-p-tolyloxazole 3-oxide 12.5 g of 1-phenyl-1,2-propanedione-2-oxime and 10 ml of p-tolualdehyde are added to 50 ml of glacial acetic acid, and HCl gas is introduced for 30 minutes, with ice-cooling. The product is precipitated as the hydrochloride by addition of methyl tert-butyl ether and filtered off with suction, and the precipitate is washed with methyl tert-butyl ether. The precipitate is suspended in water and the pH is made alkaline using ammonia. The mixture is extracted three times with in each case 200 ml of dichloromethane, the combined organic phases are dried over MgSO4 and the solvent is then removed under reduced pressure. This gives 6.4 g of 4-methyl-5-phenyl-2-p-tolyloxazole 3-oxide as a white solid. C17H15NO2 (265.31), MS (ESI)=266 (M+H⁺).

4-Chloromethyl-5-phenyl-2-p-tolyloxazole

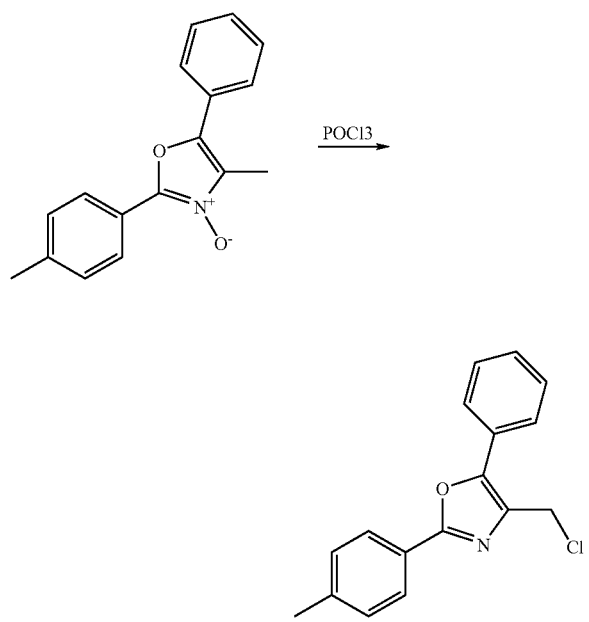

6.4 g of 4-methyl-5-phenyl-2-p-tolyloxazole 3-oxide are dissolved in 50 ml of chloroform, 2.4 ml of phosphorus oxychloride are added and the mixture is, under reflux, heated at the boil for 30 minutes. The reaction mixture is cooled to 0° C., the pH is made slightly alkaline using ammonia and the mixture is extracted three times with in each case 100 ml of ethyl acetate. The combined organic phases are washed with water and dried over MgSO4, and the solvent then removed under reduced pressure. This gives 5.4 g of 4-chloromethyl-5-phenyl-2-p-tolyloxazole as a yellow solid. C17H14ClNO (283.76), MS (ESI)=284 (M+H⁺), Rf(n-heptane:ethyl acetate)=7:1)=0.41

4-Iodomethyl-5-phenyl-2-p-tolyloxazole

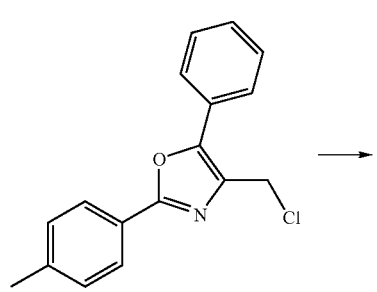

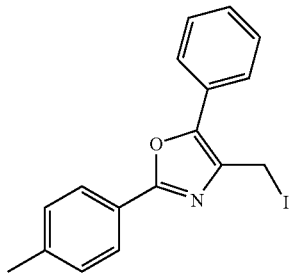

Together with 3 g of sodium iodide, 1.8 g of 4-chloromethyl-5-phenyl-2-p-tolyloxazole are, in 150 ml of acetone, heated at the boil under reflux for 2 hours. After cooling of the reaction mixture, 300 ml of methyl tert-butyl ether are added, the mixture is washed three times with saturated Na2S2O3 solution and dried over MgSO4 and the solvents are then removed under reduced pressure. This gives 2.7 g of 4-iodomethyl-5-phenyl-2-p-tolyloxazole as a light-yellow solid.

C17H14INO (375.21), MS (ESI): 376 (M+H⁺).

Analogously to the building block synthesis of 4-iodomethyl-5-phenyl-2-p-tolyloxazole, 1-phenyl-1,2-propanedione-2-oxime and m-anisaldehyde gave 4-iodomethyl-2-(3-methoxyphenyl)-5-phenyloxazole.

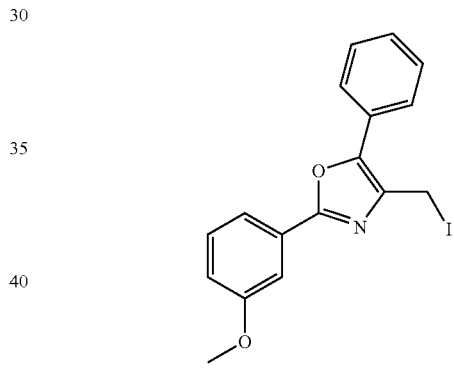

C17H14INO2 (391.21), MS (ESI): 392 (M+H⁺).

Analogously to the building block synthesis of 4-iodomethyl-5-phenyl-2-p-tolyloxazole, 1-ethyl-1,2-propanedione-2-oxime and m-anisaldehyde gave 4-iodomethyl-5-ethyl-2-(3-methoxyphenyl)oxazole.

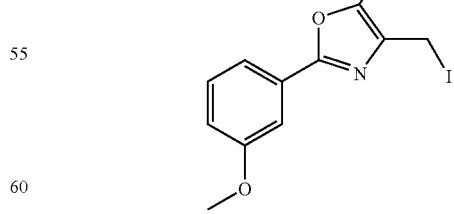

C13H14INO2 (343.17), MS (ESI): 344 (M+H⁺).

Analogously to the building block synthesis of 4-iodomethyl-5-phenyl-2-p-tolyloxazole, 1-ethyl-1,2-propanedione-2-oxime and p-tolualdehyde gave 4-iodomethyl-5-ethyl-2-p-tolylazole.

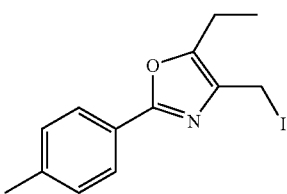

C13H14INO (327.17), MS (ESI): 328 (M+H⁺).

Analogously to the building block synthesis of 4-iodomethyl-5-phenyl-2-p-tolyloxazole, 1-cyclohexyl-1,2-propanedione-2-oxime and m-anis-aldehyde gave 4-iodoethyl-5-cyclohexyl-2-(3-methoxyphenyl)oxazole.

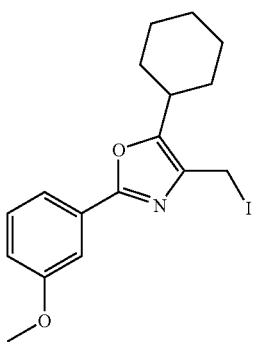

C17H20INO2 (397.26), MS (ESI): 398 (M+H⁺).

Analogously to the building block synthesis of 4-iodomethyl-5-phenyl-2-p-tolyloxazole, 1-cyclohexyl-1,2-propanedione-2-oxime and p-tolu-aldehyde gave 4-iodomethyl-5-cyclohexyl-2-p-tolyloxazole.

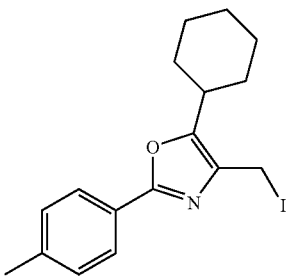

C17H20INO (381.26), MS (ESI): 382 (M+H⁺).

Analogously to the building block synthesis of 4-iodomethyl-5-phenyl-2-p-tolyloxazole, diacetylmonoxime and p-tolualdehyde gave 4-iodomethyl-5-methyl-2-p-tolyloxazole.

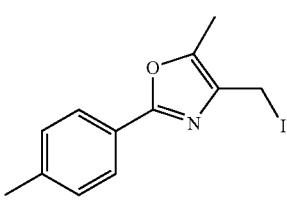

C12H12INO (313.14), MS (ESI): 314 (M+H⁺).

Analogously to the building block synthesis of 4-iodomethyl-5-phenyl-2-p-tolyloxazole, diacetylmonoxime and m-anisaldehyde gave 4-iodo-methyl-2-(3-methoxyphenyl)-5-methyloxazole.

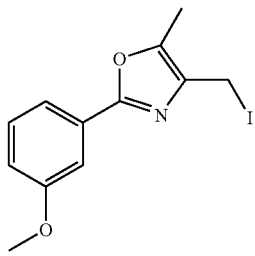

C12H12INO2 (329.14), MS (ESI): 330 (M+H⁺).

Analogously to the building block synthesis of 4-iodomethyl-5-phenyl-2-p-tolyloxazole, diacetylmonoxime and 3-bromobenzaldehyde gave 2-(3-bromophenyl)-4-iodomethyl-5-methyloxazole.

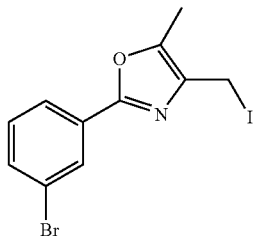

C11H9BrINO (377.01/379.01), MS (ESI): 378/380 (M+H⁺).

Analogously to the building block synthesis of 4-iodomethyl-5-phenyl-2-p-tolyloxazole, diacetylmonoxime and 3-trifluoromethylbenzaldehyde gave 4-iodomethyl-5-methyl-2-(3-trifluoromethylphenyl)oxazole.

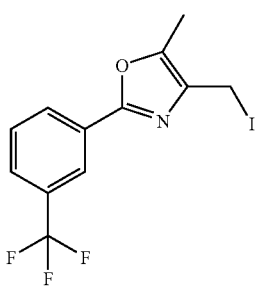

C12H9F3INO (367.11), MS (ESI): 368 (M+H⁺).

Analogously to the building block synthesis of 4-iodomethyl-5-phenyl-2-p-tolyloxazole, diacetylmonoxime and 4-fluorobenzaldehyde gave 2-(4-fluorophenyl)-4-iodomethyl-5-methyloxazole.

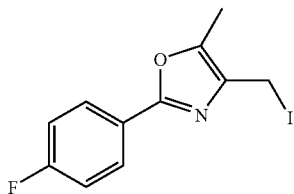

C11H9FINO (317.10), MS (ESI): 318 (M+H+).

Analogously to the building block synthesis of 4-iodomethyl-5-phenyl-2-p-tolyloxazole, diacetylmonoxime and 4-methoxybenzaldehyde gave 4-iodomethyl-2-(4-methoxyphenyl)-5-methyloxazole.

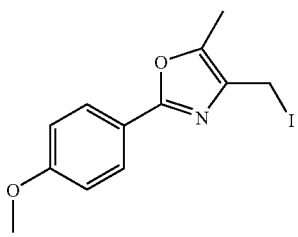

C12H12INO2 (329.14), MS (ESI): 330 (M+H+).

Analogously to the building block synthesis of 4-iodomethyl-5-phenyl-2-p-tolyloxazole, diacetylmonoxime and 4-trifluoromethylbenzaldehyde gave 4-iodomethyl-5-methyl-2-(4-trifluoromethylphenyl)oxazole.

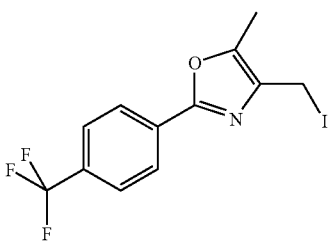

C12H9F3INO (367.11), MS (ESI): 368 (M+H+).

Analogously to the building block synthesis of 4-iodomethyl-5-phenyl-2-p-tolyloxazole, diacetylmonoxime and m-tolualdehyde gave 4-iodomethyl-5-methyl-2-m-tolyloxazole.

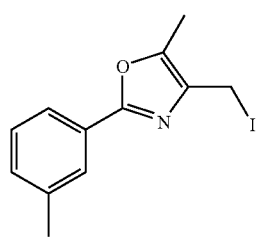

C12H12INO (313.14), MS (ESI): 314 (M+H+).

Analogously to the building block synthesis of 4-iodomethyl-5-phenyl-2-p-tolyloxazole, diacetylmonoxime and benzaldehyde gave 4-chloro-methyl-5-methyl-2-phenyloxazole.

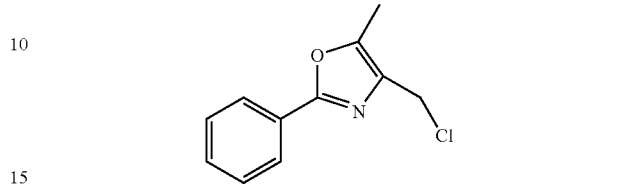

C11H10ClNO (299.15) MS (ESI): 300 (M+H+).

Analogously to the building block synthesis of 4-iodomethyl-5-phenyl-2-p-tolyloxazole, diacetylmonoxime and p-phenylbenzaldehyde gave 4-iodomethyl-5-methyl-2-p-biphenyloxazole.

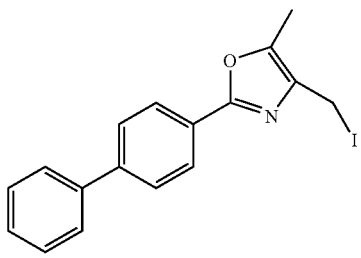

C18H13INO (375.21), MS (ESI):376 (M+H+).

Analogously to the building block synthesis of 4-iodomethyl-5-phenyl-2-p-tolyloxazole, diacetylmonoxime and 3-trifluoromethoxybenzaldehyde gave 4-iodomethyl-5-methyl-2-(3-trifluoromethoxyphenyl)oxazole.

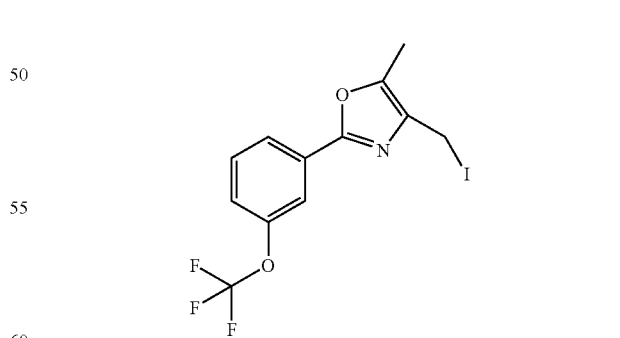

C12H9F3INO2 (383.11), MS (ESI): 384 (M+H+).

Analogously to the building block synthesis of 4-iodomethyl-5-phenyl-2-p-tolyloxazole, diacetylmonoxime and 5-methylfuran-2-carbaldehyde gave 4-iodomethyl-5-methyl-2-(5-methylfuran-2-yl)oxazole.

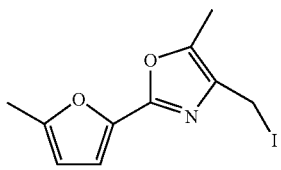

C10H10INO2 (303.11), MS (ESI): 304 (M+H+).

Analogously to the building block synthesis of 4-iodomethyl-5-phenyl-2-p-tolyloxazole, diacetylmonoxime and thiophene-2-carbaldehyde gave 4-iodomethyl-5-methyl-2-thiophen-2-yloxazole.

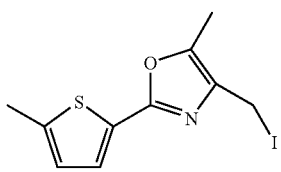

C9H8INOS (305.14), MS (ESI): 306 (M+H+).

Analogously to the building block synthesis of 4-iodomethyl-5-phenyl-2-p-tolyloxazole, diacetylmonoxime and 4-isopropylbenzaldehyde gave 4-iodomethyl-2-(4-isopropylphenyl)-5-methyloxazole.

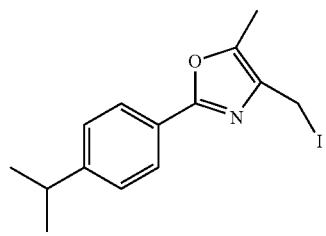

C14H16INO (341.19), MS (ESI): 342 (M+H+).

Analogously to the building block synthesis of 4-iodomethyl-5-phenyl-2-p-tolyloxazole, pentane-2,3-dione-2-oxime and 3-trifluoromethyl-benzaldehyde gave 5-ethyl-4-iodomethyl-2-(3-trifluoromethylphenyl)-oxazole.

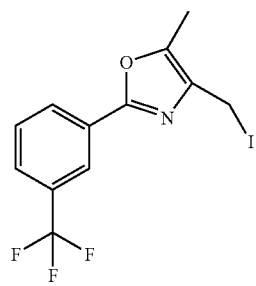

C13H11F3INO (381.14), MS (ESI): 382 (M+H+).

Analogously to the building block synthesis of 4-iodomethyl-5-phenyl-2-p-tolyloxazole, pentane-2,3-dione-2-oxime and naphthalene-2-carbaldehyde gave 5-ethyl-4-iodomethyl-2-naphthalen-2-yloxazole.

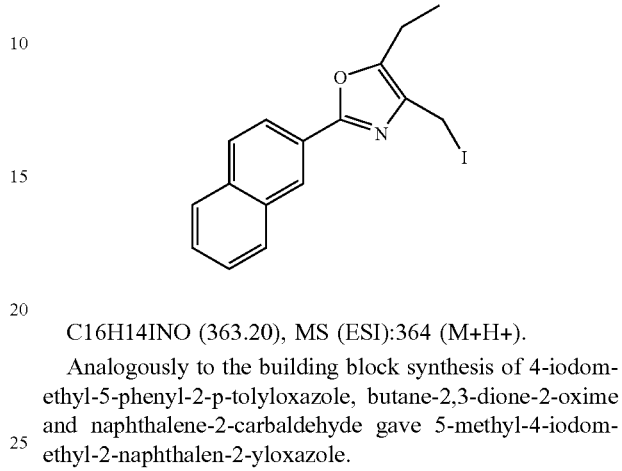

C16H14INO (363.20), MS (ESI):364 (M+H+).

Analogously to the building block synthesis of 4-iodomethyl-5-phenyl-2-p-tolyloxazole, butane-2,3-dione-2-oxime and naphthalene-2-carbaldehyde gave 5-methyl-4-iodomethyl-2-naphthalen-2-yloxazole.

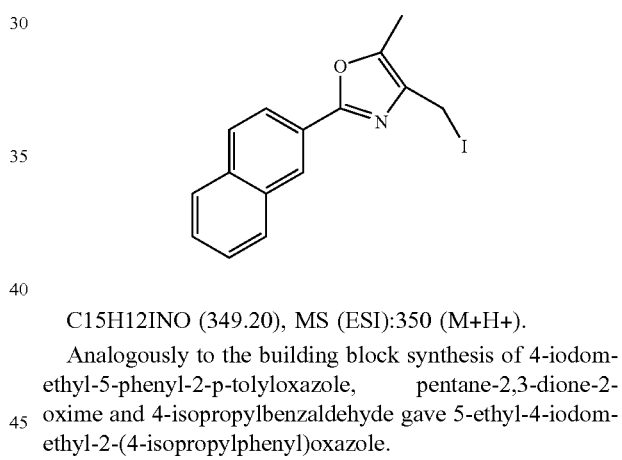

C15H12INO (349.20), MS (ESI):350 (M+H+).

Analogously to the building block synthesis of 4-iodomethyl-5-phenyl-2-p-tolyloxazole, pentane-2,3-dione-2-oxime and 4-isopropylbenzaldehyde gave 5-ethyl-4-iodomethyl-2-(4-isopropylphenyl)oxazole.

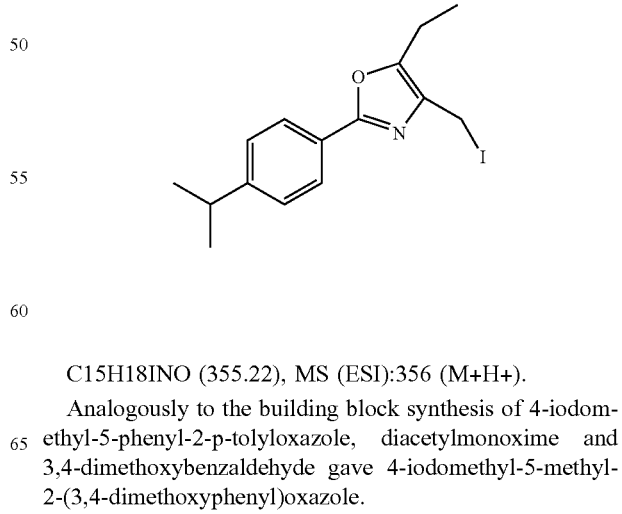

C15H18INO (355.22), MS (ESI):356 (M+H+).

Analogously to the building block synthesis of 4-iodomethyl-5-phenyl-2-p-tolyloxazole, diacetylmonoxime and 3,4-dimethoxybenzaldehyde gave 4-iodomethyl-5-methyl-2-(3,4-dimethoxyphenyl)oxazole.

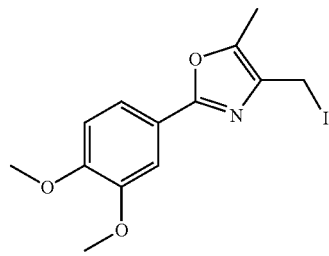
C13H14INO3 (359.17), MS (ESI): 360 (M+H+).
All substances described below have the cis-configuration on the cyclohex-1,3-ylene.
EXAMPLE 1
2-[cis-3-(5-Methyl-2-p-tolyloxazol-4-ylmethoxy)cyclohexylmethoxy]-pentanoic acid
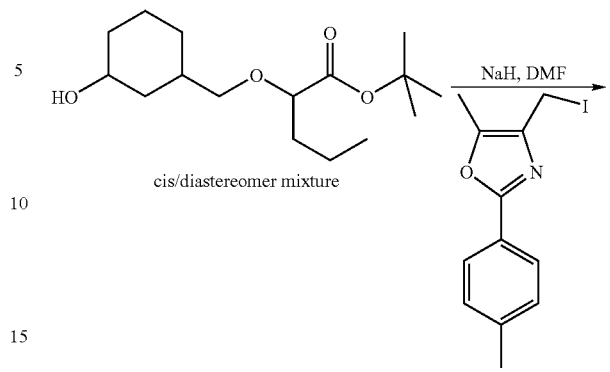
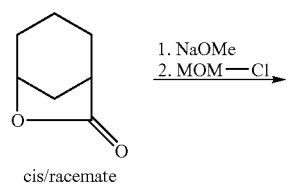
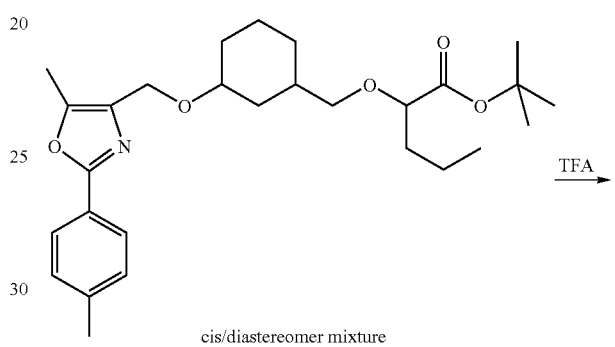
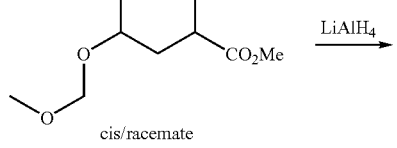
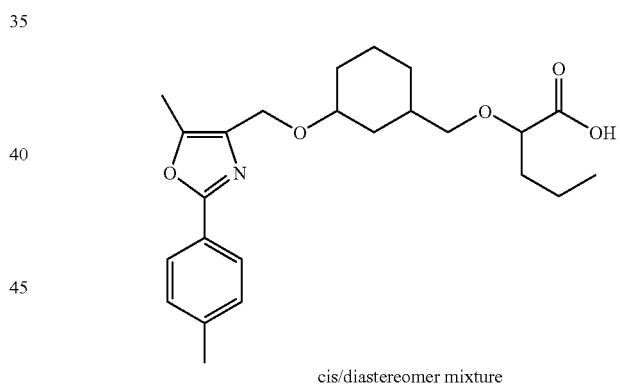
Methyl cis-3-(methoxymethoxy)cyclohexanecarboxylate
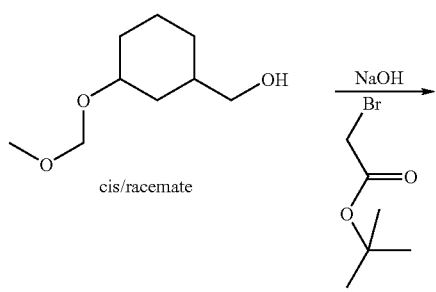
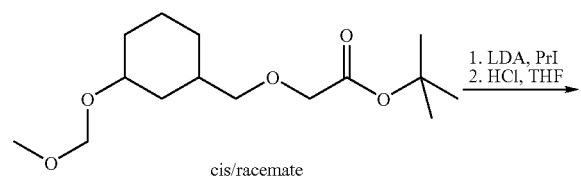
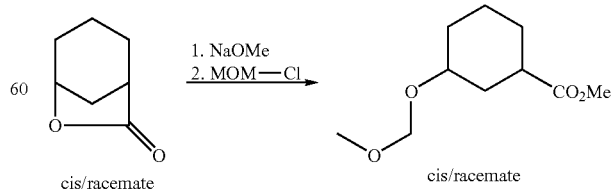

15 g of 6-oxabicyclo[3.2.1]octan-7-one are dissolved in 150 ml of methanol, 13 g of sodium methoxide are added and the mixture is stirred at room temperature for 2 h. 13.7 ml of glacial acetic acid are then added, and most of the solvent is distilled off under reduced pressure. The residue is taken up in water and extracted three times with in each case 100 ml of ethyl acetate. The organic phases are dried over MgSO4 and then concentrated under reduced pressure. This gives 18.8 g of the methyl ester as a colorless oil. This is dissolved in 150 ml of dichloromethane, 19.2 g of methoxymethyl chloride and 23.2 g of diisopropylethylamine are added and the mixture is stirred at room temperature for 15 h. 250 ml of saturated NH4Cl solution and 200 ml of water are added to the solution, and the organic phase is separated off. The aqueous phase is extracted with dichloromethane and the combined organic phases are dried over magnesium sulfate and concentrated. This gives 22.2 g of methyl cis-3-(methoxymethoxy)cyclohexanecarboxylate as a yellow oil. C10H18O4 (202), MS (ESI): 203 (MH+).

cis-(3-Methoxymethoxycyclohexyl)methanol

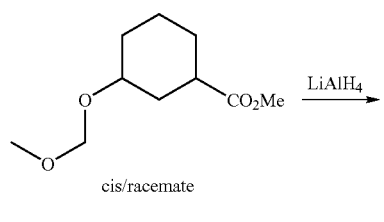

cis/racemate 9.0 g of methyl cis-3-methoxymethoxycyclohexanecarboxylate are dissolved in 280 ml of diethyl ether, 2.2 g of LiAlH4 are added and the mixture is stirred at room temperature. After 4 h, at 0° C., 10 ml of ethyl acetate and then 15 ml of 10N NaOH are added dropwise. The suspension is stirred for 1 h, MgSO4 is added, the mixture is filtered through Celite and the filtrate is concentrated, giving 7.0 g of (cis-3-methoxymethoxycyclo-hexyl)methanol as a colorless oil. C9H18O3 (174), MS(ESI): 175 (MH+).

tert-Butyl (cis-3-methoxymethoxycyclohexylmethoxy)acetate

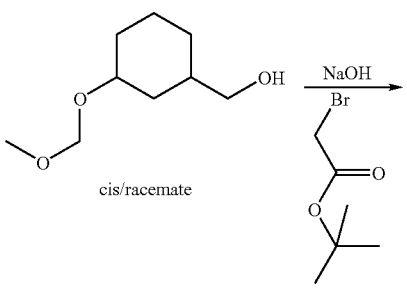

cis/racemate

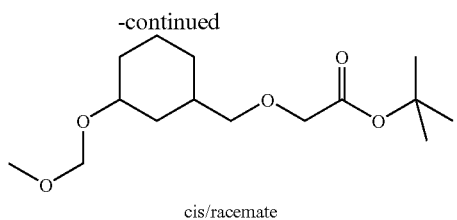

cis/racemate 1.0 g of (cis-3-methoxymethoxycyclohexyl)methanol and 3.3 g of tert-butylbromoacetate are dissolved in 30 ml of toluene, and 0.50 g of tetrabutylammonium hydrogensulfate is added. The suspension is cooled to 10° C. 10 ml of 50% strength NaOH are added to the suspension. The mixture is allowed to warm to room temperature, and after 3 h the aqueous phase is removed and extracted with methyl tert-butyl ether. The combined organic phases are dried over MgSO4 and concentrated. Flash column chromatography on silica gel (heptane/ethyl acetate 10/1->2/1) gives 1.10 g of tert-butyl (cis-3-methoxymethoxycyclohexylmethoxy)acetate as a colorless oil. C15H28O5 (288), LCMS(ESI): 306 (M++H2O).

tert-Butyl 2-(cis-3-hydroxycyclohexylmethoxy)pentanoate

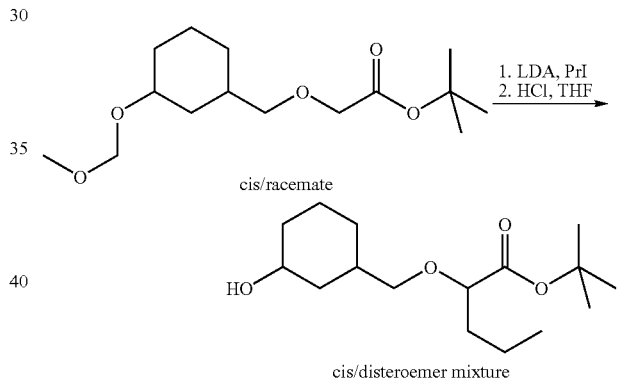

cis/disteroemer mixture 200 mg of tert-butyl (cis-3-methoxymethoxycyclohexylmethoxy)acetate are dissolved in 5 ml of abs. tetrahydrofuran and cooled to −78° C. (dry ice/acetone bath). 0.7 ml of a 2M lithium diisopropylamide solution in tetrahydrofuran/hexane is then added dropwise. The solution is initially stirred at −78° C. and then warmed to 0° C. (ice bath) and stirred at this temperature for 20 min. 600 mg of propyl iodide in 2 ml of tetrahydrofuran are then added, and the solution is stirred at 0° C. for a further 2.5 h. 15 ml of a saturated ammonium chloride solution are added, and the phases are separated. The aqueous phase is extracted with methyl tert-butyl ether. The combined organic phases are dried over MgSO4 and concentrated (yield: 240 mg of crude product). The residue is taken up in 2 ml of tetrahydrofuran, 0.5 ml of conc. HCl is added and the mixture is stirred at room temperature for 18 h. The mixture is diluted with water and methyl tert-butyl ether, the phases are separated and the aqueous phase is extracted with methyl tert-butyl ether. The combined organic phases are washed with saturated NaCl solution, dried over MgSO4 and concentrated. This gives 130 mg of tert-butyl 2-(cis-3-hydroxycyclohexylmethoxy)-pentanoate as a yellow oil. NMR (CDCl3) diastereomer mixture: 3.55-3.67 (m, 2H), 3.41-3.48 (m, 1H), 3.07-3.18 (m, 1H), 1.91-2.13 (m, 2H), 1.11-1.82 (m, 14H), 1.48 (s, 9H).

tert-Butyl 2-[cis-3-(5-methyl-2-p-tolyloxazol-4-yl-methoxy)cyclohexyl-methoxy]pentanoate

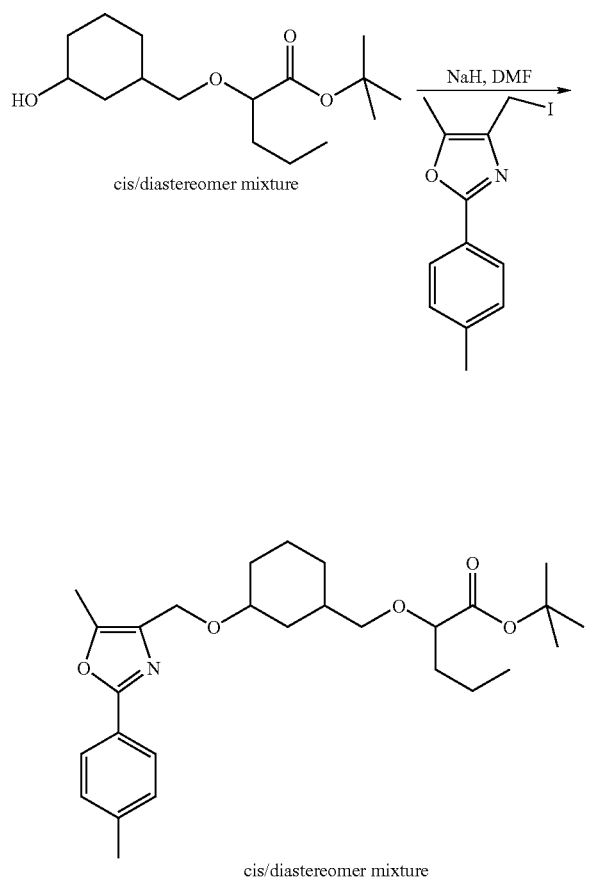

130 mg of tert-butyl 2-(cis-3-hdyroxycyclohexyl-methoxy)pentanoate are dissolved in 3 ml of dimethylformamide, and 20 mg of NaH (95%) are added. After 60 min of stirring, 350 mg of 5-methyl-2-p-tolyloxazol-4-yl-methyl iodide in 1 ml of dimethylformamide are added at 0° C. The mixture is stirred at room temperature for 2 h. 10 ml of methyl tert-butyl ether, 5 ml of water and 10 ml of saturated NaCl solution are then added. The phases are separated, the aqueous phase is extracted once with methyl tert-butyl ether and the organic phases are dried over MgSO4 and concentrated. The residue is chromatographed on silica gel (heptane/ethyl acetate 99/1->10/1). This gives 20 mg of the crude tert-butyl 2-[cis-3-(5-methyl-2-p-tolyloxazol-4-ylmethoxy)cyclohexylmethoxy]pentanoate as a yellow oil. C28H41NO5 (471), LCMS (ESI): 472 (MH+).

2-[cis-3-(5-Methyl-2-p-tolyloxazol-4-ylmethoxy)cyclohexylmethoxy]-pentanoic Acid

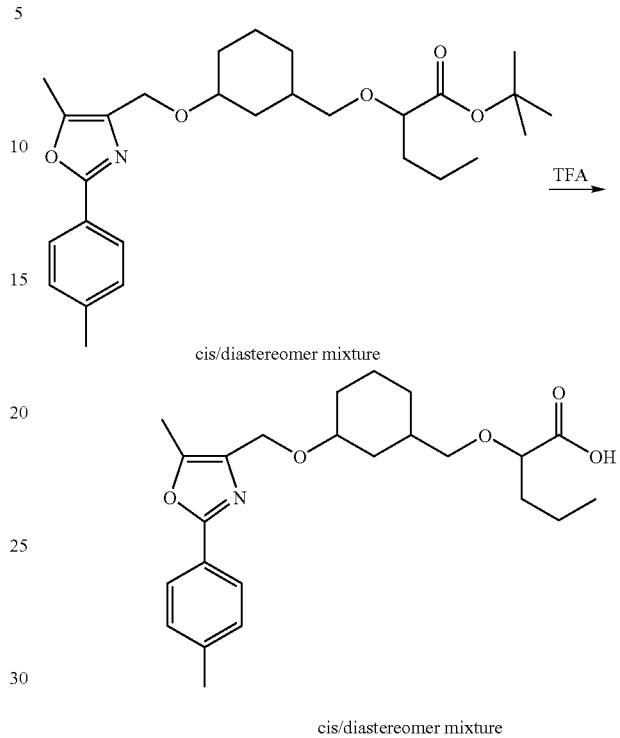

20 mg of tert-butyl 2-[cis-3-(5-methyl-2-p-tolyloxazol-4-ylmethoxy)cyclo-hexylmethoxy]pentanoate are stirred in 1 ml of trifluoroacetic acid overnight. The solution is concentrated completely and purified by HPLC, giving 15 mg of 2-[cis-3-(5-methyl-2-p-tolyloxazol-4-methoxy)cyclohexyl-methoxy]pentanoic acid 7. C24H33NO5 (415), MS(ES+) 416 (MH+).

EXAMPLE 2

Analogously to Example 1, tert-butyl (cis-3-methoxymethoxycyclohexyl-methoxy)acetate, methyl iodide and 5-methyl-2-p-tolyloxazol-4-ylmethyl iodide give 2-[cis-3-(5-methyl-2-p-tolyloxazol-4-ylmethoxy)cyclohexyl-methoxy]propionic acid. C22H29NO5 (387), LCMS(ES+) 388 (MH+).

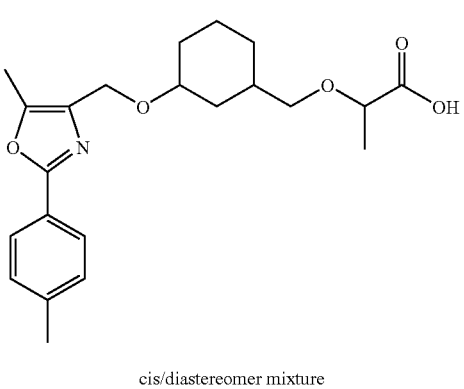

EXAMPLE 3

Analogously to Example 1, tert-butyl (cis-3-methoxymethoxycyclohexyl-methoxy)acetate, ethyl iodide and 5-methyl-2-p-tolyloxazol-4-ylmethyl iodide give 2-[3-(5-methyl-2-p-tolyloxazol-4-ylmethoxy)cyclohexylmethoxy]-butyric acid.

C23H31NO5 (401), LCMS(ES+) 402 (MH+).

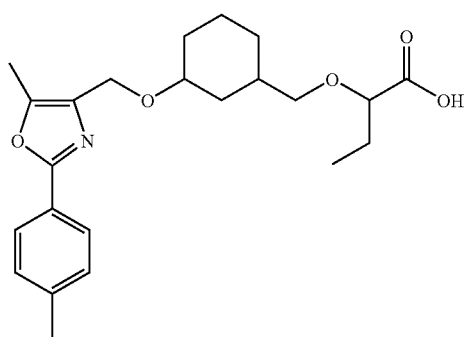

cis/diastereomer mixture

EXAMPLE 4

Analogously to Example 1, tert-butyl (cis-3-methoxymethoxycyclohexyl-methoxy)acetate, benzyl bromide and 5-methyl-2-p-tolyloxazol-4-ylmethyl iodide give 2-[cis-3-(5-methyl-2-p-tolyloxazol-4-ylmethoxy)cyclohexyl-methoxy]-3-phenylpropionic acid. C28H33NO5 (463), LCMS(ES+) 464 (MH+).

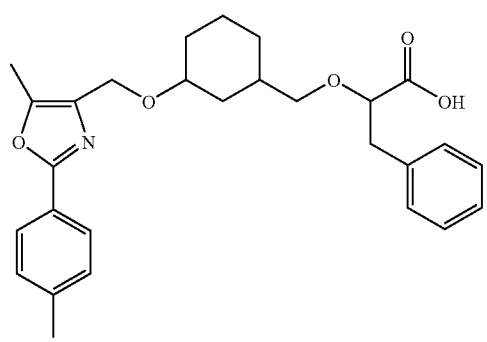

cis/diastereomer mixture

EXAMPLE 5

Analogously to Example 1, tert-butyl (cis-3-methoxymethoxycyclohexyl-methoxy)acetate, methyl iodide and 5-methyl-2-(3-methoxyphenyl)oxazol-4-ylmethyl iodide give 2-[cis-3-(5-methyl-2-(3-methoxyphenyl)oxazol-4-ylmethoxy)cyclohexylmethoxy]propionic acid. C22H29NO6 (403), LCMS(ES+) 404(MH+).

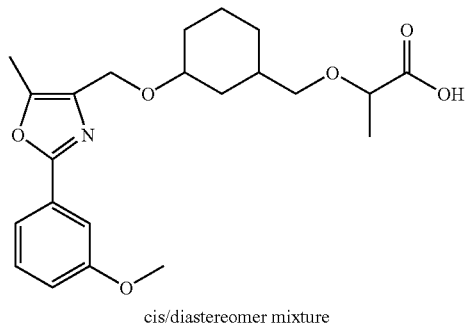

cis/diastereomer mixture

EXAMPLE 6

Analogously to Example 1, tert-butyl cis-(3-methoxymethoxycyclohexyl-methoxy)acetate, methyl iodide and 5-methyl-2-m-tolyloxazol-4-ylmethyl iodide give 2-[cis-3-(5-methyl-2-m-tolyloxazol-4-ylmethoxy)cyclohexyl-methoxy]propionic acid. C23H31NO5 (401), LCMS(ES+) 402 (MH+).

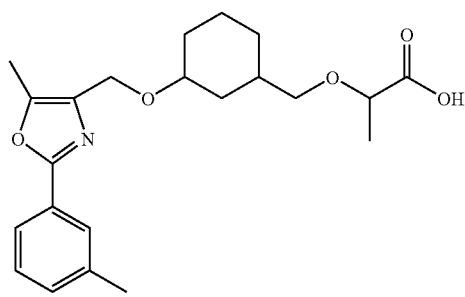

cis/diastereomer mixture

EXAMPLE 7

Analogously to Example 1, tert-butyl cis-(3-methoxymethoxycyclohexyl-methoxy)acetate, methyl iodide and 5-methyl-2-(3-trifluoromethylphenyl)-oxazol-4-ylmethyl iodide give 2-[cis-3-(5-methyl-2-(3-trifluoromethylphenyl)-oxazol-4-ylmethyl)cyclohexylmethoxy]propionic acid. C22H26F3NO5 (441), LCMS(ES+) 442 (MH+).

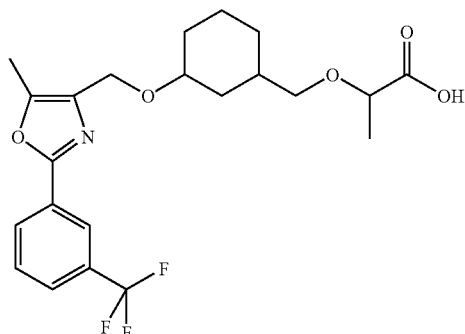

cis/diastereomer mixture

EXAMPLE 8

2-[cis-3-(5-Methyl-2-p-tolyloxazol-4-ylmethoxy)cyclohexylmethoxy]-2-methylpropionic Acid

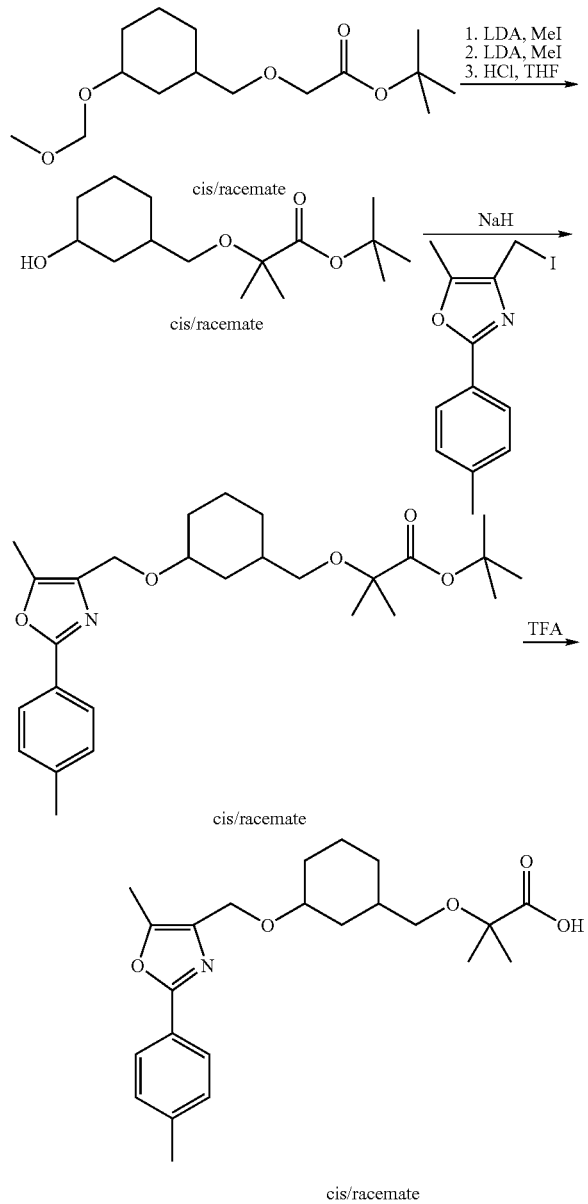

tert-Butyl 2-(cis-3-hydroxycyclohexylmethoxy)-2-methylpropionate

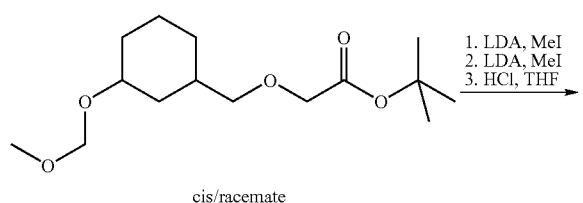

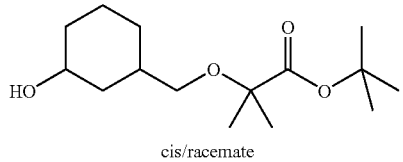

300 mg of tert-butyl (cis-3-methoxymethoxycyclohexylmethoxy)acetate are dissolved in 5 ml of abs. tetrahydrofuran and cooled to −78° C. (dry ice/acetone bath). 1.5 ml of a 2M lithium diisopropyl amide solution in tetrahydrofuran/hexane are then added dropwise. The solution is initially stirred at −78° C. for 90 min and then warmed to 0° C. (ice bath), 1.41 g of methyl iodide and 1.5 ml of tetrahydrofuran are added and the solution is stirred at 0° C. for 1 h. 1 ml of HCl (conc.) is added, and the phases are separated. The aqueous phase is extracted with ethyl acetate. The combined organic phases are dried over MgSO4 and concentrated (yield: 320 mg of crude product). The crude product is dissolved in 5 ml of abs. tetrahydrofuran and cooled to −78° C. (dry ice/acetone bath). 1.5 ml of a 2M lithium diisopropylamide solution in tetrahydrofuran/hexane are then added dropwise. The solution is initially stirred at −78° C. for 90 min and then warmed to 0° C. (ice bath), 1.41 g of methyl iodide and 1.5 ml of tetrahydrofuran are added and the solution is stirred at 0° C. for 1 h. 1 ml of HCl (conc.) is added, and the phases are separated. The aqueous phase is extracted with ethyl acetate. The combined organic phases are dried over MgSO4 and concentrated (yield: 350 mg of crude product). The residue is taken up in 1 ml of tetrahydrofuran, 1 ml of conc. HCl is added and the mixture is stirred at room temperature for 3 d. The mixture is diluted with water and ethyl acetate, the phases are separated and the aqueous phase is extracted with ethyl acetate. The combined organic phases are washed with saturated NaCl solution, dried over MgSO4 and concentrated. The residue is chromatographed on silica gel (heptane/ethyl acetate 2/1), giving 200 mg of tert-butyl 2-(cis-3-hydroxycyclohexylmethoxy)-2-methyl-propionate as a yellow oil. C15H28O4 (272.20), MS(ESI): 273.4 (MH+).

tert-Butyl 2-[cis-3-(5-methyl-2-p-tolyloxazol-4-ylmethoxy)cyclohexyl-methoxy]-2-methylpropionate

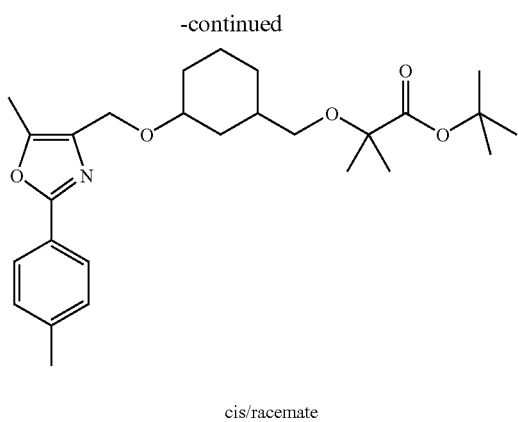

cis/racemate 200 mg of tert-butyl 2-(cis-3-hydroxycyclohexyl-methoxy)-2-methyl-propionate are dissolved in 5 ml of dimethylformamide, and 20 mg of NaH (95%) are added. After 60 min of stirring at room temperature, 460 mg of 5-methyl-2-p-tolyloxazol-4-ylmethyl iodide in 1.5 ml of dimethylformamide are added at 0° C. The mixture is stirred at room temperature for 2 h. 10 ml of methyl tert-butyl ether and 10 ml of saturated NH4Cl solution are then added. The phases are separated, the aqueous phase is extracted once with methyl tert-butyl ether and the organic phases are dried over MgSO4 and concentrated. The residue is chromatographed on silica gel (heptane/ethyl acetate 5/1->1/1). 200 mg of the crude tert-butyl 2-[cis-3-(5-methyl-2-p-tolyloxazol-4-ylmethoxy)cyclohexylmethoxy]-2-methylpropionate are obtained as a yellow oil. C27H39NO5 (457), LCMS (ESI): 458 (MH+).

Improved synthesis of tert-butyl 2-[cis-3-(5-methyl-2-p-tolyloxazol-4-yl-methoxy)cyclohexylmethoxy]-2-methylpropionate

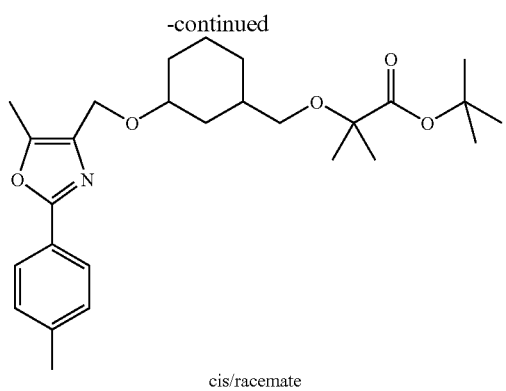

cis/racemate 50 mg of tert-butyl 2-(cis-3-hydroxycyclohexylmethoxy)-2-methylpropionate are dissolved in 0.5 ml of dimethylformamide and 22 mg of NaH (60%) are added. After 30 min of stirring, 112 mg of 5-methyl-2-p-tolyloxazol-4-yl-methyl iodide are added at room temperature. The mixture is placed in an ultrasonic bath for 10 min and then stirred at room temperature for 3 h. 10 ml of methyl tert-butyl ether and 10 ml of water are then added. The phases are separated, the aqueous phase is extracted once with methyl tert-butyl ether and the organic phases are dried over MgSO4 and concentrated. The residue is chromatographed on silica gel (heptane/ethyl acetate 5/1->1/1). 60 mg of the crude tert-butyl 2-[cis-3-(5-methyl-2-p-tolyloxazol-4-ylmethoxy)cyclohexylmethoxy]-2-methylpropionate are obtained as a yellow oil. C27H39NO5 (457), LCMS(ESI): 458 (MH+).

2-[cis-3-(5-Methyl-2-p-tolyloxazol-4-ylmethoxy)cyclohexylmethoxy]-2-methylpropionic Acid

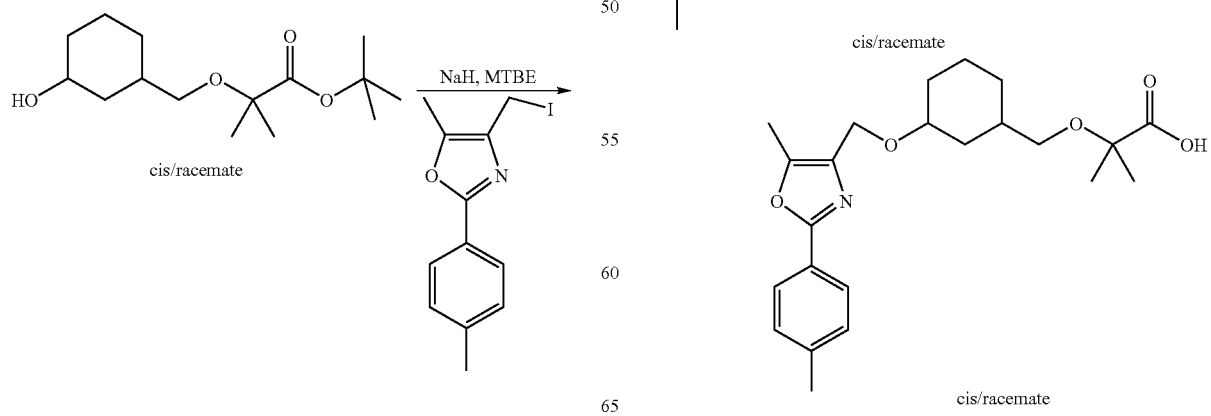

200 mg of tert-butyl 2-[cis-3-(5-methyl-2-p-tolyloxazol-4-ylmethoxy)cyclo-hexylmethoxy]-2-methylpropionate are stirred in 2 ml of trifluoroacetic acid for 1 h. The solution is concentrated completely and purified by flash chromatography (heptane/ethyl acetate 5/1) giving 66 mg of 2-[cis-3-(5-methyl-2-p-tolyloxazol-4-ylmethoxy)cyclohexylmethoxy]-2-methylpropionic acid.

C23H31NO5 (401.51), MS(ES+) 402.29 (MH+).

EXAMPLE 8a

2-[(1R,3S)-3-(5-Methyl-2-p-tolyloxazol-4-ylmethoxy)cyclohexylmethoxy]-2-methylpropionic Acid

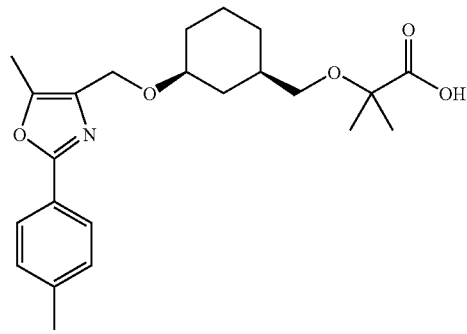

Starting with an enantiomerically pure tert-butyl 2-[(1R,3S)-cis-3-hydroxy-cyclohexylmethoxy]-2-methylpropionate, 2-[(1R,3S)-cis-3-(5-methyl-2-p-tolyloxazol-4-ylmethoxy)cyclohexylmethoxy]-2-methylpropionic acid is obtained. C23H31NO5 (401.51), MS(ES+) 402.29 (MH+).

EXAMPLE 9

1-[cis-3-(5-Methyl-2-p-tolyloxazol-4-ylmethoxy)cyclohexylmethoxy]cyclo-pentanecarboxylic acid

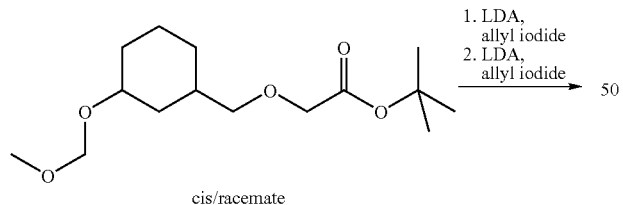

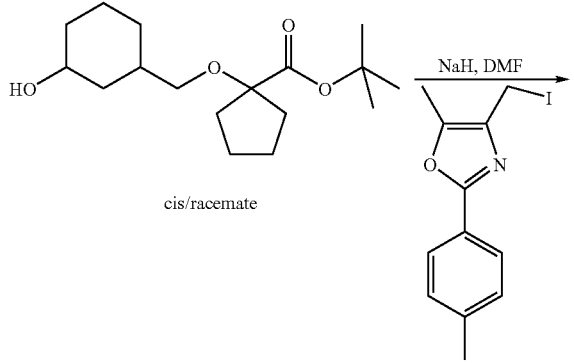

tert-Butyl 2-allyl-2-(cis-3-methoxymethoxycyclohexylmethoxy)pent-4-enoate

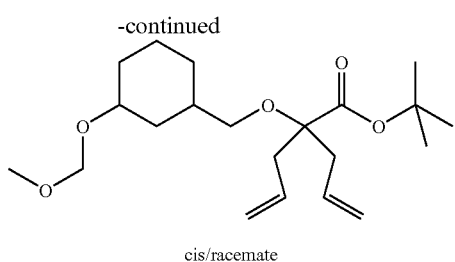

cis/racemate 200 mg of tert-butyl (cis-3-methoxymethoxycyclohexyl-methoxy)acetate are dissolved in 6 ml of abs. tetrahydrofuran and cooled to −78° C. (dry ice/acetone bath). 1.05 ml of a 2M lithium diisopropylamide solution in tetrahydrofuran/hexane are then added dropwise. The solution is initially stirred at −78° C. and then at 0° C., in each case for 20 min, and 0.85 g of allyl bromide in 1.5 ml of tetrahydrofuran is added at 0° C. The solution is stirred at 0° C. for 30 min. 1 ml of a saturated NH4Cl solution and 5 ml of ethyl acetate are added and the phases are separated. The aqueous phase is extracted with ethyl acetate. The combined organic phases are dried over MgSO4 and concentrated. The residue is chromatographed on silica gel (heptane/ethyl acetate 10/1), giving 160 mg of monoallylated product. This is dissolved in 6 ml of abs. tetrahydrofuran and cooled to −78° C. (dry ice/acetone bath). 1.05 ml of a 2M lithium diisopropylamide solution in tetrahydrofuran/hexane are then added dropwise. The solution is initially stirred at −78° C. and then at 0° C., in each case for 20 min, and 0.85 g of allyl bromide in 1.5 ml of tetrahydrofuran is added at 0° C. The solution is stirred at 0° C. for 2 h. 1 ml of a saturated NH4Cl solution and 5 ml of ethyl acetate are added and the phases are separated. The aqueous phase is extracted with ethyl acetate. The combined organic phases are dried over MgSO4 and concentrated. The residue is chromatographed on silica gel (heptane/ethyl acetate 5/1), giving 140 mg of tert-butyl 2-allyl-2-(cis-3-methoxymethoxycyclohexylmethoxy)pent-4-enoate as a yellow oil. $C_{21}H_{36}O_5$ (368.52), MS(ESI): 296.25 ($MH^+$−C4H9O).

tert-Butyl (cis-3-hydroxycyclohexylmethoxy)cyclopentanecarboxylate

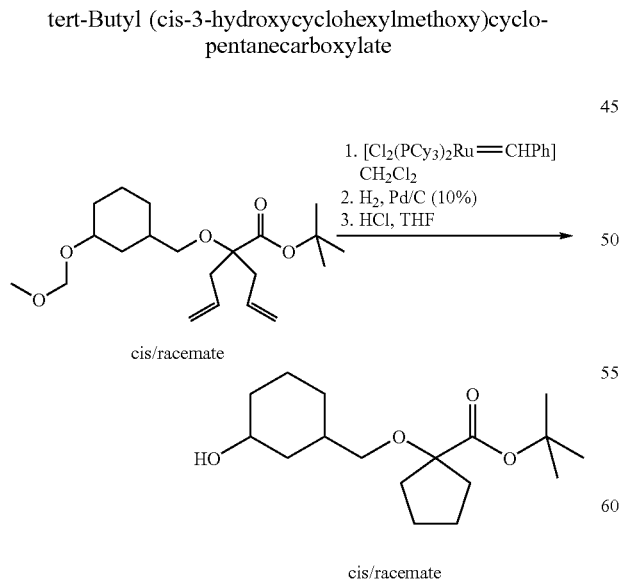

cis/racemate 140 mg of tert-butyl 2-allyl-2-(cis-3-methoxymethoxycyclohexylmethoxy)pent-4-enoate are dissolved in 5 ml of dichloromethane, 10 mg of Grubbs catalyst ($Cl_2(Cy_3P)_2Ru$=CHPh) are added under an Ar atmosphere and the mixture is stirred at 40° C. for 48 h. 10 ml of heptane/ethyl acetate (3/1) are added and the solution is filtered through silica gel. This gives 100 mg of tert-butyl 1-(cis-3-methoxymethoxy-cyclohexylmethoxy)cyclopent-3-enecarboxylate as a brown oil. This is dissolved in 2 ml of MeOH, degassed and saturated with Ar. 30 mg of Pd/C (10%) are then added, and the mixture is degassed again. The solution is saturated with hydrogen and stirred at room temperature overnight. Dilution with 20 ml of ethyl acetate and filtration through Celite give 100 mg of crude tert-butyl 1-(cis-3-methoxymethoxycyclohexylmethoxy)cyclopentane-carboxylate. This is taken up in 2 ml of tetrahydrofuran, 0.5 ml of HCl (conc.) is added and the mixture is stirred at room temperature overnight. The solution is neutralized with saturated NaHCO3 solution and extracted three times with ethyl acetate. The organic phases are dried over MgSO4 and concentrated. Chromatography of the residue on silica gel (heptane/ethyl acetate 10/1->1/1) gives 57 mg of tert-butyl 1-(cis-3-hydroxycyclohexylmethoxy)cyclopentanecarboxylate as a yellow oil. For the next step, this is used in crude form.

tert-Butyl 1-[cis-3-(5-methyl-2-p-tolyloxazol-4-yl-methoxy)cyclohexyl-methoxy]cyclopentanecarboxylate 57 mg of tert-butyl 1-(cis-3-hydroxycyclohexylmethoxy)cyclopentane-carboxylate are dissolved in 3 ml of dimethylformamide, and 10 mg of NaH are added. The suspension is stirred at room temperature for 30 min and then cooled to 0° C., and 150 mg of methyl 2-p-tolyloxazol-4-ylmethyl iodide in 1 ml of dimethylformamide are added dropwise. The suspension is stirred at room temperature for 2 h and diluted with methyl tert-butyl ether and saturated NaCl solution. The aqueous phase is removed and extracted with methyl tert-butyl ether. The combined organic phases are washed with saturated NaCl solution, dried over MgSO4 and concentrated. Chromato-graphy of the residue on silica gel (heptane/ethyl acetate 99/–>10/1) gives 20 mg of a product mixture which, according to LCMS, contains the desired tert-butyl 1-[cis-3-(5-methyl-2-p-tolyloxazol-4-yl-methoxy)cyclohexyl-methoxy]cyclopentanecarboxylate. This mixture is used for the next step, without further purification. C29H41NO5 (483.65), LCMS (ESI): 484.2 (MH+).

1-[cis-3-(5-Methyl-2-p-tolyloxazol-4-ylmethoxy) cyclohexylmethoxy]cyclo-pentanecarboxylic acid

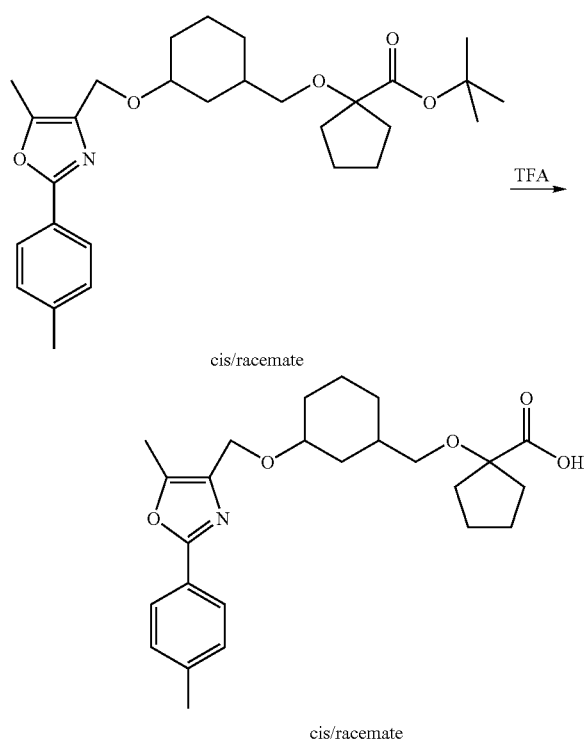

20 mg of impure tert-butyl 1-[cis-3-(5-methyl-2-p-toly-loxazol-4-ylmethoxy)-cyclohexylmethoxy]cyclopentan-ecarboxylate is stirred in 1 ml of trifluoroacetic acid at room temperature overnight. The solution is concentrated completely and the residue is chromatographed on silica gel (heptane/ethyl acetate 10/1->1/1->methyl tert-butyl ether), giving 7.5 mg of 1-[cis-3-(5-methyl-2-p-tolyloxazol-4-yl-methoxy)cyclohexylmethoxy]cyclo-pentanecarboxylic acid. C25H33NO5 (427.55); LCMS 428.2 (MH+).

EXAMPLE 10

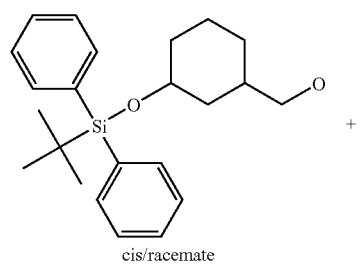

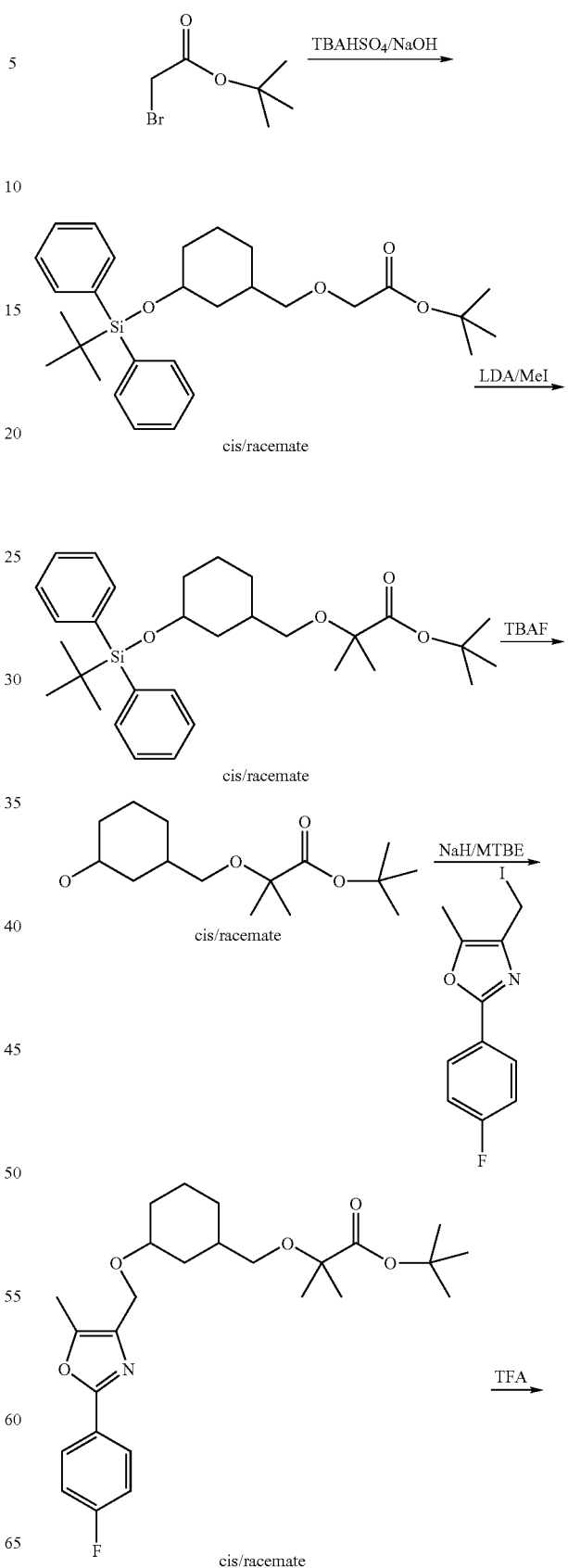

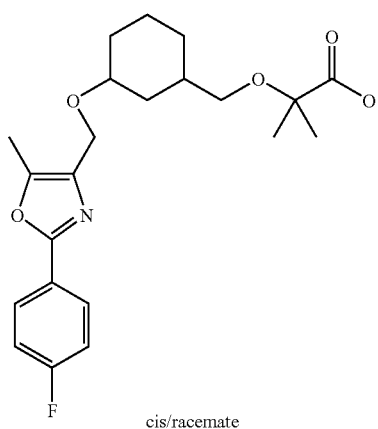

cis/racemate tert-Butyl cis-3-(tert-butyldiphenylsilanyloxy)cyclohexylmethoxy]acetate

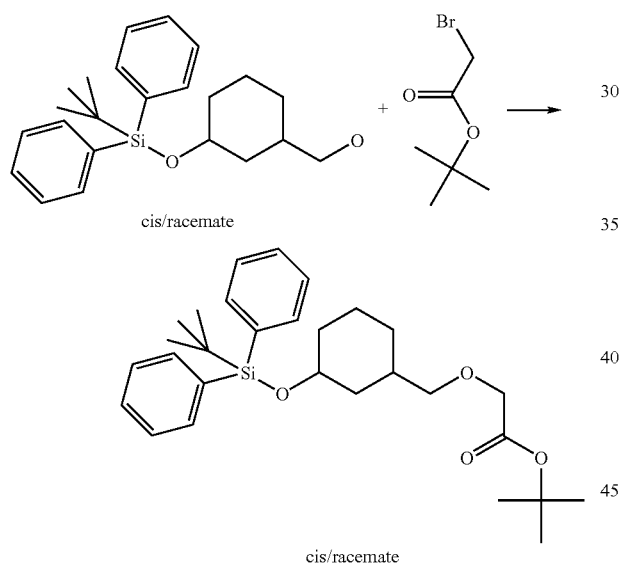

25 g of [cis-3-(tert-butyldiphenylsilanyloxy)cyclohexyl]methanol, together with 40 g of tert-butyl bromoacetate and 6.9 g of tetrabutylammonium hydrogensulfate, are dissolved in 300 ml of toluene, and 200 ml of NaOH (50% strength) are then added dropwise at 0° C. The mixture is stirred at 0° C. for 1 h and then warmed to room temperature. The solvent is removed and the mixture is extracted with 3×100 ml of methyl tert-butyl ether. After the third extraction, the aqueous phase is acidified and once more extracted with 200 ml of methyl tert-butyl ether. The combined organic phases are extracted with saturated sodium chloride solution and dried over magnesium sulfate, and the solvent is removed under reduced pressure. This gives 27.8 g of tert-butyl cis-3-(tert-butyldiphenylsilanyloxy)-cyclohexylmethoxy]acetate as a yellow oil.

$C_{29}H_{42}O_4Si$ (482.74), MS(ESI): 483 (M+H$^+$)

tert-Butyl 2-[cis-3-(tert-butyldiphenylsilanyloxy)cyclohexylmethoxy]-2-methylpropionate

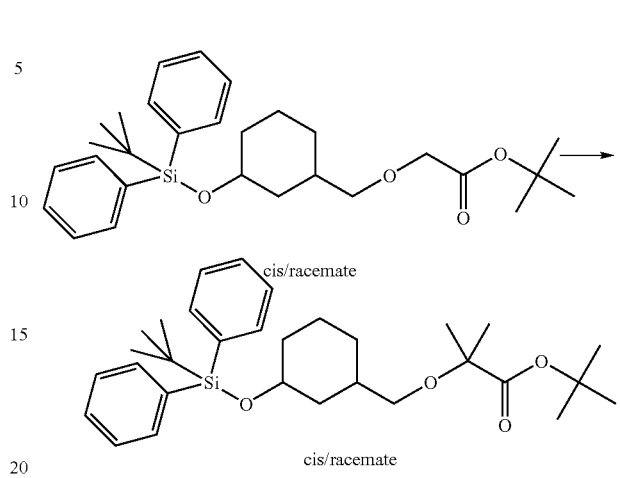

20.0 g of tert-butyl cis-3-(tert-butyldiphenylsilanyloxy)cyclohexylmethoxy]-acetate are initially charged in a 1 l three-necked flask, which had been dried by heating, dissolved in 200 ml of dry tetrahydrofuran and cooled to −78° C., and 83 ml of lithium diisopropylamide (2N in tetrahydrofuran) are slowly added dropwise such that the internal temperature does not exceed −65° C. The mixture is then warmed to 0° C. and stirred for 1 h, during which the color of the solution turns to yellow. The mixture is cooled again to −70° C., 35.27 g of methyl iodide are then added dropwise and the mixture is stirred at 0° C. for 3 h. The reaction is checked (TLC and LCMS), showing the formation of a new product (monomethyl compound). 200 ml of saturated ammonium chloride solution are added to the reaction mixture, and the mixture is extracted with water/methyl tert-butyl ether. This gives the crude product as a dark-red oil which, without purification, is converted in the same reaction sequence into the germinal dimethyl compound. The crude product is purified on silica gel (heptane/ethyl acetate 50:1→10:1). This gives 16 g of tert-butyl 2-[cis-3-(tert-butyl-diphenylsilanyloxy)cyclohexylmethoxy]-2-methylpropionate as a light-yellow oil.

$C_{31}H_{46}O_4Si$ (510.80), MS(ESI): 511 (M+H$^+$).

tert-Butyl 2-(cis-3-hydroxycyclohexylmethoxy)-2-methylpropionate

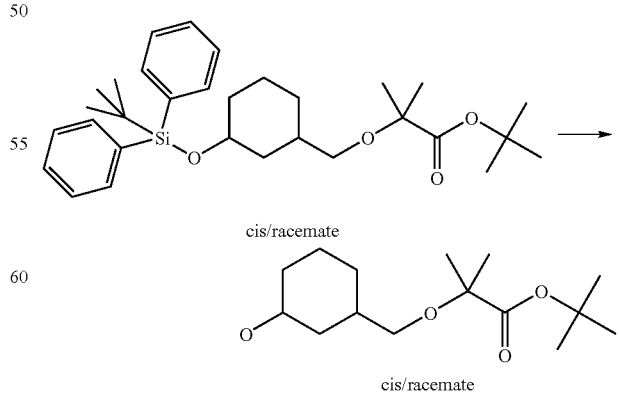

16 g of tert-butyl 2-[cis-3-(tert-butyldiphenylsilanyloxy)cyclohexylmethoxy]-2-methylpropionate are dissolved in 100 ml of acetonitrile, and 62 ml of tetrabutylammonium fluoride (1 N solution in tetrahydrofuran) are added. After 2 h of stirring at 60° C., the reaction has ended and the mixture is concentrated under reduced pressure. The residue is extracted from water/ethyl acetate. The combined org. phases are extracted with saturated sodium chloride solution and dried over magnesium sulfate, and the solvent is removed under reduced pressure. The crude product is purified on silica gel (heptane/ethyl acetate 15:1→1:1). This under reduced pressure and the crude product is then purified by HPLC. This gives 0.08 g of the compound tert-butyl 2-{cis-3-[2-(4-fluorophenyl)-5-methyloxazol-4-ylmethoxy]cyclohexyl-methoxy}-2-methylpropionate as a colorless oil.
$C_{26}H_{36}FNO_5$ (461.58), MS(ESI): 462 (M+H$^+$)

2-{cis-3-[2-(4-Fluorophenyl)-5-methyloxazol-4-ylmethoxy]cyclohexyl-methoxy}-2-methylpropionic acid

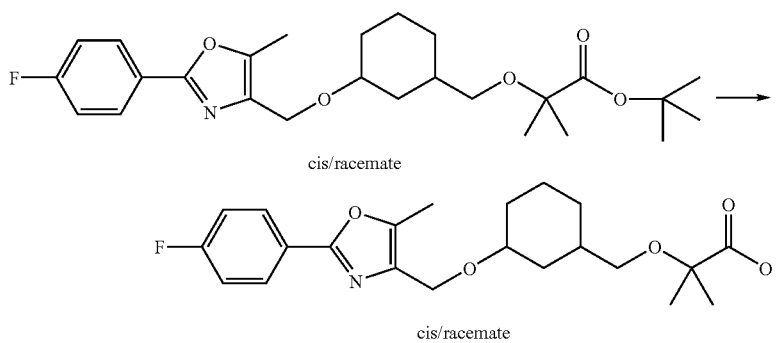

cis/racemate gives 16 g of the product tert-butyl 2-(cis-3-hydroxycyclohexylmethoxy)-2-methylpropionate as a colorless oil.
$C_{15}H_{28}O_4$ (272.39), MS(ESI): 273 (M+H$^+$)

tert-Butyl 2-{cis-3-[2-(4-fluorophenyl)-5-methyloxazol-4-ylmethoxy]cyclo-hexylmethoxy}-2-methyl-propionate

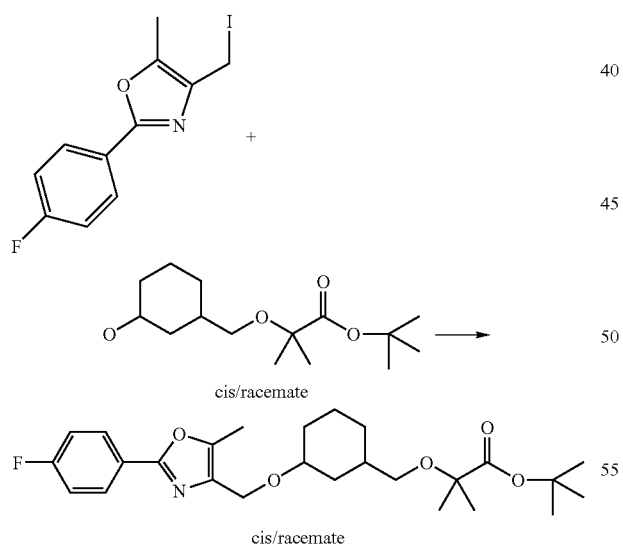

cis/racemate 0.05 g of the alcohol tert-butyl 2-(cis-3-hydroxycyclohexylmethoxy)-2-methylpropionate is dissolved in methyl tert-butyl ether, and 15 mg of sodium hydride are added. After 15 minutes of stirring at room temperature, 0.12 g of 2-(4-fluorophenyl)-4-iodomethyl-5-methyloxazole is added, and the mixture is stirred at room temperature for 12 h. Following addition of 2 ml of 1 N HCl, the product is extracted with ethyl acetate (2×5 ml), the solvent is removed 0.07 g of tert-butyl 2-{cis-3-[2-(4-fluorophenyl)-5-methyloxazol-4-yl-methoxy]cyclohexylmethoxy}-2-methylpropionate is dissolved in 1 ml of dichloromethane, 1 ml of trifluoroacetic acid is added and the mixture is stirred at room temperature. The reaction is monitored (LCMS), showing complete conversion after 30 minutes. The reaction mixture is extracted with water/dichloromethane and, after removal of the solvent under reduced pressure, purified by preparative HPLC. This gives 0.06 g of the carboxylic acid 2-{cis-3-[2-(4-fluorophenyl)-5-methyloxazol-4-yl-methoxy]-cyclohexylmethoxy}-2-methylpropionic acid as a colorless oil.
$C_{22}H_{28}FNO_5$ (405.47), MS(ESI): 406 (M+H$^+$)

EXAMPLE 11

Analogously to Example 10, tert-butyl 2-(cis-3-hydroxycyclohexylmethoxy)-2-methylpropionate and 2-(3-methoxyphenyl)-5-methyloxazol-4-ylmethyl iodide give 2-{(1S,3R)-cis-3-[2-(3-methoxyphenyl)-5-methyloxazol-4-ylmethoxy]cyclohexylmethoxy}-2-methylpropionic acid.

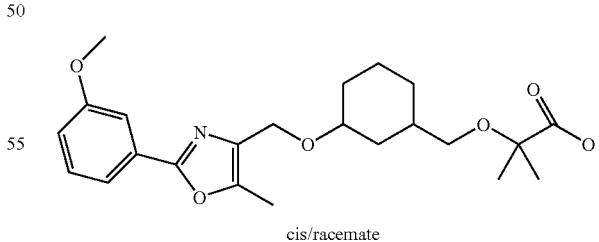

cis/racemate $C_{23}H_{31}NO_6$ (417.50) MS(ESI): 418 (M+H$^+$)

EXAMPLE 12

Analogously to Example 10, tert-butyl 2-(cis-3-hydroxycyclohexylmethoxy)-2-methylpropionate and 2-(3-trifluoromethylphenyl)-5-methyloxazol-4-yl-methyl iodide give 2-{(1S,3R)-3-[2-(cis-3-trifluoromethylphenyl)-5-methyl-oxazol-4-ylmethoxy]cyclohexylmethoxy}-2-methylpropionic acid.

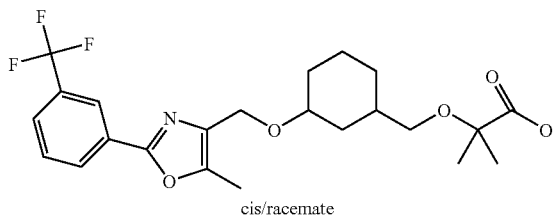

cis/racemate $C_{23}H_{28}F_3NO5$ (455.47) MS(ESI): 456 (M+H$^+$)

EXAMPLE 13

Analogously to Example 10, tert-butyl 2-(cis-3-hydroxy-cyclohexylmethoxy)-2-methylpropionate and 5-methyl-2-(5-methylfuran-2-yl)oxazol-4-ylmethyl iodide give 2-methyl-2-{(1R,3S)-cis-3-[5-methyl-2-(5-methylfuran-2-yl)-oxazol-4-ylmethoxy]cyclohexylmethoxy}propionic acid.

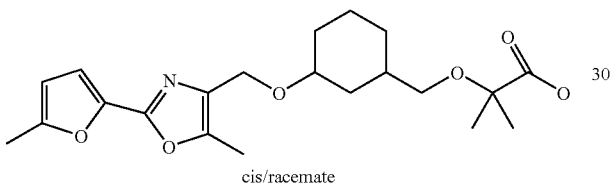

cis/racemate $C_{21}H_{29}NO_6$ (391.46) MS(ESI): 392 (M+H$^+$)

EXAMPLE 14

Analogously to Example 10, tert-butyl 2-(cis-3-hydroxy-cyclohexylmethoxy)-2-methylpropionate and 2-(3,4-dimethoxyphenyl)-5-methyloxazol-4-yl-methyl iodide give 2-{(1R,3S)-cis-3-[2-(3,4-dimethoxyphenyl)-5-methyl-oxazol-4-ylmethoxy]cyclohexylmethoxy}-2-methylpropionic acid.

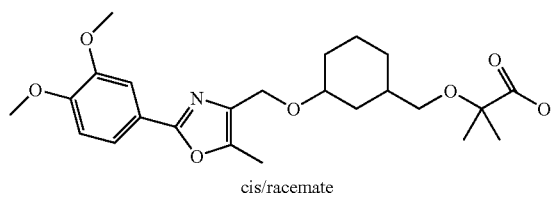

cis/racemate $C_{24}H_{33}NO_7$ (447.53) MS(ESI): 448 (M+H$^+$)

EXAMPLE 15

Analogously to Example 10, tert-butyl 2-(cis-3-hydroxy-cyclohexylmethoxy)-2-methylpropionate and 5-phenyl-2-p-tolyloxazol-4-ylmethyl iodide give 2-methyl-2-[(1R,3S)-cis-3-(5-phenyl-2-p-tolyloxazol-4-ylmethoxy)cyclo-hexylmethoxy]propionic acid.

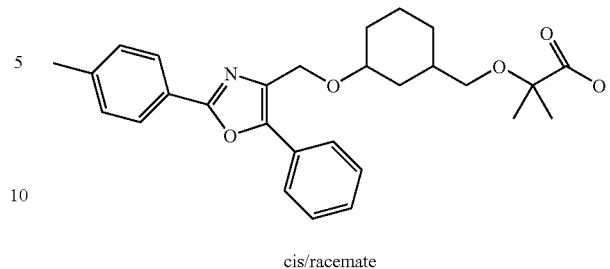

cis/racemate $C_{28}H_{33}NO5$ (463.57) MS(ESI): 464 (M+H$^+$)

EXAMPLE 16

Analogously to Example 10, tert-butyl 2-(cis-3-hydroxy-cyclohexylmethoxy)-2-methylpropionate and 5-methyl-2-(4-trifluoromethylphenyl)oxazol-4-yl-methyl iodide give 2-methyl-2-{(1R,3S)-cis-3-[5-methyl-2-(4-trifluoromethyl-phenyl)oxazol-4-ylmethoxy]cyclohexylmethoxy}propionic acid.

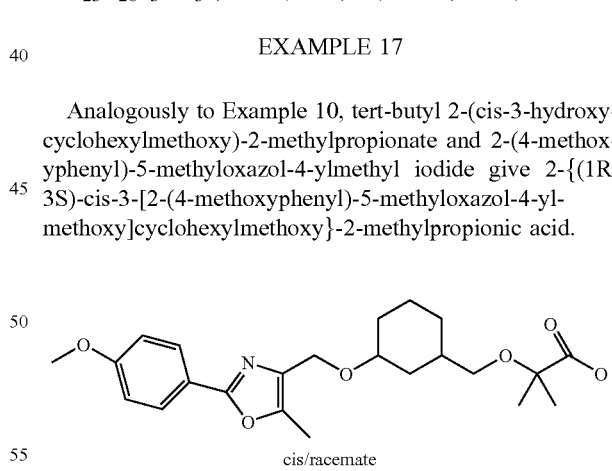

cis/racemate $C_{23}H_{28}F_3NO_5$ (455.47) MS(ESI): 456 (M+H$^+$)

EXAMPLE 17

Analogously to Example 10, tert-butyl 2-(cis-3-hydroxy-cyclohexylmethoxy)-2-methylpropionate and 2-(4-methoxyphenyl)-5-methyloxazol-4-ylmethyl iodide give 2-{(1R,3S)-cis-3-[2-(4-methoxyphenyl)-5-methyloxazol-4-yl-methoxy]cyclohexylmethoxy}-2-methylpropionic acid.

cis/racemate $C_{23}H_{31}NO_6$ (417.50) MS(ESI): 418 (M+H$^+$)

EXAMPLE 18

Analogously to Example 10, tert-butyl 2-(cis-3-hydroxy-cyclohexylmethoxy)-2-methylpropionate and 5-methyl-2-thiophen-2-yloxazol-4-methyl iodide give 2-methyl-2-[(1R,3S)-cis-3-(5-methyl-2-thiophen-2-yloxazol-4-yl-methoxy)cyclohexylmethoxy]propionic acid.

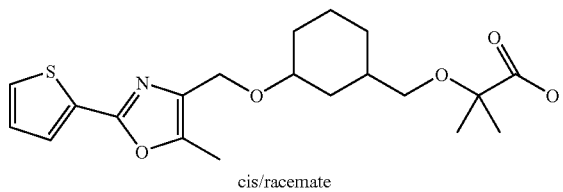

cis/racemate

C$_{20}$H$_{27}$NO$_5$S (393.50) MS(ESI): 394 (M+H$^+$)

EXAMPLE 19

Analogously to Example 10, tert-butyl 2-(cis-3-hydroxy-cyclohexylmethoxy)-2-methylpropionate and-methyl-2-(3-trifluoromethoxyphenyl)oxazol-4-ylmethyl iodide give 2-methyl-2-[(1R,3S)-cis-3-[5-methyl-2-(3-trifluoro-methoxyphenyl)oxazol-4-ylmethoxy]cyclohexylmethoxy]propionic acid.

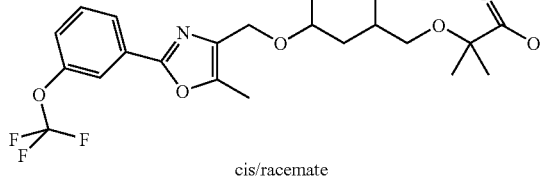

cis/racemate

C$_{23}$H$_{28}$F$_3$NO$_6$ (471.47) MS(ESI): 472 (M+H$^+$)

EXAMPLE 20

Analogously to Example 10, tert-butyl 2-(cis-3-hydroxy-cyclohexylmethoxy)-2-methylpropionate and 5-methyl-2-(4-isopropylphenyl)oxazol-4-ylmethyl iodide give 2-methyl-2-[(1R,3S)-cis-3-(5-methyl-2-(4-isopropylphenyl)-oxazol-4-ylmethoxy)cyclohexylmethoxy]propionic acid.

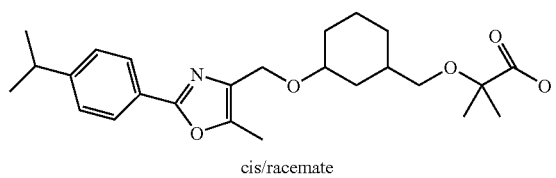

cis/racemate

C$_{25}$H$_{35}$NO$_5$ (429.56) MS(ESI): 430 (M+H$^+$)

EXAMPLE 21

Analogously to Example 10, tert-butyl 2-(cis-3-hydroxy-cyclohexylmethoxy)-2-methylpropionate and 5-methyl-2-m-tolyloxazol-4-ylmethyl iodide give 2-methyl-2-[(1R,3S)-cis-3-(5-methyl-2-m-tolyloxazol-4-ylmethoxy)cyclohexylmethoxy]propionic acid.

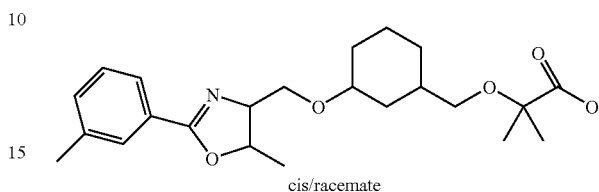

cis/racemate

C$_{25}$H$_{31}$NO$_5$ (401.50) MS(ESI): 402 (M+H$^+$)

EXAMPLE 22 cis-3-(5-Methyl-2-p-tolyloxazol-4-ylmethoxy)cyclohexylmethylsulfanyl]acetic acid

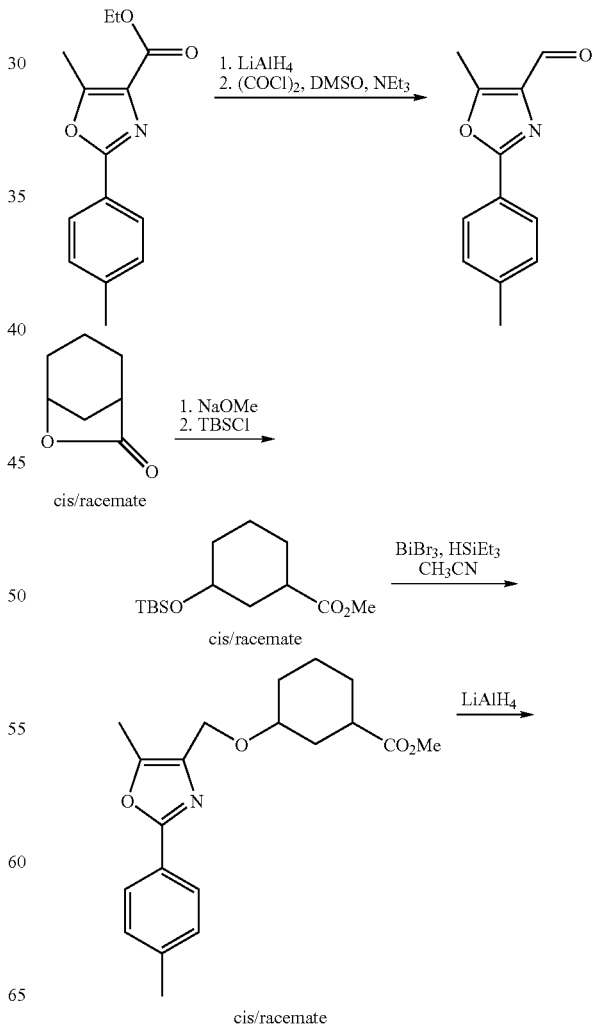

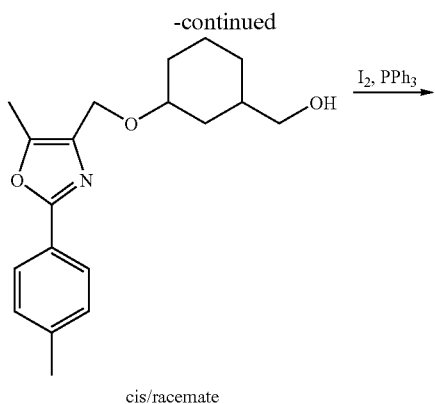

cis/racemate

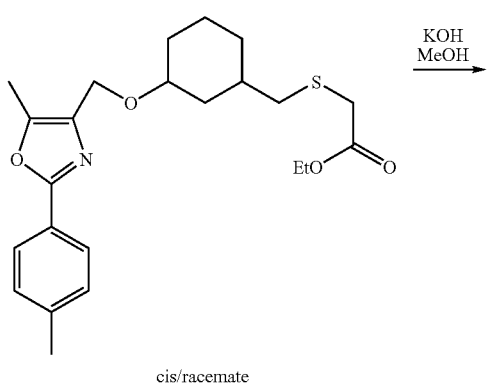

cis/racemate

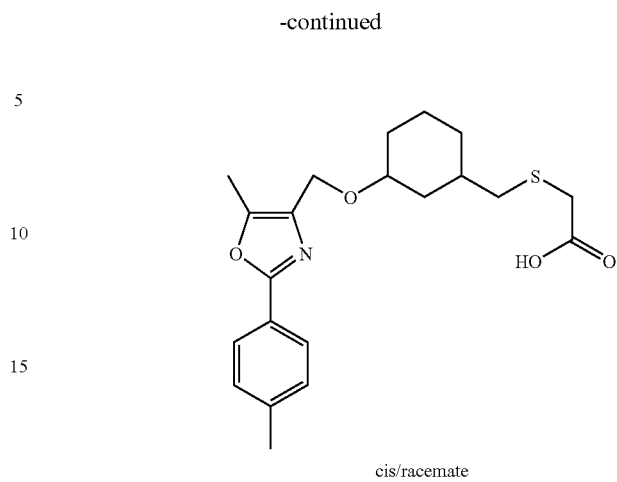

cis/racemate

5-Methyl-2-p-tolyloxazole-4-carboxaldehyde

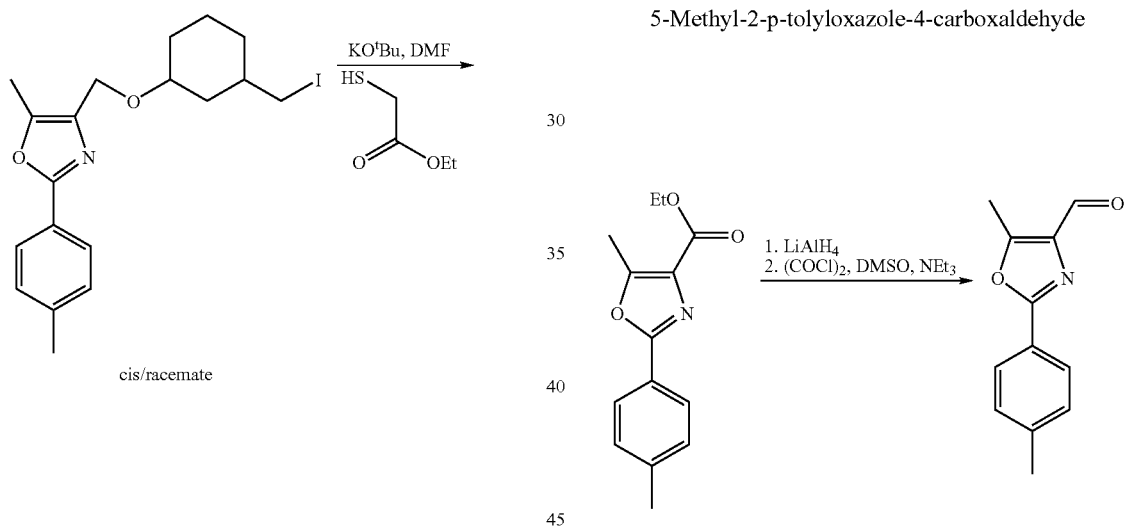

In a dry four-necked flask with stirrer motor, internal thermometer, dropping funnel with pressure equalizer and reflux condenser with argon inlet (aspirator with tap), 9.3 g of LiAlH4 are covered with 600 ml of diethyl ether. The suspension is cooled to 0° C. 30 g of ethyl 5-methyl-2-p-tolyloxazole-4-carboxylate are dissolved in 100 ml of diethyl ether and added dropwise to the suspension. After one hour of stirring at room temperature, the reaction has ended (TLC (heptane/ethyl acetate 1:1): $R_f$, starting material=0.66, $R_{f,\ product}$=0.18). 80 g of MgSO4, 300 ml of methyl tert-butyl ether and 30 ml of ethyl acetate are added successively, and the suspension is stirred at room temperature. The mixture is then cooled to 0° C., 90 ml of 10N KOH are added dropwise and the mixture is stirred for another 60 min. The solids are filtered off, the residue is washed three times with ethyl acetate and the filtrate is concentrated, giving 24 g of 5-methyl-2-p-tolyl-oxazole-4-methanol as a yellow solid. C12H13NO2 (203.24), LCMS(ESI): 204.1 (MH+).

At −78° C., 22.2 ml of DMSO in 30 ml of dichloromethane are added dropwise to a solution of 12 ml of oxalyl chloride in 150 ml of dichloromethane such that the temperature does not exceed −70° C. The solution is then stirred at this temperature for 30 min. 24 g of 5-methyl-2-p-tolyloxazole-4-methanol in 120 ml of dichloromethane/chloroform (2/1) are then added dropwise, the temperature not exceeding −70° C. The solution is stirred at this temperature for 30 min. 80 ml of NEt$_3$ are then added dropwise such that the temperature does not exceed −70° C. After the addition has ended, the cooling bath is removed and the solution is, with stirring, warmed to 0° C. At this temperature, 100 ml of water are added and the mixture is stirred vigorously at room temperature. The aqueous phase is separated off and extracted with chloroform. The combined organic phases are washed with saturated NH$_4$Cl solution, dried over MgSO$_4$ and concentrated, giving 23.8 g of 5-methyl-2-p-tolyloxazole-4-carbaldehyde as a yellow solid. C12H11 NO2 (201.23), LCMS(ESI): 202.1 (MH+).

Methyl [cis-3-(tert-butyldimethylsilanyloxy)cyclohexyl]carboxylate

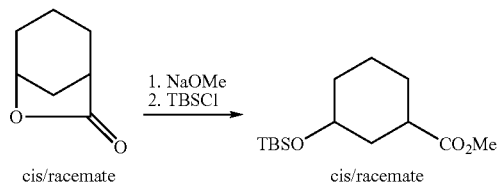

47 g of 6-oxabicyclo[3.2.1]octan-7-one are dissolved in 500 ml of MeOH, and 40.5 g of NaOMe are added. After 2.5 hours of stirring at room temperature, 135 ml of acetic acid are added and most of the methanol is distilled off. The residue is taken up in ethyl acetate/water and the phases are separated. The aqueous phase is extracted with ethyl acetate and the combined organic phases are dried over MgSO4 and concentrated, the residue being the methyl ester in quantitative yield.

10.7 g of the residue are dissolved in 100 ml of dimethylformamide, and 11.2 g of tert-butyldimethylsilyl chloride are added. At 0° C., 11.5 g of imidazole are added, and the solution is stirred at room temperature overnight. 200 ml of saturated NaCl solution are added and the solution is extracted three times with methyl tert-butyl ether. The combined organic phases are washed with saturated NaCl solution, dried over MgSO4 and concentrated. This gives 16.4 g of methyl [cis-3-(tert-butyldimethylsilanyl-oxy)cyclohexyl]carboxylate as a colorless oil. C14H28O3Si (272.46), MS(ESI): 273.13 (MH+).

Methyl cis-3-(5-methyl-2-p-tolyloxazol-4-yl-methoxy)cyclohexane-carboxylate

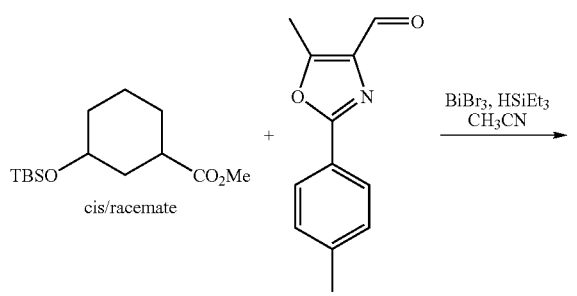

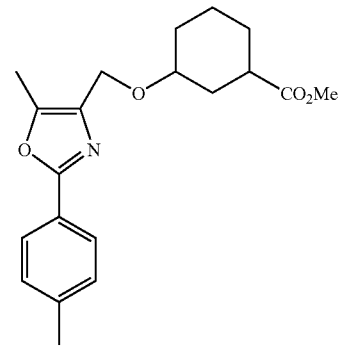

At room temperature, 1.35 g of methyl [cis-3-(tert-butyldimethylsilanyloxy)-cyclohexyl]acetate are added dropwise to a mixture of 4.0 ml of HSiEt3 and 1.50 g of BiBr3 in 20 ml of acetonitrile. 1.51 g of 5-methyl-2-p-tolyloxazole-4-carbaldehyde in 5 ml of acetonitrile are then added, and the mixture is stirred at room temperature for 4 h. The suspension is filtered and concentrated. The residue is chromatographed on silica gel (dichloro-methane/methanol 100/1), giving 1.20 g of methyl cis-3-(5-methyl-2-p-tolyl-oxazol-4-ylmethoxy)cyclohexanecarboxylate as a light-yellow oil.

C20H25NO4 (343.43), LCMS(ESI): 344.1 (MH+).- cis-3-(5-Methyl-2-p-tolyloxazol-4-ylmethoxy)cyclo-hexyl]methanol

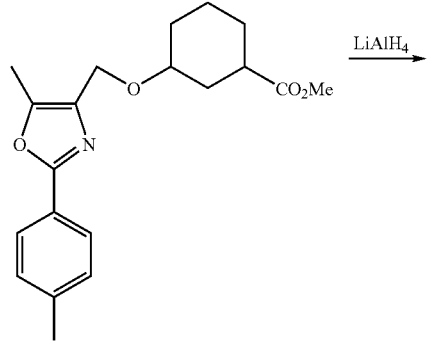

cis/racemate

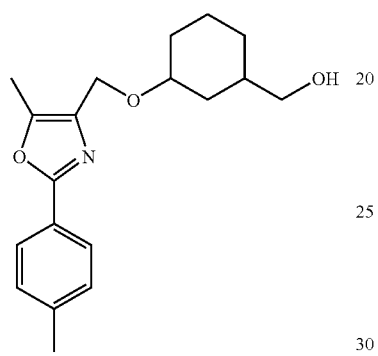

cis/racemate

At 0° C., 1.70 g of methyl cis-3-(5-methyl-2-p-tolyloxazol-4-ylmethoxy)cyclo-hexanecarboxylate in 5 ml of tetrahydrofuran are added dropwise to a suspension of 380 mg of LiAlH4 in 50 ml of diethyl ether, and the mixture is stirred at room temperature for 2 h. 3 g of $MgSO_4$, 30 ml of methyl tert-butyl ether and 3 ml of ethyl acetate are added successively, and the suspension is stirred at room temperature. The mixture is then cooled to 0° C., 1 ml of 10N KOH is added dropwise and the mixture is stirred for another 60 min. The solids are filtered off, the residue is washed three times with ethyl acetate and the filtrate is concentrated, giving 1.55 g of cis-3-(5-methyl-2-p-tolyloxazol-4-ylmethoxy)cyclohexyl]methanol as a yellow oil.

C19H25NO3 (315.42), MS(EI): 315.4 (M+).

4-(cis-3-Iodomethylcyclohexyloxymethyl)-5-methyl-2-p-tolyloxazole

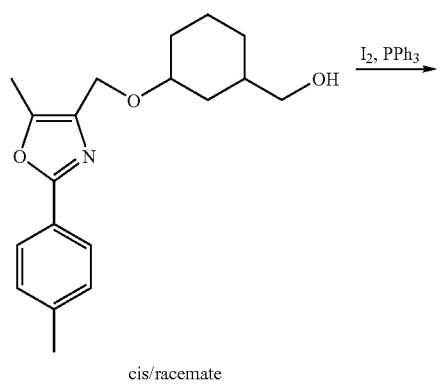

cis/racemate

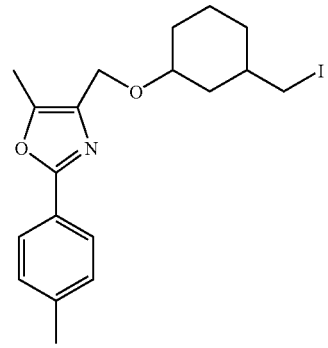

cis/racemate 1.56 g of PPh3, 0.87 g of imidazole and 1.64 g of iodine are added to 1.55 g of cis-3-(5-methyl-2-p-tolyloxazol-4-ylmethoxy)cyclohexyl]methanol in 20 ml of toluene, and the mixture is stirred at room temperature for 2 h. 10 ml of dichloromethane are then added, and the mixture is stirred for another 60 min. The solution is diluted with 50 ml of water and 50 ml of methyl tert-butyl ether, the phases are separated and the organic phase is dried over MgSO4 and concentrated. Filtration of the residue through silica gel using dichloromethane gives 1.12 g of 4-(cis-3-iodomethylcyclohexyl-oxymethyl)-5-methyl-2-p-tolyloxazole as a yellow solid.

$C19H24INO_2$ (425.31); LCMS (ESI): 426.0 (MH+).

Ethyl cis-3-(5-methyl-2-p-tolyloxazol-4-ylmethoxy)cyclohexylmethyl-sulfanyl]acetate

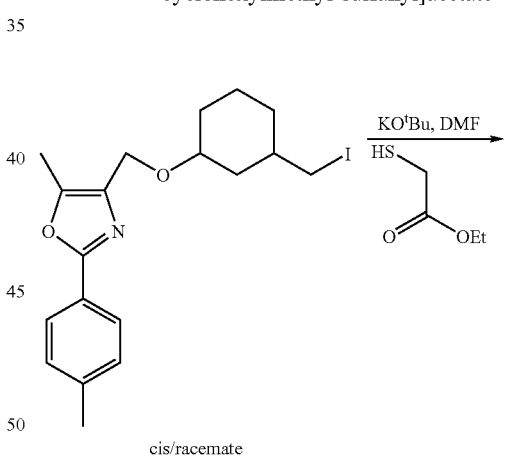

cis/racemate

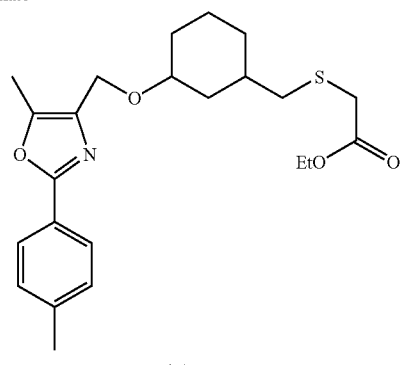

cis/racemate 50 mg of KO^tBu are added to 68 mg of ethyl mercaptoacetate in 1.5 ml of dimethylformamide, and the mixture is stirred at room temperature for 1 h. 120 mg of 4-(cis-3-iodomethylcyclohexyloxymethyl)-5-methyl-2-p-tolyl-oxazole are then added, and the solution is stirred at room temperature. After 1 h, 20 ml of methyl tert-butyl ether, 15 ml of saturated NaCl solution and 15 ml of water are added and the phases are separated. The aqueous phase is extracted with methyl tert-butyl ether and the combined organic phases are washed with saturated NaCl solution, dried over MgSO4 and concentrated, giving 117 mg of ethyl cis-3-(5-methyl-2-p-tolyloxazol-4-ylmethoxy)cyclohexylmethylsulfanyl]acetate. C23H31NO4S (417.57); LCMS (ESI): 418.1 (MH+).

cis-3-(5-Methyl-2-p-tolyloxazol-4-ylmethoxy)cyclohexylmethylsulfanyl]acetic acid

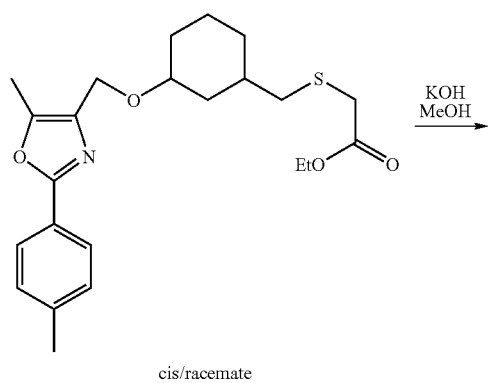

cis/racemate

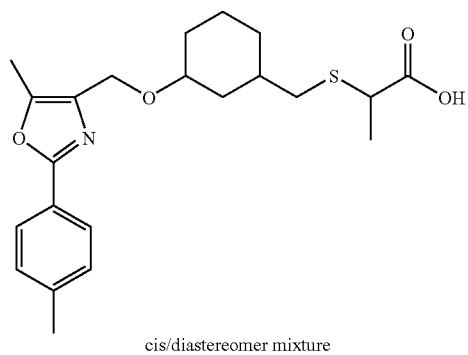

cis/racemate 117 mg of ethyl cis-3-(5-methyl-2-p-tolyloxazol-4-ylmethoxy)cyclohexyl-methylsulfanyl]acetate are dissolved in 3 ml of methanol, 1 ml of 2N KOH is added and the mixture is stirred at room temperature overnight. 2 ml of 2N HCl, 10 ml of saturated NaCl solution, 5 ml of water and 20 ml of dichloromethane are then added, and the phases are separated. The organic phase is dried over MgSO4 and concentrated, giving 100 mg of cis-3-(5-methyl-2-p-tolyloxazol-4-ylmethoxy)cyclohexylmethylsulfanyl]acetic acid. C21H27NO4S (389.52); LCMS (ESI): 390.1 (MH+).

EXAMPLE 23

Analogously to Example 22, 4-(cis-3-iodomethylcyclohexyloxymethyl)-5-methyl-2-p-tolyloxazole and ethyl 2-mercaptopropionate give 2-[cis-3-(5-methyl-2-p-tolyloxazol-4-ylmethoxy)cyclohexylmethylsulfanyl]propionic acid as a mixture of diastereomers. C22H29NO4S (403.54), LCMS(ESI): 404.1 (MH+).

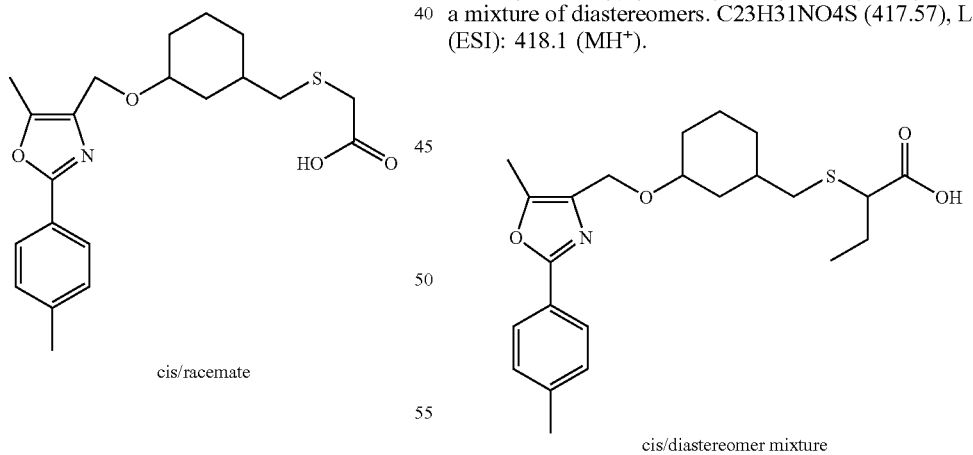

cis/diastereomer mixture

EXAMPLE 24

Analogously to Example 22, 4-(cis-3-iodomethylcyclohexyloxymethyl)-5-methyl-2-p-tolyloxazole and methyl 2-mercaptobutyrate give 2-[cis-3-(5-methyl-2-p-tolyloxazol-4-ylmethoxy)cyclohexylmethylsulfanyl]butyric acid as a mixture of diastereomers. C23H31NO4S (417.57), LCMS (ESI): 418.1 (MH+).

cis/diastereomer mixture

EXAMPLE 25

Analogously to Example 22, 4-(cis-3-iodomethylcyclohexyloxymethyl)-5-methyl-2-p-tolyloxazole and ethyl 2-mercaptoheptanoate give 2-[cis-3-(5-methyl-2-p-tolyloxazol-4-ylmethoxy)cyclohexylmethylsulfanyl]-heptanoic acid as a mixture of diastereomers. $C_{26}H_{37}NO_4S$ (459.65), MS(ESI): 460.41 (MH+).

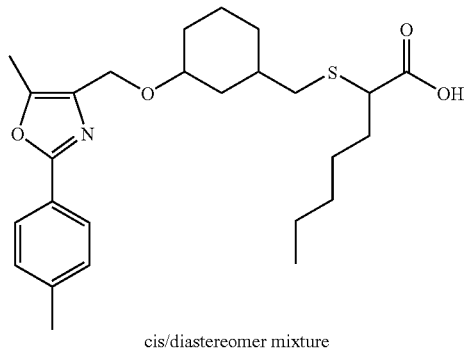

cis/diastereomer mixture

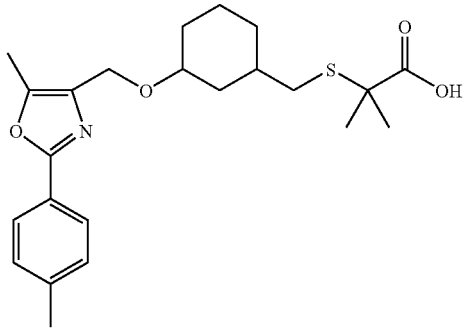

cis/racemate

EXAMPLE 26

Analogously to Example 22, 4-(cis-3-iodomethylcyclohexyloxymethyl)-5-methyl-2-p-tolyloxazole and ethyl 2-mercapto-3-methylbutyrate acid give 2-[cis-3-(5-methyl-2-p-tolyloxazol-4-ylmethoxy)cyclohexylmethylsulfanyl]-3-methylbutyric acid as a mixture of diastereomers. $C_{24}H_{33}NO4S$ (431.60), LCMS(ESI): 432.2 (MH$^+$).

EXAMPLE 28

Analogously to Example 22, 4-(cis-3-iodomethylcyclohexyloxymethyl)-5-methyl-2-p-tolyloxazole and ethyl 2-mercapto-2-phenylacetate give 2-[cis-3-(5-methyl-2-p-tolyloxazol-4-ylmethoxy)cyclohexylmethylsulfanyl]-2-phenylacetic acid as a mixture of diastereomers. $C_{27}H_{31}NO4S$ (465.62), MS(ESI): 466.39 (MH$^+$).

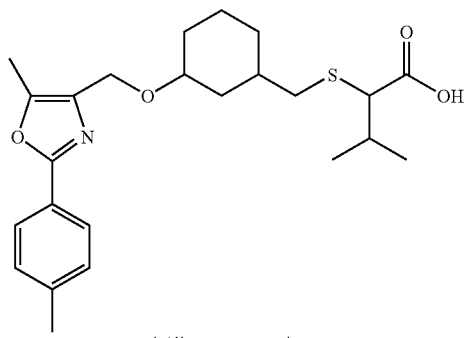

cis/diastereomer mixture cis/diastereomer mixture

EXAMPLE 27

Analogously to Example 22, 4-(cis-3-iodomethylcyclohexyloxymethyl)-5-methyl-2-p-tolyloxazole and ethyl 2-mercapto-2-methylpropionate give 2-[cis-3-(5-methyl-2-p-tolyloxazol-4-ylmethoxy)cyclohexylmethylsulfanyl]-2-methylpropionic acid. C23H31NO45 (417.57), LCMS(ESI): 418.1 (MH$^+$).

EXAMPLE 29

Analogously to Example 22, 4-(cis-3-iodomethylcyclohexyloxymethyl)-5-methyl-2-p-tolyloxazole and ethyl 2-mercapto-2-cyclohexylacetate give 2-[cis-3-(5-methyl-2-p-tolyloxazol-4-ylmethoxy)cyclohexylmethylsulfanyl]-2-cyclohexylacetic acid as a mixture of diastereomers. $C_{27}H_{37}NO4S$ (471.66), LCMS(ESI): 472.2 (MH$^+$).

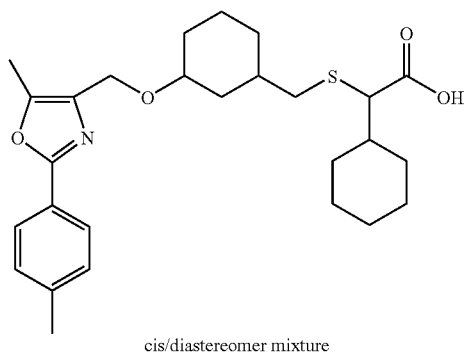

cis/diastereomer mixture

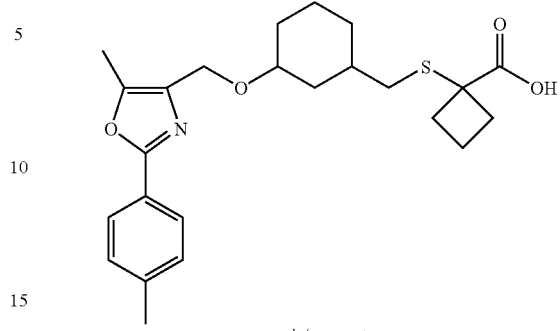

cis/racemate

EXAMPLE 30

Analogously to Example 22, 4-(cis-3-iodomethylcyclohexyloxymethyl)-5-methyl-2-p-tolyloxazole and ethyl 2-mercaptovalerate give 2-[cis-3-(5-methyl-2-p-tolyloxazol-4-ylmethoxy)cyclohexylmethylsulfanyl]valeric acid as a mixture of diastereomers. C24H33NO4S (431.60), MS(ESI): 432.39 (MH+).

Building Block Synthesis of the Methyl 2-Mercaptobutyrates

Methyl 2-mercaptobutyrate

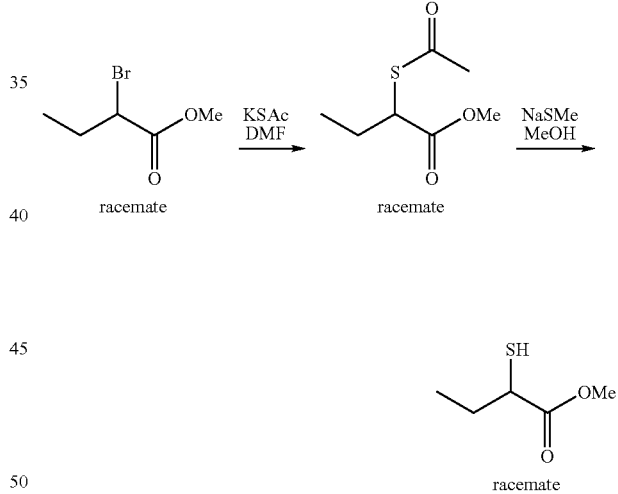

racemate

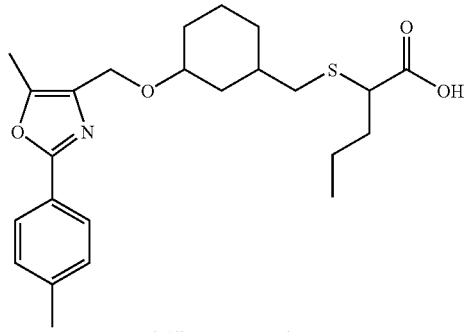

cis/diastereomer mixture

EXAMPLE 31

Analogously to Example 22, 4-(cis-3-iodomethylcyclohexyloxymethyl)-5-methyl-2-p-tolyloxazole and ethyl 1-mercaptocyclobutanecarboxylate give 1-[cis-3-(5-methyl-2-p-tolyloxazol-4-ylmethoxy)cyclohexylmethylsulfanyl]-cyclobutanecarboxylic acid. C24H31NO4S (429.58), MS(ESI): 430.35 (MH+).

1.43 g of KSAc are added to 1.81 g of methyl 2-bromobutyrate in 5 ml of dimethylformamide, and the mixture is stirred at room temperature for 12 h. 25 ml of methyl tert-butyl ether, 10 ml of water and 15 ml of saturated NaCl solution are then added, and the phases are separated. The aqueous phase is extracted with methyl tert-butyl ether and the combined organic phases are washed with saturated NaCl solution, dried over MgSO4 and concentrated, giving methyl 2-acetylsulfanylbutyrate as a yellow oil. This is taken up in 10 ml of methanol, 11 ml of a 1M NaSMe solution in methanol are added and the mixture is stirred at room temperature overnight. The solvent is distilled off completely under reduced pressure, the residue is taken up in 15 ml of methyl tert-butyl ether and 20 ml of water, the phases are separated and the organic phase is washed with saturated NaCl solution and dried over MgSO4. The solution is concentrated under reduced pressure, giving 1.30 g of methyl 2-mercaptobutyrate as a yellow oil.

Analogously to the building block synthesis of the methyl 2-mercaptobutyrates, ethyl 2-bromoheptanoate gives ethyl 2-mercapto-heptanoate.

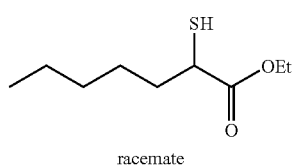

racemate

Analogously to the building block synthesis of the methyl 2-mercaptobutyrates, ethyl 2-bromo-3-methylbutyrate acid gives ethyl 2-mercapto-3-methylbutyrate acid.

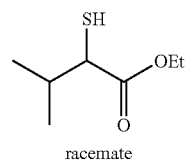

racemate

Analogously to the building block synthesis of the methyl 2-mercaptobutyrates, ethyl 2-bromo-2-methylpropionate acid gives ethyl 2-mercapto-2-methylpropionate acid.

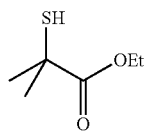

Analogously to the building block synthesis of the methyl 2-mercaptobutyrates, ethyl 2-bromo-2-phenylacetate gives ethyl 2-mercapto-2-phenylacetate.

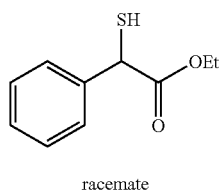

racemate

Analogously to the building block synthesis of the methyl 2-mercaptobutyrates, methyl 2-bromo-2-cyclohexylacetate gives methyl 2-mercapto-2-cyclohexylacetate.

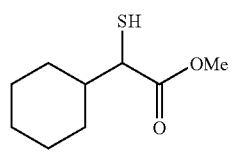

racemate

Analogously to the building block synthesis of the methyl 2-mercaptobutyrates, ethyl 2-bromovalerate gives ethyl 2-mercapto-valerate.

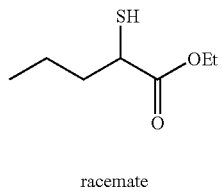

racemate

Analogously to the building block synthesis of the methyl 2-mercaptobutyrates, ethyl 1-bromocyclobutanecarboxylate gives ethyl 1-mercaptocyclobutanecarboxylate.

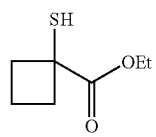

EXAMPLE 32 cis-3-(5-Methyl-2-p-tolyloxazol-4-ylmethoxy)cyclohexylmethylsulfinyl]acetic acid 65 mg of cis-3-(5-methyl-2-p-tolyloxazol-4-ylmethoxy) cyclohexylmethyl-sulfanyl]acetic acid are dissolved in 1.5 ml of trifluoroacetic acid, 6.3 μl of 35% $H_2O_2$ are added at 0° C. and the mixture is stirred overnight at room temperature. Saturated NH4Cl solution and methyl tert-butyl ether are added, the phases are separated, the aqueous phase is extracted with methyl tert-butyl ether and the combined organic phases are washed with saturated NaCl solution, dried over MgSO4 and concentrated. The residue is purified by HPLC, which gave 6.6 mg of a colorless solid. $C_{21}H_{27}NO5S$ (405.52), LCMS(ESI): 406.1 (MH$^+$).

EXAMPLE 33

Analogously to Example 32, 2-[cis-3-(5-methyl-2-p-tolyloxazol-4-ylmethoxy)cyclohexylmethylsulfanyl]heptanoic acid gives 2-[cis-3-(5-methyl-2-p-tolyloxazol-4-ylmethoxy)cyclohexylmethylsulfinyl]heptanoic acid as a mixture of diastereomers.

C26H37NO5S (475.65), MS(ESI): 476.18 (MH$^+$).

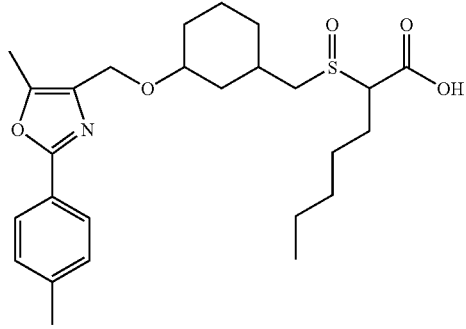

cis/diastereomer mixture

EXAMPLE 34

Analogously to Example 32, 2-[cis-3-(5-methyl-2-p-tolyloxazol-4-ylmethoxy)cyclohexylmethylsulfanyl]-2-methylpropionic acid gives 2-[cis-3-(5-methyl-2-p-tolyloxazol-4-ylmethoxy)cyclohexylmethylsulfinyl]-2-methylpropionic acid. $C_{23}H_{31}NO_5S$ (433.57), LCMS(ESI): 434.1 (MH$^+$).

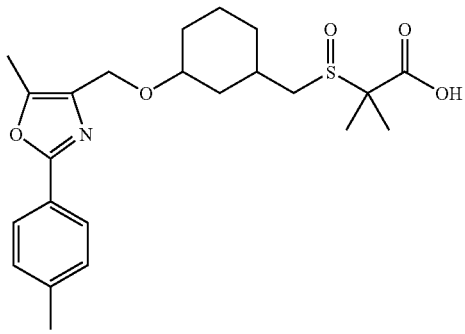

cis/diastereomer mixture

EXAMPLE 35

Analogously to Example 32, 2-[cis-3-(5-methyl-2-p-tolyloxazol-4-yl-methoxy)cyclohexylmethylsulfanyl]-3-methylbutyric acid gives 2-[cis-3-(5-methyl-2-p-tolyloxazol-4-ylmethoxy)cyclohexylmethylsulfinyl]-3-methylbutyric acid as a mixture of diastereomers. $C_{24}H_{33}NO5S$ (447.60), MS(ESI): 448.43 (MH$^+$).

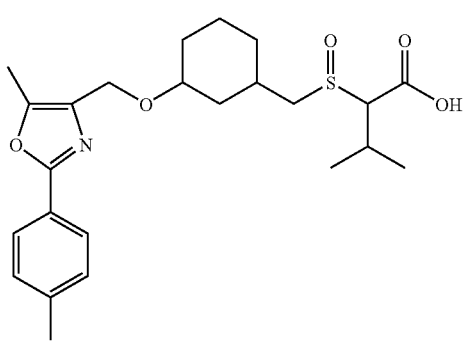

cis/diastereomer mixture

EXAMPLE 36

Analogously to Example 32, 2-[cis-3-(5-methyl-2-p-tolyloxazol-4-ylmethoxy)cyclohexylmethylsulfanyl]valeric acid gives 2-[cis-3-(5-methyl-2-p-tolyloxazol-4-ylmethoxy)cyclohexylmethylsulfinyl]valeric acid as a mixture of diastereomers. $C_{24}H_{33}NO5S$ (447.60), MS(ESI): 448.14 (MH$^+$).

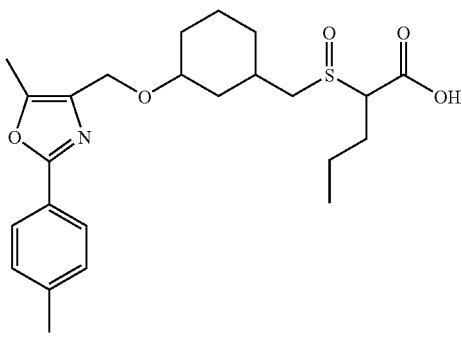

cis/diastereomer mixture

EXAMPLE 37 cis-3-(5-Methyl-2-p-tolyloxazol-4-ylmethoxy)cyclohexylmethylsulfonyl]acetic acid

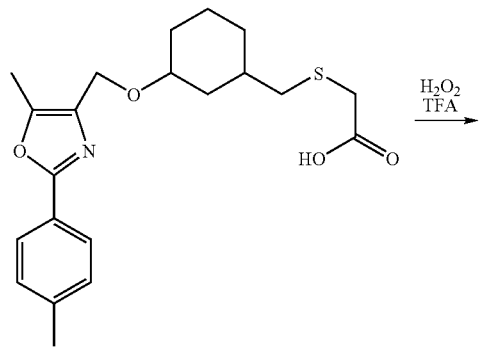 

cis/racemate

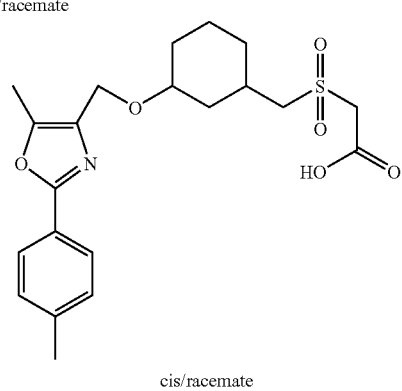

cis/racemate 65 mg of cis-3-(5-methyl-2-p-tolyloxazol-4-ylmethoxy)cyclohexylmethyl-sulfanyl]acetic acid are dissolved in 1.5 ml of trifluoroacetic acid, 21.5 µl of 35% $H_2O_2$ are added at 0° C. and the mixture is stirred at room temperature overnight. Saturated NH4Cl solution and methyl tert-butyl ether are added, the phases are separated, the aqueous phase is extracted with methyl tert-butyl ether and the combined organic phases are washed with, saturated NaCl solution, dried over MgSO4 and concentrated. The residue is purified by HPLC, which gave 6.6 mg of a colorless solid. C21H27NO6S (421.52), LCMS(ESI): 422.1 (MH$^+$).

EXAMPLE 38

Analogously to Example 37, 2-[cis-3-(5-methyl-2-p-tolyloxazol-4-yl-methoxy)cyclohexylmethylsulfanyl]heptanoic acid gives 2-[cis-3-(5-methyl-2-p-tolyloxazol-4-ylmethoxy)cyclohexylmethylsulfonyl]heptanoic acid as a mixture of diastereomers. C26H37NO6S (491.65), MS(ESI): 492.42 (MH$^+$).

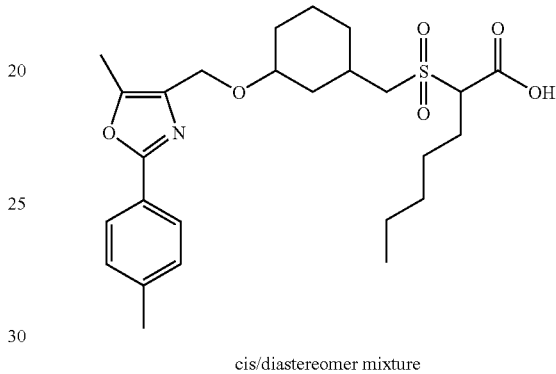

cis/diastereomer mixture

EXAMPLE 39

Analogously to Example 37, 2-[cis-3-(5-methyl-2-p-tolyloxazol-4-yl-methoxy)cyclohexylmethylsulfanyl]-2-methylbutyric acid gives 2-[cis-3-(5-methyl-2-p-tolyloxazol-4-ylmethoxy)cyclohexylmethylsulfonyl]-2-methylbutyric acid. C23H31NO6S (449.57), LCMS(ESI): 450.1 (MH$^+$).

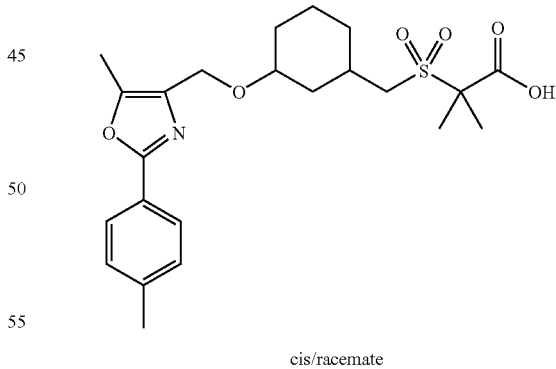

cis/racemate

EXAMPLE 40

Analogously to Example 37, 2-[cis-3-(5-methyl-2-p-tolyloxazol-4-yl-methoxy)cyclohexylmethylsulfanyl]-3-methylbutyric acid gives 2-[cis-3-(5-methyl-2-p-tolyloxazol-4-ylmethoxy)cyclohexylmethylsulfonyl]-3-methyl-butyric acid as a mixture of diastereomers. C24H33NO6S (463.60), LCMS (ESI): 464.1 (MH$^+$).

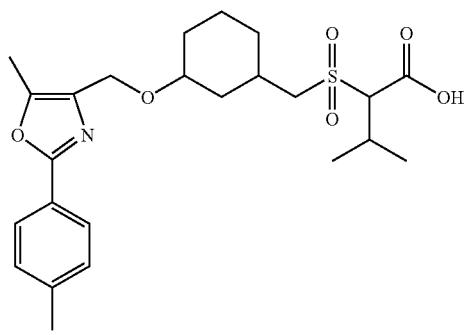

cis/diastereomer mixture

EXAMPLE 41

Analogously to Example 37, 2-[cis-3-(5-methyl-2-p-tolyloxazol-4-yl-methoxy)cyclohexylmethylsulfanyl]valeric acid gives 2-[cis-3-(5-methyl-2-p-tolyloxazol-4-ylmethoxy)cyclohexylmethylsulfonyl]valeric acid as a mixture of diastereomers. C24H33NO6S (463.60), MS (ESI): 464.14 (MH$^+$).

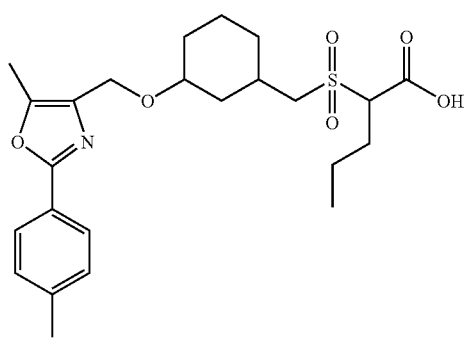

cis/diastereomer mixture

EXAMPLE 42

(S)-3-Methyl-2{[cis-3-(5-methyl-2-p-tolyloxazol-4-ylmethoxy)cyclohexyl-methyl]amino}butyric acid

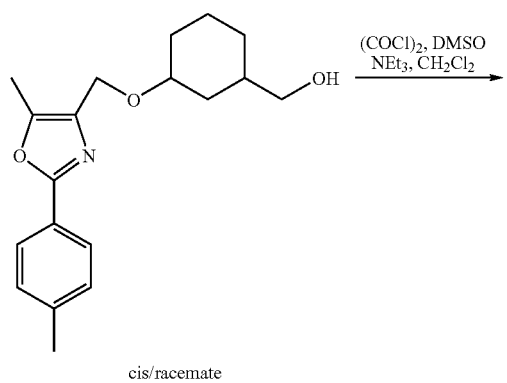

cis/racemate

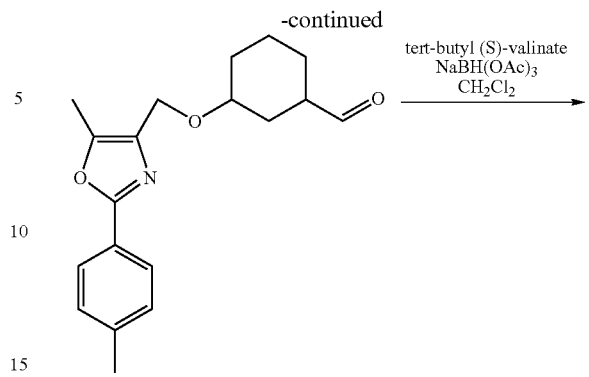

cis/racemate cis/diastereomer mixture cis/diastereomer mixture cis-3-(5-Methyl-2-p-tolyloxazol-4-ylmethoxy)cyclohexanecarbaldehyde

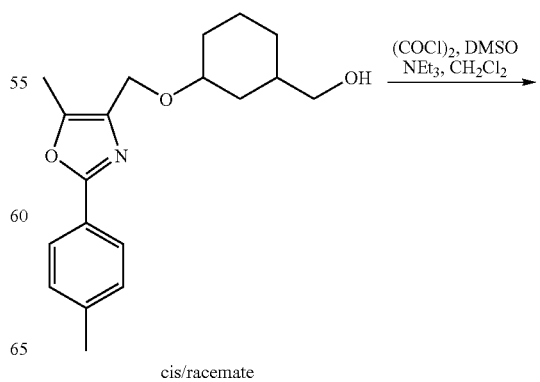

cis/racemate

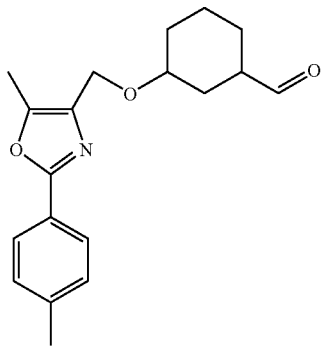

cis/racemate

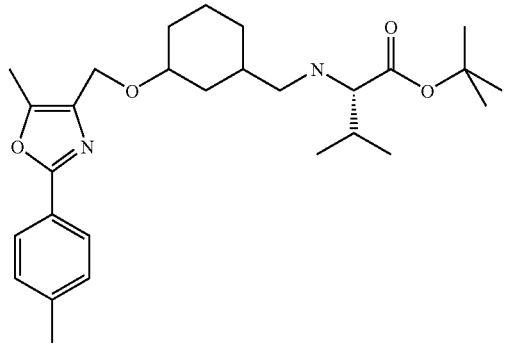

cis/diastereomer mixture

At −78° C., 089 ml of DMSO in 1 ml of dichloromethane are added dropwise to 0.48 ml of oxalyl chloride in 15 ml of dichloromethane such that the temperature does not exceed −70° C. After the end of the addition, the solution is stirred at this temperature for 30 min. 1.5 g of cis-3-(5-methyl-2-p-tolyloxazol-4-ylmethoxy)cyclohexyl]methanol in 2 ml of dichloromethane are then added dropwise such that the temperature remains below −78° C. The solution is stirred at this temperature for 30 min. 3.2 ml of NEt3 are then added dropwise, the cooling bath is removed and the solution is warmed to 0° C. At this temperature, 10 ml of water are added, and the mixture is stirred vigorously at room temperature. The aqueous phase is removed and extracted with dichloromethane. The combined organic phases are washed with saturated NH$_4$Cl solution, dried over MgSO$_4$ and concentrated, giving 1.50 g of cis-3-(5-methyl-2-p-tolyloxazol-4-ylmethoxy)-cyclohexanecarbaldehyde. C19H23NO3 (313.40); LCMS (ESI): 314.1 (MH$^+$).

tert-Butyl (S)-3-methyl-2-{[cis-3-(5-methyl-2-p-tolyloxazol-4-ylmethoxy)-cyclohexylmethyl]amino}butyrate 511 mg of cis-3-(5-methyl-2-p-tolyloxazol-4-ylmethoxy)cyclohexanecarbaldehyde, 0.9 ml of HOAc and 310 mg of tert-butyl (S)-valinate are dissolved in 5 ml of abs. dichloromethane. 500 mg of molecular sieve 4 Å are then added, and the suspension is cooled to 0° C. 414 mg of sodium triacetoxyborohydride are added a little at a time. This suspension is stirred at 0° C. for 2 h, 3 ml of saturated NH4Cl solution are then added and the suspension is stirred for a further 10 min. In each case 10 ml of water and dichloromethane are added, the phases are separated, the aqueous phase is extracted with dichloromethane and the combined organic phases are dried over MgSO4 and concentrated, which gives 760 mg of tert-butyl (S)-3-methyl-2-{[cis-3-(5-methyl-2-p-tolyloxazol-4-ylmethoxy)cyclohexylmethyl]-amino}butyrate. C28H42N2O4 (470.66); MS (ESI): 471.50 (MH$^+$).

(S)-3-Methyl-2-{[cis-3-(5-methyl-2-p-tolyloxazol-4-ylmethoxy)cyclohexyl-methyl]amino}butyric acid

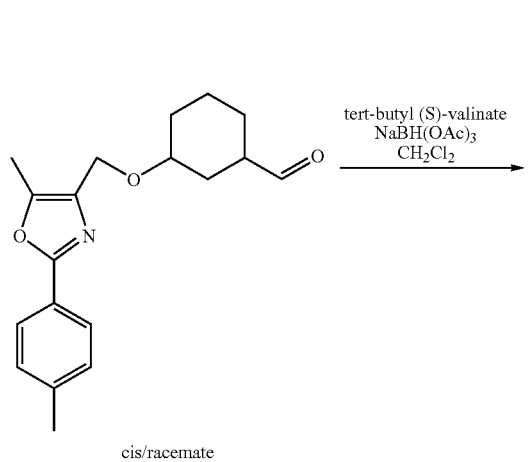

cis/racemate

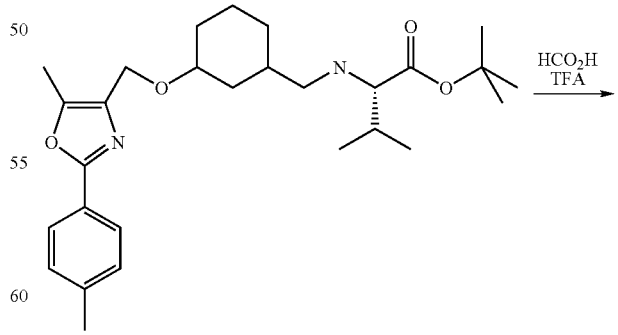

cis/diastereomer mixture

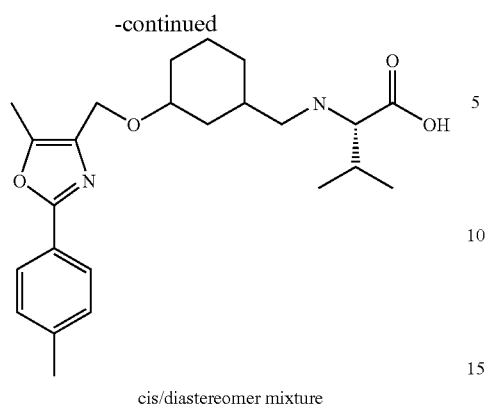

cis/diastereomer mixture 40 mg of tert-butyl (S)-3-methyl-2-{[cis-3-(5-methyl-2-p-tolyloxazol-4-ylmethoxy)cyclohexylmethyl]amino}butyrate are dissolved in 1 ml of formic acid, and 0.5 ml of trifluoroacetic acid is added. The solution is stirred at room temperature for 18 and then concentrated completely. The residue is purified by HPLC, which gives 28.2 mg of (S)-3-methyl-2-{[cis-3-(5-methyl-2-p-tolyloxazol-4-ylmethoxy)cyclohexylmethyl]amino}butyric acid trifluoroacetic acid salt as a colorless solid. $C_{24}H_{34}N_2O_2 \cdot C_2HF_3O_2$ (414.55); MS (ES-): 413.28 ($M^+$-H).

EXAMPLE 43

(S)-2-{Acetyl-[cis-3-(5-methyl-2-p-tolyloxazol-4-ylmethoxy)cyclohexyl-methyl]amino}-3-methylbutyric acid

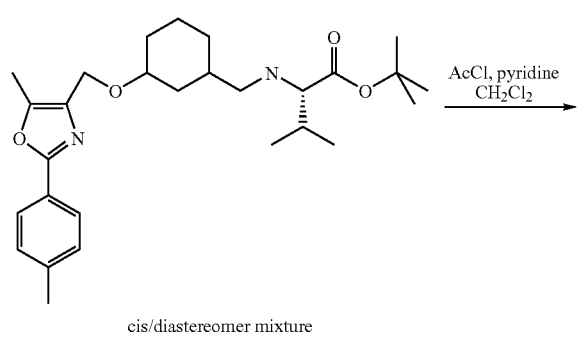

cis/diastereomer mixture

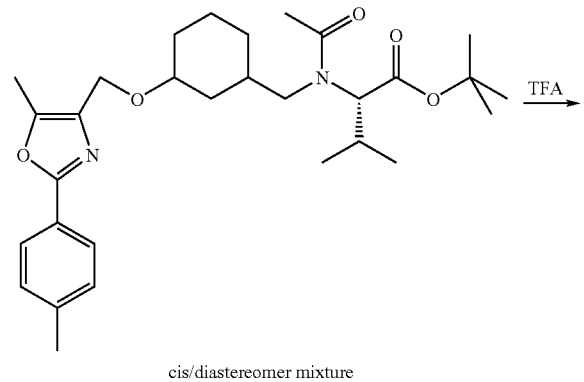

cis/diastereomer mixture

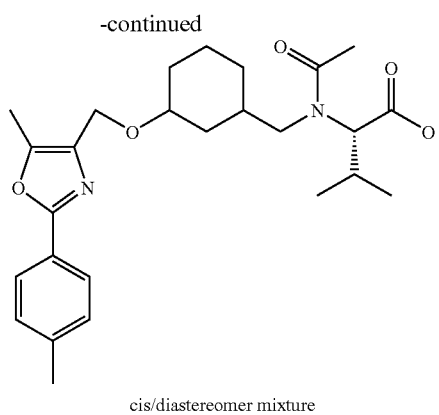

cis/diastereomer mixture (S)-2-{Acetyl-[cis-3-(5-methyl-2-p-tolyloxazol-4-ylmethoxy)cyclohexyl-methyl]amino}-3-methylbutyric acid

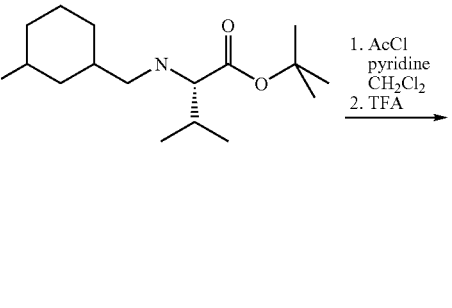

cis/diastereomer mixture

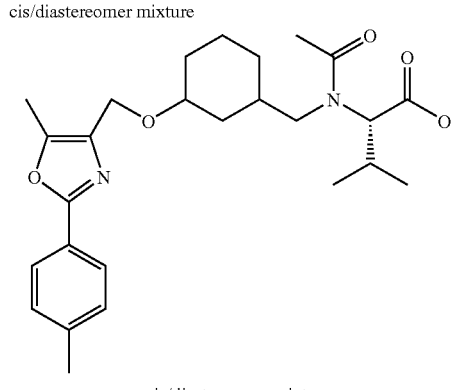

cis/diastereomer mixture

12 µl of acetyl chloride and 22 µl of pyridine are added to 40 mg of tert-butyl (S)-3-methyl-2-{[cis-3-(5-methyl-2-p-tolyloxazol-4-ylmethoxy)cyclohexylmethyl]amino}butyrate in 0.5 ml of dichloromethane, and the mixture is stirred at room temperature for 18 h. The solution is then diluted with water and dichloromethane, the aqueous phase is removed and extracted with dichloromethane and the combined phases are dried over MgSO4 and concentrated. The residue is taken up in 0.5 ml of trifluoroacetic acid and allowed to stand at room temperature overnight. The solvent is distilled off completely and the residue is purified by HPLC, which gives 17 mg of (S)-2-{acetyl-[cis-3-(5-methyl-2-p-tolyloxazol-4-ylmethoxy)cyclohexylmethyl]amino}-3-methylbutyric acid. C26H36N2O5 (456.59); LCMS (ESI): 457.36 (MH+).

EXAMPLE 44

Analogously to Example 43, tert-butyl (S)-3-methyl-2-{[cis-3-(5-methyl-2-p-tolyloxazol-4-ylmethoxy)cyclohexylmethyl]amino}butyrate and benzoyl chloride give (S)-2-{benzoyl-[cis-3-(5-methyl-2-p-tolyloxazol-4-ylmethoxy)cyclohexylmethyl]amino}-3-methylbutyric acid. C31H38N2O5 (518.29); LCMS (ESI): 519.54 (MH+).

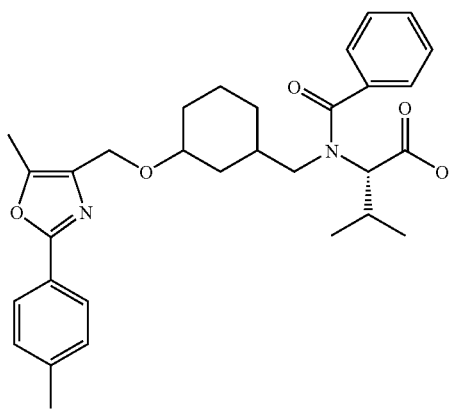

cis/diastereomer mixture

EXAMPLE 45

Analogously to Example 43, tert-butyl (S)-3-methyl-2-{[cis-3-(5-methyl-2-p-tolyloxazol-4-ylmethoxy)cyclohexylmethyl]amino}butyrate and methyl-sulfonyl chloride give (S)-2-{methylsulfonyl-[cis-3-(5-methyl-2-p-tolyloxazol-4-ylmethoxy)cyclohexylmethyl]amino}-3-methylbutyric acid. C25H36N2O6S (492.23); LCMS (ESI): 493.26 (MH+).

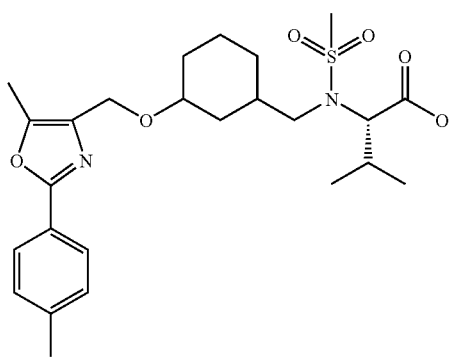

cis/diastereomer mixture

EXAMPLE 46

Analogously to Example 43, tert-butyl (S)-3-methyl-2-{[cis-3-(5-methyl-2-p-tolyloxazol-4-ylmethoxy)cyclohexylmethyl]amino}butyrate and methyl-sulfonyl chloride in triethylamine give (S)-2-{methylsulfonylmethylsulfonyl-[cis-3-(5-methyl-2-p-tolyloxazol-4-ylmethoxy)cyclohexylmethyl]amino}-3-methylbutyric acid. C26H38N2O8S2 (570.21); LCMS (ES−): 569.23 (M+−H).

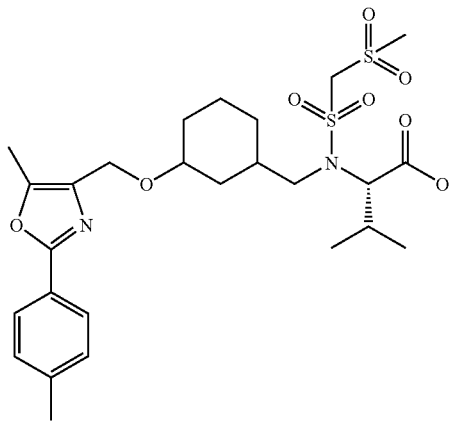

cis/diastereomer mixture

EXAMPLE 47

Analogously to Example 43, tert-butyl (S)-3-methyl-2-{[cis-3-(5-methyl-2-p-tolyloxazol-4-ylmethoxy)cyclohexylmethyl]amino}butyrate and p-toluenesulfonyl chloride give (S)-2-{p-toluenesulfonyl-[cis-3-(5-methyl-2-p-tolyloxazol-4-ylmethoxy)cyclohexylmethyl]amino}-3-methylbutyric acid. C31H40N2O6S (568.26); LCMS (ESI): 569.35 (MH+).

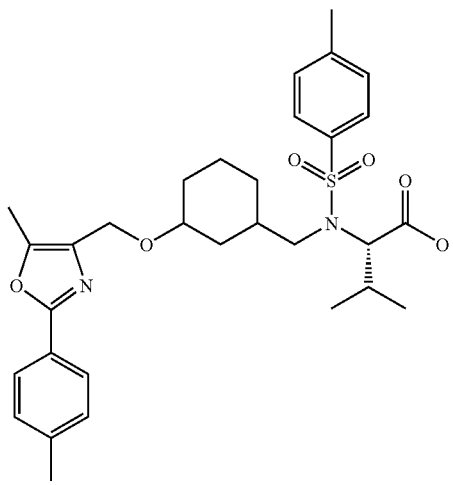

cis/diastereomer mixture

EXAMPLE 48

Analogously to Example 43, tert-butyl (S)-3-methyl-2-{[cis-3-(5-methyl-2-p-tolyloxazol-4-ylmethoxy)cyclohexylmethyl]amino}butyrate and methyl chloroformate give (S)-2-{methoxycarbonyl-[cis-3-(5-methyl-2-p-tolyloxazol-4-ylmethoxy)cyclohexylmethyl]amino}-3-methylbutyric acid. C26H36N2O6 (472.26), LCMS (ESI): 473.37 (MH+)

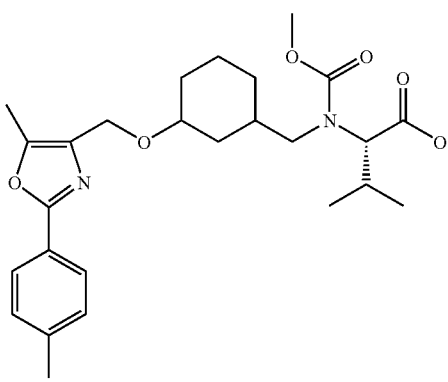

cis/diastereomer mixture

EXAMPLE 49

Analogously to 42, cis-3-(5-methyl-2-p-tolyloxazol-4-yl-methoxy)-cyclohexanecarbaldehyde and isopropyl glycinate hydrochloride give 2-{[cis-3-(5-methyl-2-p-tolyloxazol-4-ylmethoxy)cyclohexylmethyl]amino}-acetic acid trifluoroacetic acid salt. C21H28N2O4 (486.49), MS (ESI): 487 (MH$^+$).

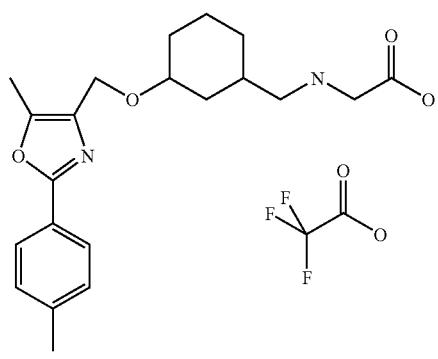

cis/racemate

EXAMPLE 50

(S)-2-{Methyl-[cis-3-(5-methyl-2-p-tolyloxazol-4-ylmethoxy)cyclohexyl-methyl]amino}-3-methylbutyric acid trifluoroacetic acid salt

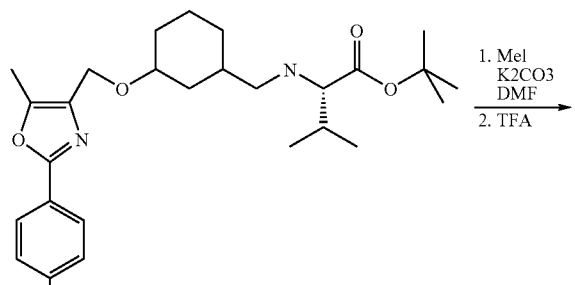

cis/diastereomer mixture

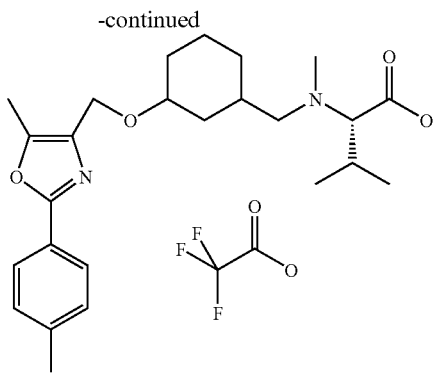

cis/diastereomer mixture 60 mg of methyl iodide and 12 mg of potassium carbonate are added to 40 mg of tert-butyl (S)-3-methyl-2-{[cis-3-(5-methyl-2-p-tolyloxazol-4-yl-methoxy)cyclohexylmethyl]amino}butyrate (see Example 42) in 0.5 ml of DMF, and the mixture is stirred at RT overnight. 1 ml of TFA is added to the reaction solution, and the mixture is stirred for a further 1 h. The solution is purified by preparative HPLC, yielding 6.4 mg of (S)-2-{methyl-[cis-3-(5-methyl-2-p-tolyloxazol-4-ylmethoxy)cyclohexylmethyl]amino}-3-methyl-butyric acid trifluoroacetic acid salt. C25H36N2O4 (542.60); MS (ESI): 543 (MH+).

EXAMPLE 51

Analogously to Example 50, tert-butyl (S)-3-methyl-2-{[cis-3-(5-methyl-2-p-tolyloxazol-4-ylmethoxy)cyclohexyl-methyl]amino}butyrate and benzyl bromide give (S)-2-{benzyl-[cis-3-(5-methyl-2-p-tolyloxazol-4-ylmethoxy)-cyclohexylmethyl]amino}-3-methylbutyric acid trifluoroacetic acid salt. C31H40N2O4 (618.70), MS (ESI): 619 (MH+).

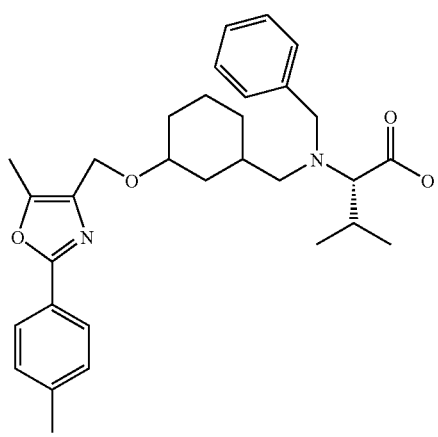

cis/diastereomer mixture

EXAMPLE 52

2-{Benzyl-[cis-3-(5-methyl-2-p-tolyloxazol-4-yl-methoxy)cyclohexylmethyl]-amino}acetic acid

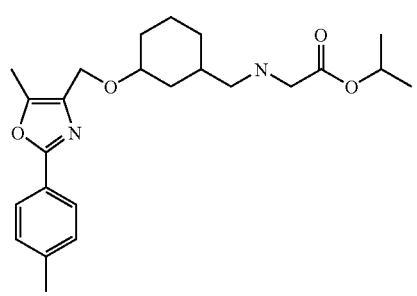

cis/racemate

1. Benzaldehyde
   CH2Cl2
   NaHB(OAc)3
2. LiOH

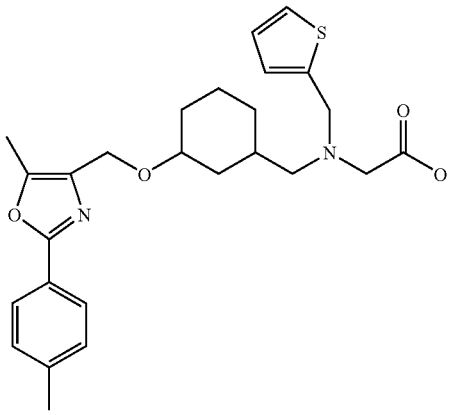

cis/racemate

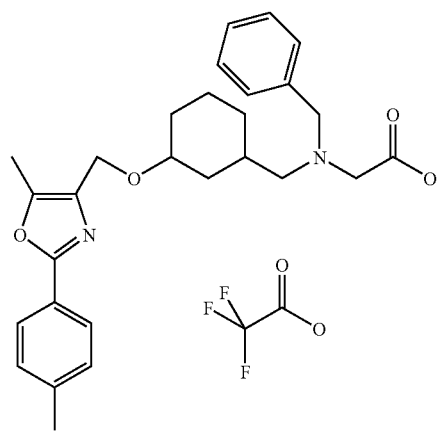

cis/racemate 120 mg of isopropyl 2-{[cis-3-(5-methyl-2-p-tolyloxazol-4-ylmethoxy)-cyclohexylmethyl]amino}acetate are dissolved in 1.5 ml of dichloromethane, and 62 mg of benzaldehyde, a spatula tip of MgSO4 and 68 mg of sodium triacetoxyborohyride are added successively. The suspension is stirred at RT overnight, and water is then added. The oraganic phase is separated off, washed with Na2CO3 solution, dried over MgSO4 and concentrated. The residue is dissolved in 0.7 ml of methanol and 0.23 ml of water, 20 mg of LiOH are added and the mixture is stirred at RT overnight. The solution is concentrated and the residue is purified by preparative HPLC, yielding 15 mg of 2-{benzyl-[cis-3-(5-methyl-2-p-tolyloxazol-4-ylmethoxy)cyclohexyl-methyl]amino}acetic acid. C28H34N2O4 (462.59); MS (ESI): 463 (MH+).

EXAMPLE 53

Analogously to Example 52, isopropyl 2-{[cis-3-(5-methyl-2-p-tolyloxazol-4-ylmethoxy)cyclohexylmethyl]amino}acetate and thiophene-2-carbaldehyde give 2-{2-thienylmethyl-[cis-3-(5-methyl-2-p-tolyloxazol-4-ylmethoxy)-cyclohexylmethyl]amino}acetic acid trifluoroacetic acid salt. C26H32N2O4 (468.62), MS (ESI): 469 (MH+).

EXAMPLE 54

Analogously to Example 52, isopropyl 2-{[cis-3-(5-methyl-2-p-tolyloxazol-4-ylmethoxy)cyclohexylmethyl]amino}acetate and cyclohexanecarbaldehyde give 2-{cyclohexylmethyl-[cis-3-(5-methyl-2-p-tolyloxazol-4-ylmethoxy)-cyclohexylmethyl]amino}acetic acid trifluoroacetic acid salt. C28H40N2O4 (468.64), MS (ESI): 469 (MH+).

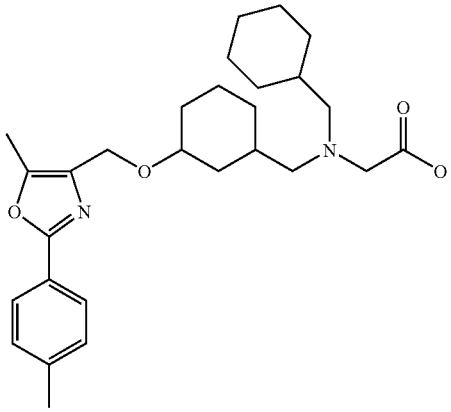

cis/racemate

EXAMPLE 55

2-[cis-3-(5-Methyl-2-p-tolyloxazol-4-ylmethoxymethyl)cyclohexylmethoxy]-2-methylpropionic acid

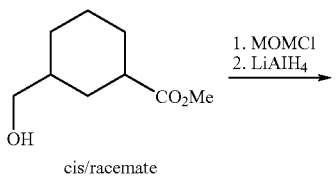

cis/racemate

1. MOMCl
2. LiAlH4

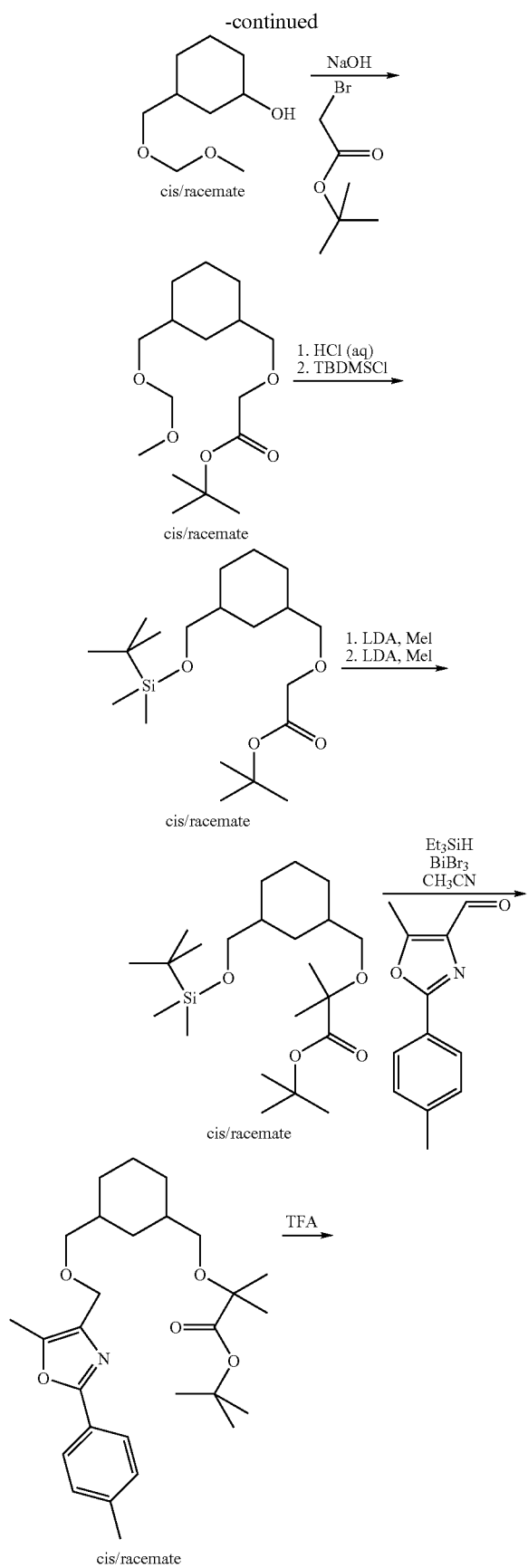

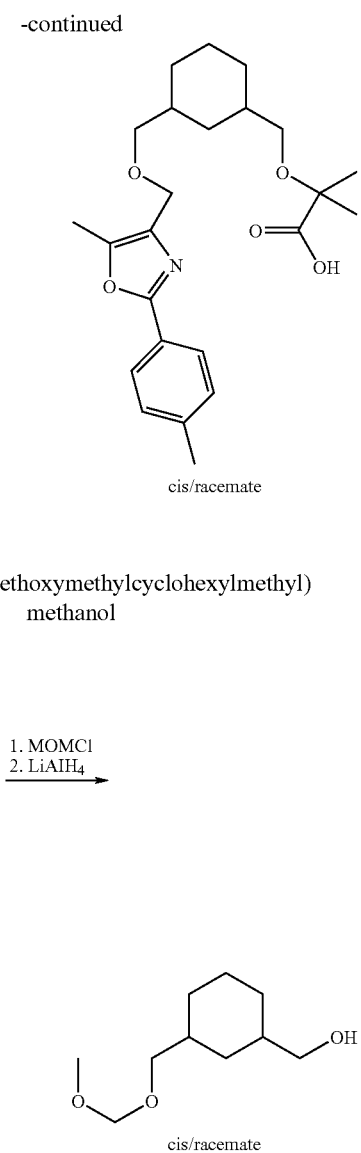

(cis-3-Methoxymethoxymethylcyclohexylmethyl)methanol 1.70 g of methyl cis-3-hydroxymethylcyclohexanecarboxylate are dissolved in 20 ml of dichloromethane, 1.60 g of methoxymethyl chloride and 2.60 g of diisopropylamine are added and the mixture is stirred at room temperature for 15 h. 50 ml of saturated NH4Cl solution and 50 ml of water are added to the solution, and the organic phase is separated off. The aqueous phase is extracted with dichloromethane and the combined organic phases are dried over magnesium sulfate and concentrated. This gives 2.0 g of methyl cis-3-methoxymethoxymethylcyclohexanecarboxylate as a yellow oil. This is dissolved in 50 ml of diethyl ether, 350 mg of LiAlH4 are added and the mixture is stirred at room temperature. After 2 h at 0° C., 5 ml of ethyl acetate, 40 ml of methyl tert-butyl ether and 3 g of MgSO4 are added. 15 ml of 10N KOH are then added dropwise. The suspension is stirred for 3 h and filtered through Celite and the filtrate is concentrated, which gives 1.65 g of (cis-3-methoxymethoxymethylcyclohexyl)methanol as a colorless oil.

C10H20O3 (188.27), MS (ESI): 189.2 (MH$^+$).

tert-Butyl [cis-3-(methoxymethoxymethyl)cyclohexylmethoxy]acetate

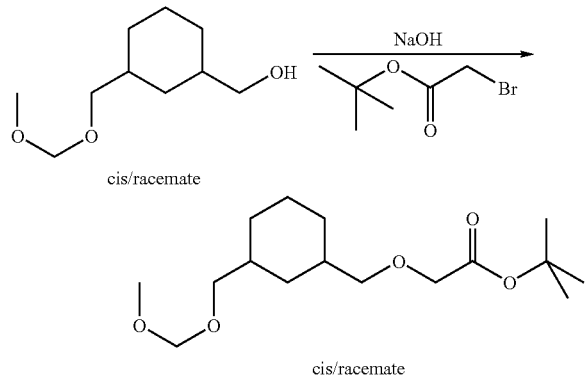

cis/racemate 1.65 g of (cis-3-methoxymethoxymethylcyclohexyl)methanol and 5.1 g of tert-butyl bromoacetate are dissolved in 20 ml of toluene, and 1.50 g of tetrabutylammonium hydrogensulfate are added. The suspension is cooled to 10° C. 20 ml of 50% NaOH are added to the suspension. The mixture is stirred at 10° C. for 6 h and the aqueous phase is then removed and extracted with methyl tert-butyl ether. The combined organic phases are dried over MgSO4 and concentrated. Flash column chromatography on silica gel (heptane/ethyl acetate 10/1→2/1) gives 2.23 g of tert-butyl [cis-3-(methoxymethoxymethyl)cyclohexylmethoxy]acetate as a colorless oil.

C16H30O5 (302.41), MS (ESI): 320.30 (M+NH$_4^+$).

tert-Butyl [cis-3-(tert-butyldimethylsilanyloxymethyl)cyclohexylmethoxy]-acetate

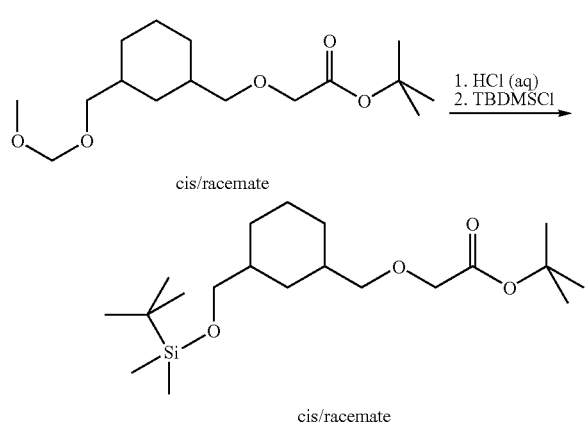

cis/racemate 1.9 g of tert-butyl [cis-3-(methoxymethoxymethyl)cyclohexylmethoxy]-acetate are dissolved in 10 ml of tetrahydrofuran, 5 ml of conc. HCl are added and the mixture is stirred at room temperature for 2 h. 10 ml of sat. NaCl solution, 10 ml of water and 30 ml of methyl tert-butyl ether are then added, the phases are separated and the aqueous phase is extracted with methyl tert-butyl ether. The combined organic phases are dried over MgSO4 and concentrated. Flash chromatography on silica gel (heptane/ethyl acetate 3/1) gives 600 mg of tert-butyl (cis-3-hydroxymethyl-cyclohexylmethoxy)acetate as a colorless oil (TLC (heptane/ethyl acetate 2/1): R$_{f, \text{starting material}}$=0.68, R$_{f, \text{product}}$=0.18). 260 mg of this are dissolved in 5 ml of dimethylformamide, and 170 mg of tert-butyidimethylsilyl chloride are added. The solution is then cooled to 0° C., and 160 mg of imidazole are added. The solution is stirred at room temperature for 15 h, and 20 ml of sat. NaCl solution, 10 ml of water and 30 ml of methyl tert-butyl ether are then added. The phases are separated and the organic phase is washed with sat. NaCl solution, dried over MgSO4 and concentrated. This gives 350 mg of tert-butyl [cis-3-(tert-butyldimethyl-silanyloxymethyl)cyclohexylmethoxy]acetate as a colorless oil.

C20H40O4Si (372.36); LCMS (ESI): 390.3 (M+NH4$^+$).

tert-Butyl 2-[cis-3-(tert-butyldimethylsilanyloxymethyl)cyclohexylmethoxy]-2-methylpropionate

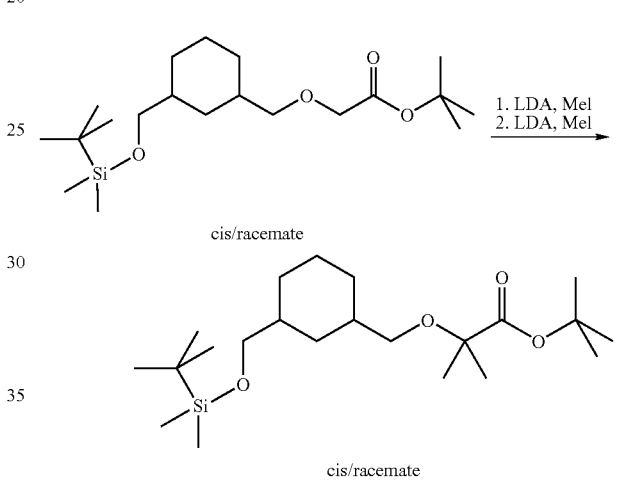

250 mg of tert-butyl [cis-3-(tert-butyidimethylsilanyloxymethyl)cyclohexyl-methoxy]acetate are dissolved in 10 ml of abs. tetrahydrofuran and cooled to −78° C. (dry ice/acetone bath). 1.70 ml of a 2M lithium diisopropylamide solution in tetrahydrofuran/hexane are then added dropwise. The solution is initially stirred at −78° C. for 20 min and then warmed to 0° C. (ice bath), and 950 mg of methyl iodide are added. The solution is stirred at 0° C. for 1 h. 1 ml of sat. NH4Cl solution and 10 ml of water are added, and the phases are separated. The aqueous phase is extracted with ethyl acetate. The combined organic phases are dried over MgSO4 and concentrated. The crude product is dissolved in 10 ml of abs. tetrahydrofuran and cooled to −78° C. (dry ice/acetone bath). 1.70 ml of a 2M lithium diisopropylamide solution in tetrahydrofuran/hexane are then added dropwise. The solution is initially stirred at −78° C. for 20 min and then warmed to 0° C. (ice bath), and 950 mg of methyl iodide are added. The solution is stirred at 0° C. for 1 h. 1 ml of sat. NH4Cl solution and 10 ml of water are added and the phases are separated. The aqueous phase is extracted with ethyl acetate. The combined organic phases are dried over MgSO4 and concentrated. This gives 220 mg of tert-butyl 2-[cis-3-(tert-butyldimethylsilanyloxymethyl)cyclo-hexylmethoxy]-2-methylpropionate as a light-yellow oil. TLC (heptane/ethyl acetate 4/1): R$_{f, \text{starting material}}$=0.66, R$_{f, \text{product}}$=0.80.

2-[cis-3-(5-Methyl-2-p-tolyloxazol-4-ylmethoxymethyl)cyclohexylmethoxy]-2-methylpropionic acid

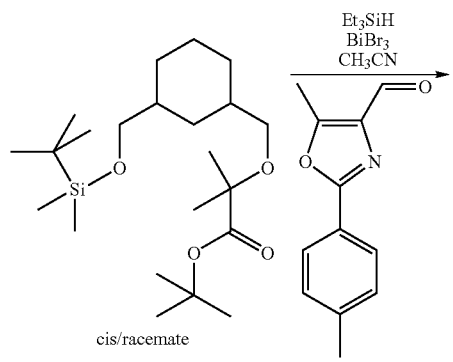

cis/racemate

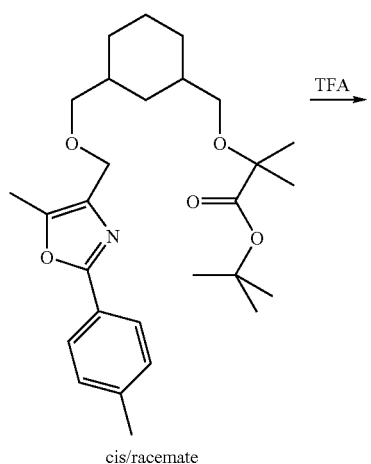

cis/racemate

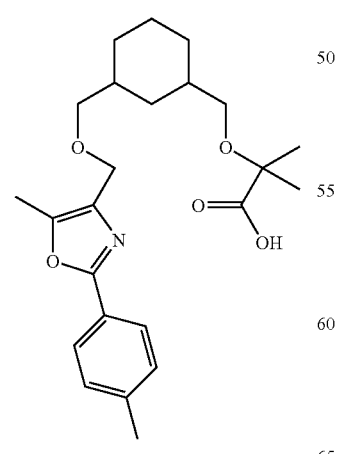

cis/racemate 50 mg of tert-butyl 2-[cis-3-(tert-butyldimethylsilanyloxymethyl)cyclohexyl-methoxy]-2-methylpropionate are added to a mixture of 20 mg of BiBr3 and 30 mg of HSiEt$_3$ in 0.5 ml of acetonitrile. 38 mg of 5-methyl-2-p-tolyloxazole-4-carbaldehyde in 0.2 ml of acetonitrile are added dropwise, and the mixture is stirred at room temperature overnight. The resulting black solid is filtered and the filtrate is concentrated and taken up in 1 ml of trifluoroacetic acid. The solution is stirred at room temperature overnight. The solvent is distilled off under reduced pressure and the residue is purified by HPLC. This gives 3.4 mg of 2-[cis-3-(5-methyl-2-p-tolyloxazol-4-ylmethoxymethyl)cyclohexylmethoxy]-2-methylpropionic acid as a colorless oil. C24H33NO5 (415.24); MS (ES−): 414.25 (M−H$^+$).

EXAMPLE 56

Analogously to Example 55, tert-butyl [cis-3-(methoxymethoxymethyl)cyclo-hexylmethoxy)acetate, methyl iodide, ethyl iodide and 5-methyl-2-p-tolyloxazole-4-carbaldehyde give 2-[cis-3-(5-methyl-2-p-tolyloxazol-4-ylmethoxymethyl)cyclohexylmethoxy]-3-methylbutyric acid. C25H35NO5 (429.25); MS (ES−): 428.22 (M−H$^+$).

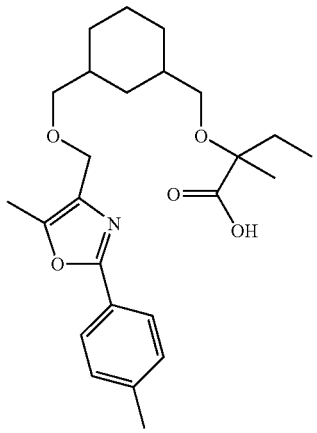

cis/diastereomer mixture

EXAMPLE 57
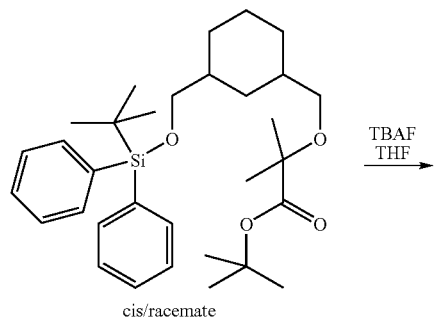
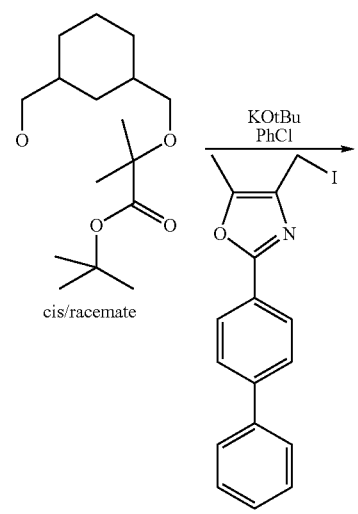
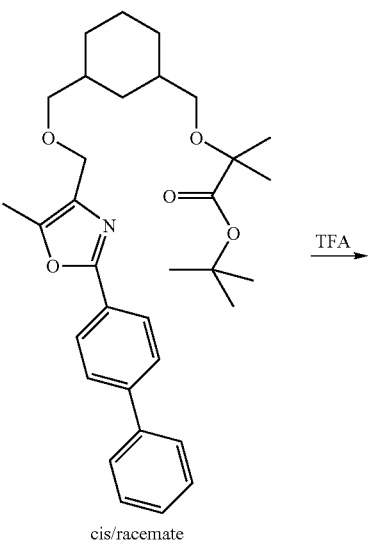
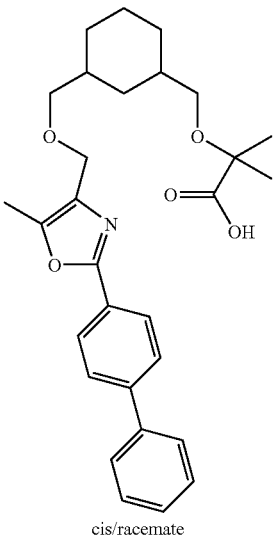
tert-Butyl 2-[cis-3-hydroxymethylcyclohexyl-methoxy]-2-methylpropionate
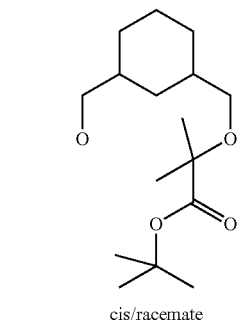

4.5 g of tert-butyl 2-[cis-3-(tert-butyidimethylsilany-loxymethyl)cyclohexyl-methoxy]-2-methylpropionate (synthesis analogously to tert-butyl 2-[cis-3-(tert-butyldimethyl-silanyloxymethyl)cyclohexylmethoxy]-2-methylpropionate in Example 55) are dissolved in 85 ml of THF, 2.24 g of TBAF trihydrate are added and the mixture is stirred at 60° C. for 90 min. Water and MTBE are added, the phases are separated and the organic phase is dried over MgSO4 and concentrated. The residue is chromatographed on silica gel (heptane/ethyl acetate 1:1), which gives 1.45 g of tert-butyl 2-[cis-3-hydroxymethylcyclohexylmethoxy]-2-methylpropionate. C16H30O4 (286.42), MS (ESI): 287 (MH+).

2-[cis-3-(5-Methyl-2-(4-biphenyl)oxazol-4-yl-methoxymethyl)cyclohexyl-methoxy]-2-methylpropionic acid

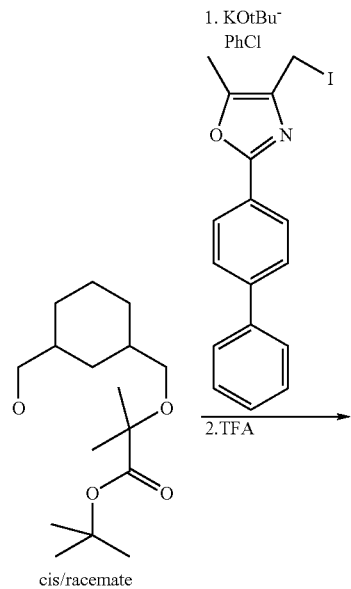

cis/racemate 50 mg of tert-butyl 2-[cis-3-hydroxymethylcyclohexyl-methoxy]-2-methylpropionate and 200 mg of 5-methyl-2-(4-biphenyl)oxazol-4-yl-methoxymethyl iodide are dissolved in 2 ml of chlorobenzene, and 59 mg of potassium tert-butoxide are added. The suspension is stirred at RT for 24 h, 2.5 ml of TFA are then added and the solution is stirred at RT for another 24 h. The solvent is distilled off under reduced pressure and the residue is purified by preparative HPLC, which gives 20 mg of 2-[cis-3-(5-methyl-2-(4-biphenyl)oxazol-4-ylmethoxymethyl)cyclohexylmethoxy]-2-methylpropionic acid. C29H35NO5 (477.61), MS (ESI): 478 (MH+).

EXAMPLE 58

Analogously to Example 57, tert-butyl 2-[cis-3-hydroxymethylcyclohexyl-methoxy]-2-methylpropionate and 5-methyl-2-phenyloxazol-4-ylmethoxy-methyl chloride give 2-[cis-3-(5-methyl-2-phenyloxazol-4-ylmethoxymethyl)-cyclohexylmethoxy]-2-methylpropionic acid. $C_{23}H_{31}NO_5$ (401.51); MS (ESI): 402 (MH$^+$).

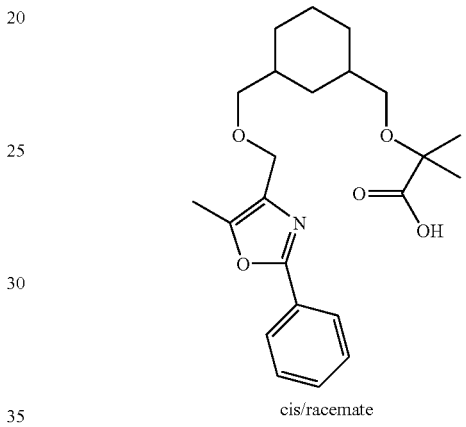

cis/racemate

EXAMPLE 59

Analogously to Example 57, tert-butyl 2-[cis-3-hydroxymethylcyclohexyl-methoxy]-2-methylpropionate and 5-methyl-2-naphthyloxazol-4-ylmethoxy-methyl chloride give 2-[cis-3-(5-methyl-2-naphthyloxazol-4-ylmethoxy-methyl)cyclohexylmethoxy]-2-methylpropionic acid. C27H33NO5 (451.57); MS (ESI): 458 (MH$^+$).

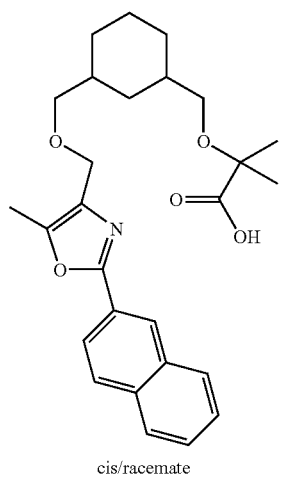

cis/racemate

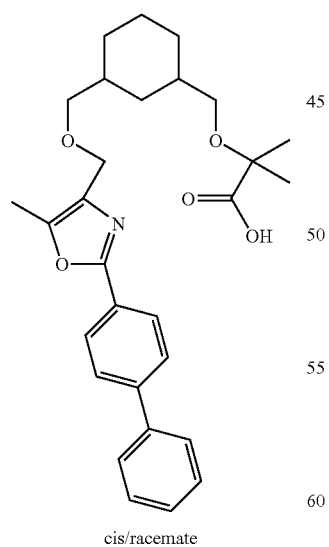

cis/racemate

EXAMPLE 60

Analogously to Example 57, tert-butyl 2-[cis-3-hydroxymethylcyclohexyl-methoxy]-2-methylpropionate and 5-ethyl-2-(3-methoxyphenyl)oxazol-4-yl-methoxymethyl chloride give 2-[cis-3-(5-ethyl-2-(3-methoxyphenyl)oxazol-4-ylmethoxymethyl)cyclohexylmethoxy]-2-methylpropionic acid. C25H35NO5 (445.56); MS (ESI): 446 (MH$^+$).

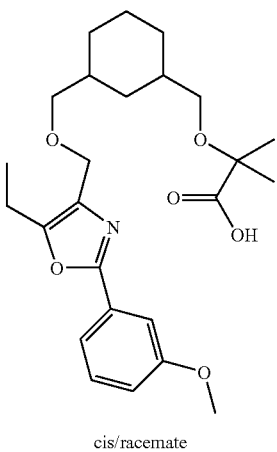

cis/racemate

EXAMPLE 61

Analogously to Example 57, tert-butyl 2-[cis-3-hydroxymethylcyclohexyl-methoxy]-2-methylpropionate and 5-methyl-2-(4-isopropylphenyl)-oxazol-4-ylmethoxymethyl chloride give 2-[cis-3-(5-ethyl-2-(4-isopropylphenyl)-oxazol-4-ylmethoxymethyl)cyclohexylmethoxy]-2-methylpropionic acid. C26H37NO5 (443.59); MS (ESI): 444 (MH$^+$).

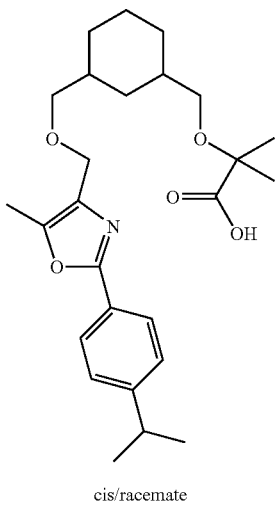

cis/racemate

EXAMPLE 62

Analogously to Example 57, tert-butyl 2-[cis-3-hydroxymethylcyclohexyl-methoxy]-2-methylpropionate and 5-cyclohexyl-2-p-tolyloxazol-4-yl-methoxymethyl chloride give 2-[cis-3-(5-ethyl-2-p-tolyloxazol-4-ylmethoxy-methyl)cyclohexylmethoxy]-2-methylpropionic acid. C29H41NO5 (483.65); MS (ESI): 484 (MH$^+$).

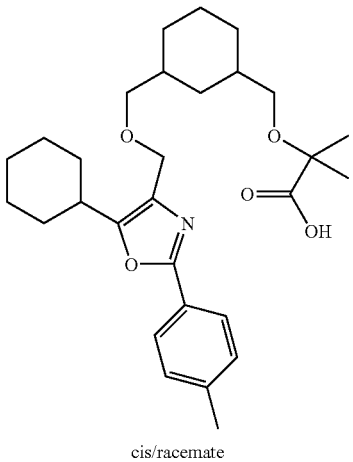

cis/racemate

EXAMPLE 63

Analogously to Example 57, tert-butyl 2-[cis-3-hydroxymethylcyclohexyl-methoxy]-2-methylpropionate and 5-ethyl-2-p-isopropyloxazol-4-ylmethoxy-methyl chloride give 2-[cis-3-(5-ethyl-2-p-isopropyloxazol-4-ylmethoxy-methyl)cyclohexylmethoxy]-2-methylpropionic acid. C27H39NO5 (457.62); MS (ESI): 458 (MH$^+$).

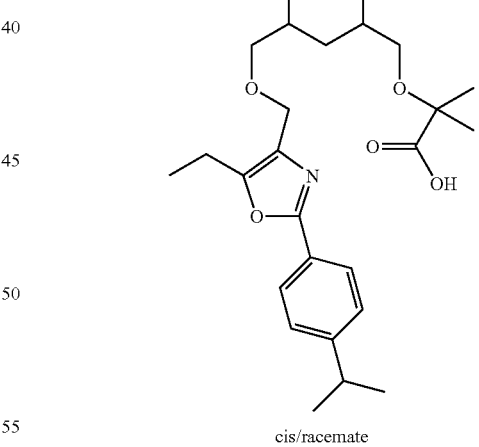

cis/racemate

EXAMPLE 64

Analogously to Example 57, tert-butyl 2-[cis-3-hydroxymethylcyclohexyl-methoxy]-2-methylpropionate and 5-ethyl-2-(2-naphthyl)oxazol-4-yl-methoxymethyl chloride give 2-[cis-3-(5-ethyl-2-(2-naphthyl)oxazol-4-yl-methoxymethyl)cyclohexylmethoxy]-2-methylpropionic acid. C28H35NO5 (465.59); MS (ESI): 466 (MH$^+$).

127

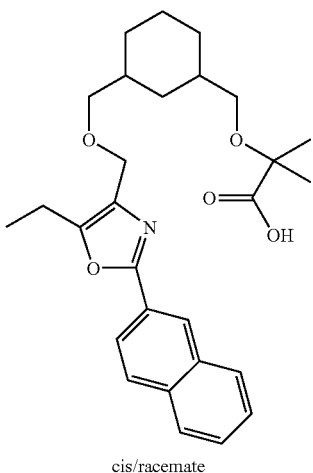
cis/racemate

EXAMPLE 65

Analogously to Example 57, tert-butyl 2-[cis-3-hydroxymethylcyclohexyl-methoxy]-2-methylpropionate and 5-ethyl-2-p-tolyloxazol-4-ylmethoxy-methyl chloride give 2-[cis-3-(5-ethyl-2-p-tolyloxazol-4-ylmethoxy-methyl)cyclohexylmethoxy]-2-methylpropionic acid. C25H35NO5 (429.56); MS (ESI): 430 (MH$^+$).

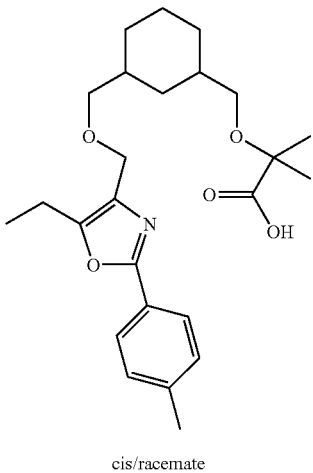
cis/racemate

EXAMPLE 66

Analogously to Example 57, tert-butyl 2-[cis-3-hydroxymethylcyclohexyl-methoxy]-2-methylpropionate and 5-ethyl-2-(3-trifluoromethyl)oxazol-4-yl-methoxymethyl chloride give 2-[cis-3-(5-ethyl-2-(3-trifluoromethyl)oxazol-4-ylmethoxymethyl)cyclohexylmethoxy]-2-methylpropionic acid. C26H34F3NO5 (497.56); MS (ESI): 498 (MH$^+$).

128

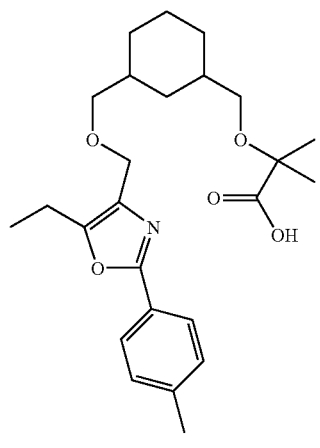
cis/racemate

EXAMPLE 67

4-{cis-3-[2-(3-Methoxyphenyl)-5-methyloxazol-4-ylmethoxy]cyclohexyl}-butyric acid

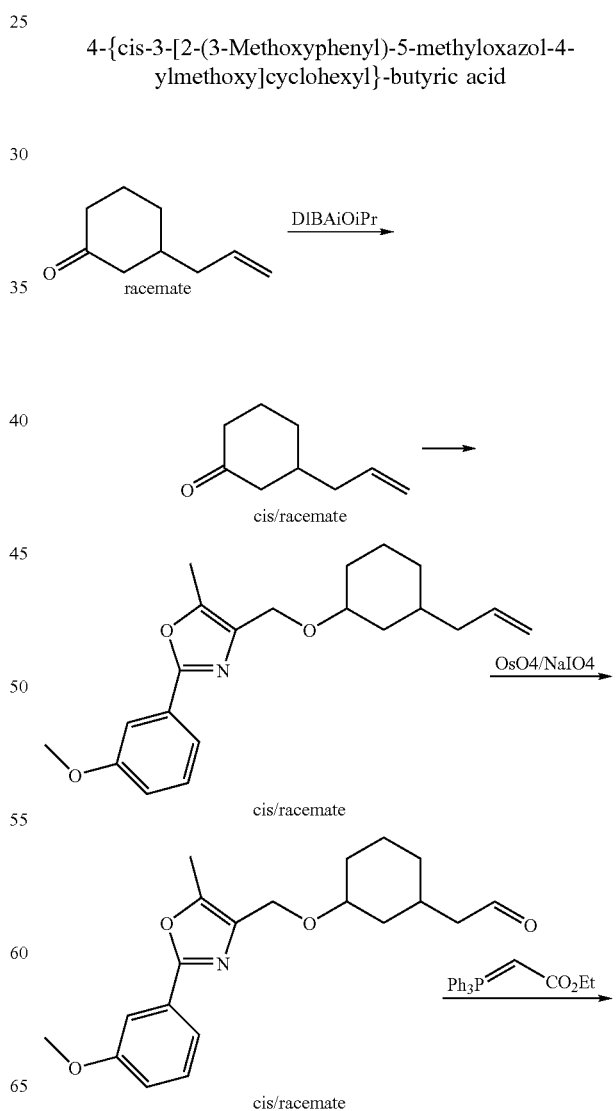

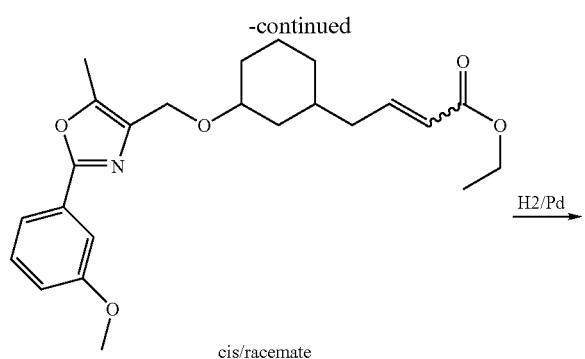

cis/racemate

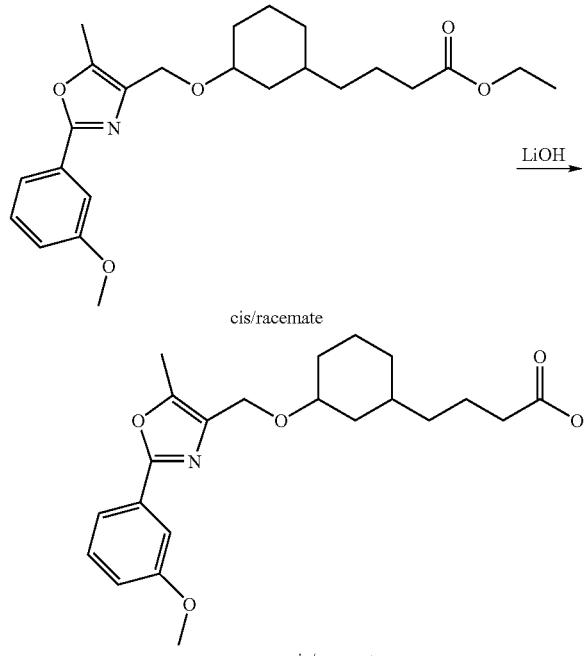

cis-3-Allylcyclohexanol

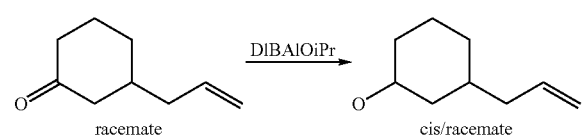

87 ml of a 1 molar solution of lithium diisobutylaluminum hydride in n-hexane are dissolved in 100 ml of diethyl ether, and 7 ml of isopropanol are added at 0° C. After the evolution of gas has ceased, 12.4 g of cis-3-allylcylohexanone, dissolved in 50 ml of diethyl ether, are added. The mixture is stirred at room temperature for 48 hours. The reaction mixture is quenched by addition of 1M HCl and the aqueous phase is saturated with sodium chloride and extracted five times with in each case 200 ml of ethyl acetate. The combined organic phases are washed with 2N NaOH and dried over MgSO4, and the solvent is then removed under reduced pressure. The residue is purified on silica gel using the mobile phase n-heptane:ethyl acetate=15:1=>5:1. This gives 6.8 g of cis-3-allylcyclohexanol as an oil. C9H16O (140.23), MS(ESI): 141 (M+H$^+$), R$_f$(n-heptane:ethyl acetate=2:1)=0.22.

4-(cis-3-Allylcyclohexyloxymethyl)-2-(3-methoxyphenyl)-5-methyloxazole

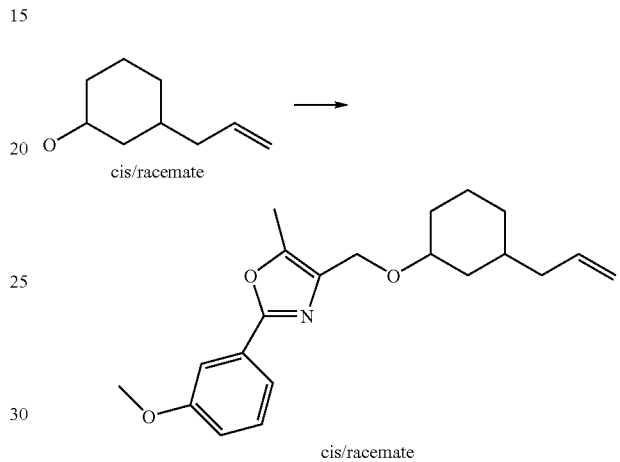

cis/racemate 1.8 g of cis-3-allylcyclohexanol are dissolved in 20 ml of dimethyl-formamide, and 770 mg of sodium hydride (60% strength suspension in paraffin oil) are added. After 30 minutes, 4 g of 4-iodomethyl-5-methyl-2-(3-methoxyphenyl)oxazole, dissolved in 20 ml of dimethylformamide, are added dropwise. The mixture is stirred at room temperature for 1 hour. 200 ml of methyl tert-butyl ether are then added to the reaction mixture, and the mixture is washed three times with water. The organic phase is dried over MgSO4 and the solvent is then removed under reduced pressure. The residue is purified on silica gel using the mobile phase n-heptane:ethyl acetate=10:1. This gives 750 mg of 4-(cis-3-allyl-cyclohexyloxymethyl)-2-(3-meLhoxpheny,"-5-methyloxazole as an Oil. C21H27NO3 (341.45), MS(ESI): 342 (M+H$^+$), R$_f$(n-heptane:ethyl acetate=2:1)=0.26.

{cis-3-[2-(3-Methoxyphenyl)-5-methyloxazol-4-ylmethoxy]cyclohexyl}-acetaldehyde

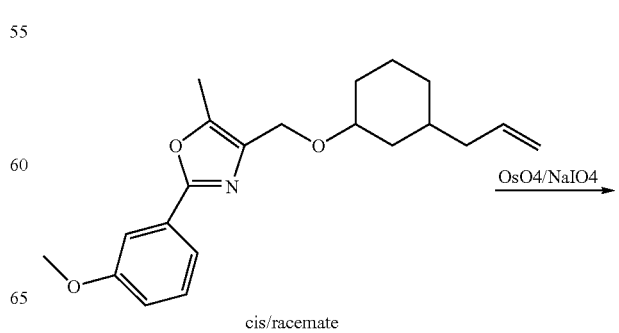

cis/racemate

-continued

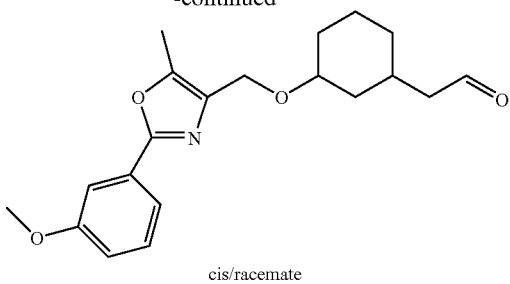

cis/racemate 750 mg of 4-(cis-3-allylcyclohexyloxymethyl)-2-(3-methoxyphenyl)-5-methyloxazole are dissolved in 20 ml of diethyl ether, and 1.4 g of sodium periodate, dissolved in 20 ml of water, are added. At 0° C., 1 ml of an osmium tetroxide solution (2.5% by weight in tert-butanol) is added, and the mixture is stirred vigorously at room temperature. After 8 hours, 100 ml of methyl tert-butyl ether are added and the mixture is washed with a saturated sodium thiosulfate solution. The organic phase is dried over MgSO4 and the solvent is then removed under reduced pressure. This gives 740 mg of {cis-3-[2-(3-methoxyphenyl)-5-methyloxazol-4-yl-methoxy]-cyclohexyl}acetaldehyde as a yellow-brown oil. C20H25NO4 (343.43), MS(ESI): 344 (M+H$^+$), R$_f$(n-heptane:ethyl acetate=2:1)=0.10.

Ethyl 4-{cis-3-[2-(3-methoxyphenyl)-5-methyloxazol-4-ylmethoxy]cyclo-hexyl}but-2-enoate

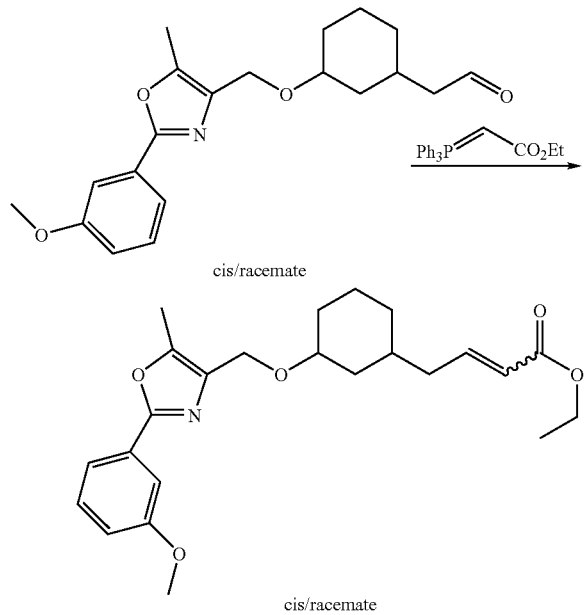

280 mg of {cis-3-[2-(3-methoxyphenyl)-5-methyloxazol-4-ylmethoxy]cyclo-hexyl}acetaldehyde are dissolved in 10 ml of dichloromethane, and 370 mg of ethyl (triphenylphosphoranylidene)acetate are added. The mixture is stirred at room temperature for 3 hours. The mixture is washed with saturated sodium chloride solution and dried over MgSO4, and the solvent is then removed under reduced pressure. The residue is purified on silica gel using the mobile phase n-heptane:ethyl acetate=5:1. This gives 190 mg of ethyl 4-{cis-3-[2-(3-methoxyphenyl)-5-methyloxazol-4-yl-methoxy]cyclohexyl}but-2-enoate as an oil. C24H31NO$_5$ (413.52), MS(ESI): 414 (M+H$^+$), R$_f$(n-heptane:ethyl acetate=2:1)=0.30.

Ethyl 4-{cis-3-[2-(3-methoxyphenyl)-5-methyloxazol-4-ylmethoxy]cyclo-hexyl}butyrate

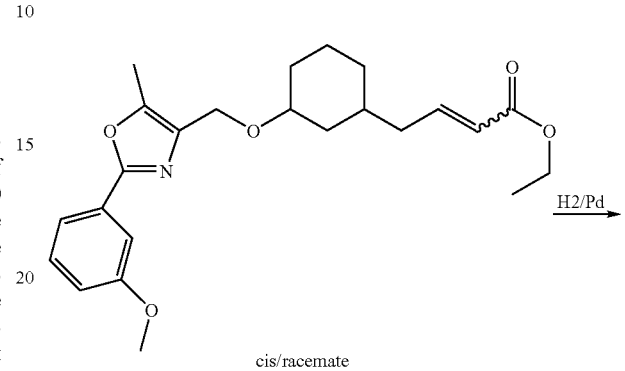

cis/racemate

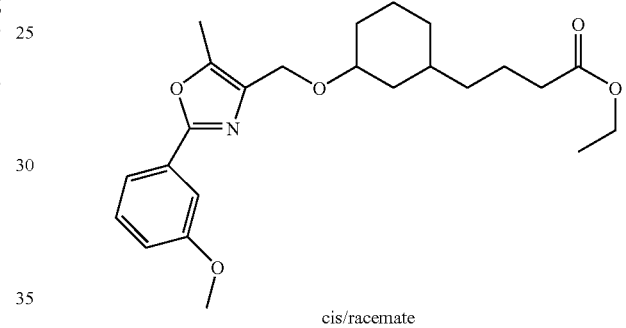

cis/racemate 190 mg of ethyl 4-{cis-3-[2-(3-methoxyphenyl)-5-methyloxazol-4-yl-methoxy]cyclohexyl}but-2-enoate are dissolved in 25 ml of methanol, and 20 mg of Pd (10% on activated carbon) are added. The mixture is stirred at room temperature and under an atmosphere of hydrogen for 7 hours. The catalyst is filtered off through Celite and the filtrate is concentrated under reduced pressure. This gives 110 mg of ethyl 4-{cis-3-[2-(3-methoxyphenyl)-5-methyloxazol-4-ylmethoxy]cyclohexyl}butyrate as an oil. C24H33NO5 (415.53), MS(ESI): 416 (M+H$^+$).

4-{cis-3-[2-(3-Methoxyphenyl)-5-methyloxazol-4-ylmethoxy]cyclohexyl}-butyric acid

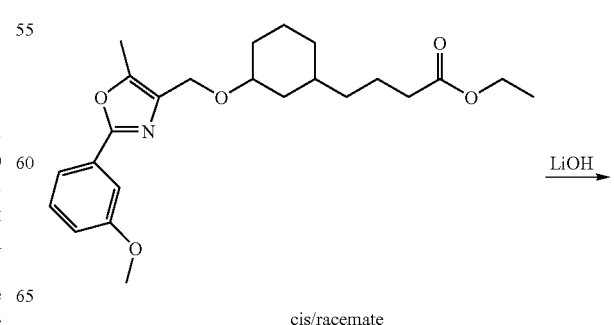

cis/racemate

-continued

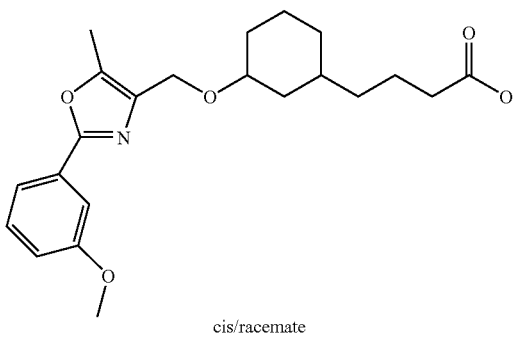

cis/racemate 110 mg of ethyl 4-{cis-3-[2-(3-methoxyphenyl)-5-methyloxazol-4-ylmethoxy]cyclohexyl}butyrate are dissolved in 5 ml of a mixture of tetrahydrofuran and water in a ratio of 2:1, and 20 mg of lithium hydroxide are added. The mixture is stirred at room temperature for 12 hours. The mixture is acidified by addition of 1 N HCl and extracted with ethyl acetate. The organic phase is dried over MgSO4, and the solvent is then removed under reduced pressure. The residue is purified by RP-HPLC. Freeze-drying gives 24 mg of 4-{cis-3-[2-(3-methoxyphenyl)-5-methyloxazol-4-ylmethoxy]cyclohexyl}butyric acid as a lyophilizate. C22H29NO5 (387.48), MS(ESI): 388 (M+H+).

EXAMPLE 68

Analogously to Example 67, {cis-3-[2-(3-methoxyphenyl)-5-methyloxazol-4-ylmethoxy]
cyclohexyl}acetaldehyde and ethyl 2-(triphenylphosphoranyl-idene)propionate gave 4-{cis-3-[2-(3-methoxyphenyl)-5-methyloxazol-4-ylmethoxy]cyclohexyl}-2-methylbutyric acid.

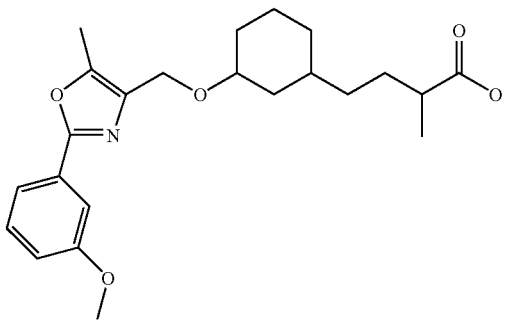

cis/diastereomer mixture

C23H31NO5 (401.51), MS(ESI): 402 (M+H+).

EXAMPLE 69

2-Ethyl-4-{cis-3-[2-(3-methoxyphenyl)-5-methyloxazol-4-ylmethoxy]cyclo-hexyl}butyric acid Ethyl 2-ethyl-4-{cis-3-[2-(3-methoxyphenyl)-5-methyloxazol-4-ylmethoxy]-cyclohexyl}but-2-enoate

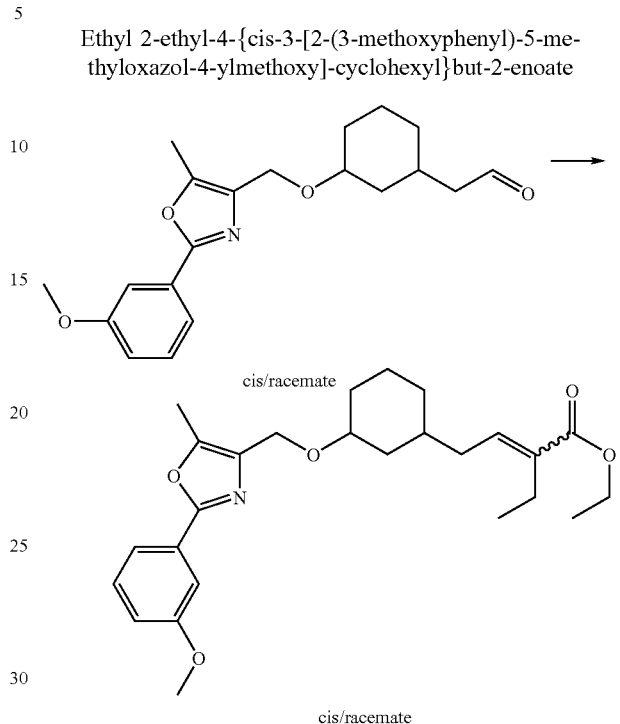

cis/racemate 0.4 ml of triethyl phosphonobutyrate is dissolved in 5 ml of tetrahydrofuran, and 0.5 ml of a 2.5 M n-butyllithium solution in n-hexane is added at −20° C.

The mixture is stirred at −20° C. for 1 hour, and 386 mg of {cis-3-[2-(3-methoxyphenyl)-5-methyloxazol-4-ylmethoxy]cyclohexyl}acetaldehyde, dissolved in 4 ml of tetrahydrofuran, are then added. After 30 minutes, the reaction mixture is slowly warmed to room temperature, 0.5 ml of water is added, the residue is diluted with ethyl acetate and dried over MgSO4 and the solvent is then removed under reduced pressure. This gives 750 mg of ethyl 2-ethyl-4-{cis-3-[2-(3-methoxyphenyl)-5-methyloxazol-4-yl-methoxy]-cyclohexyl}but-2-enoate as an oil. C26H35NO5 (441.57), MS(ESI): 442 (M+H+).

Analogously to Example 67, ethyl 2-ethyl-4-{cis-3-[2-(3-methoxyphenyl)-5-methyloxazol-4-ylmethoxy]
cyclohexyl}but-2-enoate gave 2-ethyl-4-{cis-3-[2-(3-methoxyphenyl)-5-methyloxazol-4-ylmethoxy]
cyclohexyl}butyric acid.

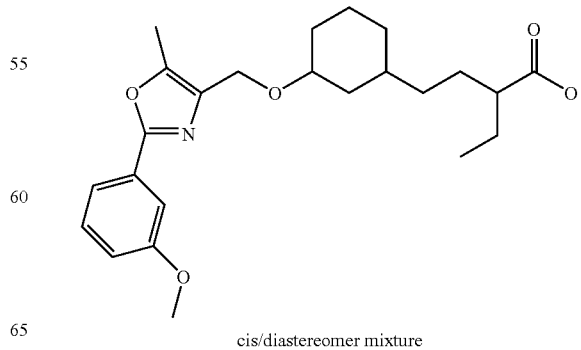

cis/diastereomer mixture

C24H33NO5 (415.53), MS(ESI): 416 (M+H+).

EXAMPLE 70
Analogously to Example 69, {cis-3-[2-(3-methoxyphenyl)-5-methyloxazol-4-ylmethoxy]cyclohexyl}acetaldehyde and triethyl phosphonopentanoate gave 2-(2-{cis-3-[2-(3-methoxyphenyl)-5-methyloxazol-4-ylmethoxy]cyclo-hexyl}ethyl)pentanoic acid.
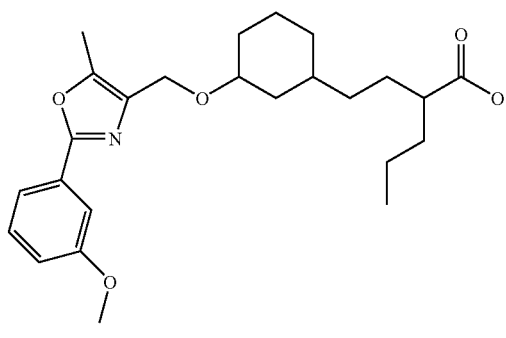
cis/diastereomer mixture
C25H35NO5 (429.56), MS(ESI): 430 (M+H$^+$).
EXAMPLE 71
2,2-Dimethyl-4-[cis-3-(5-netgtk-2-p-tolyloxazol-4-ylmethoxy)cyclohexyl]-butyric Acid
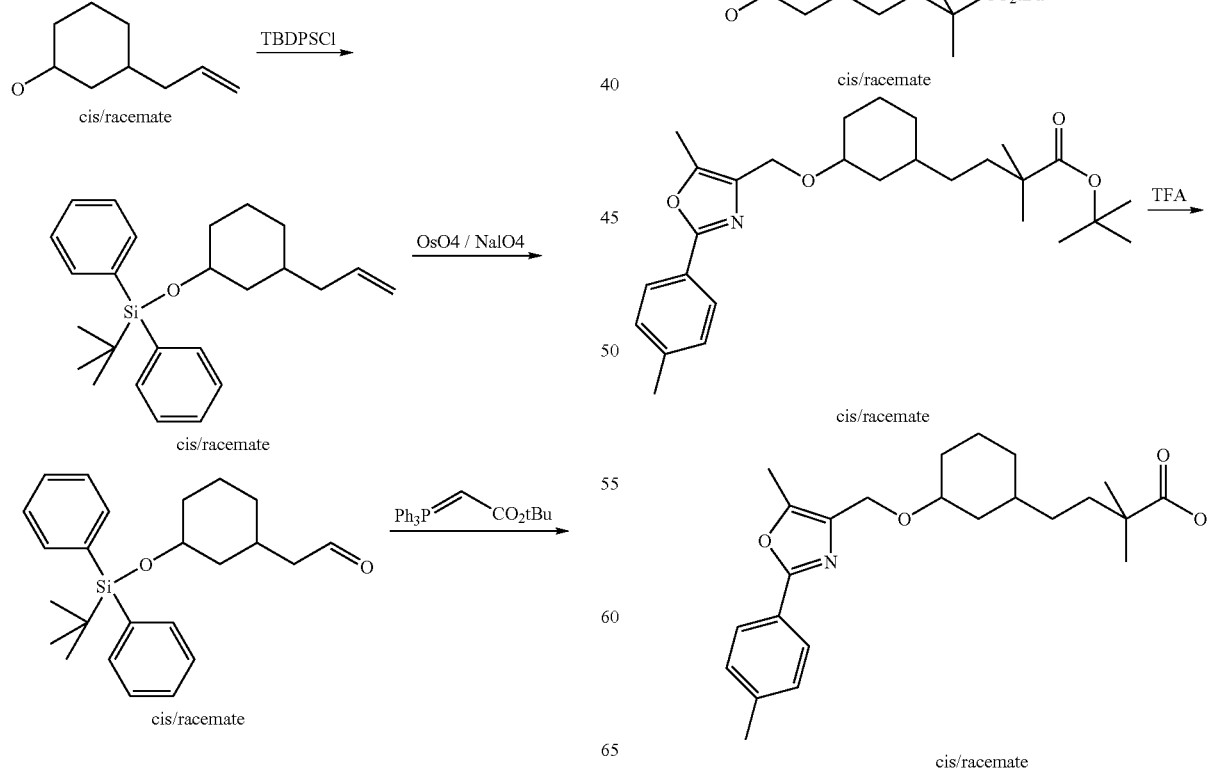

(cis-3-Allylcyclohexyloxy)-tert-butyldiphenylsilane

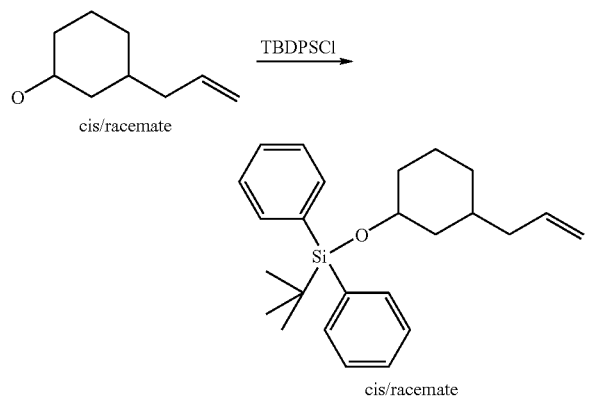

6.8 g of cis-3-allylcyclohexanol are, together with 15 ml of tert-butyl-diphenylsilyl chloride, 5 g of imidazole and 200 mg of dimethyl-aminopyridine, dissolved in 100 ml of dimethylformamide, and the mixture is stirred at room temperature for 12 h. 400 ml of methyl tert-butyl ether are added to the reaction mixture, and the mixture is washed three times with water. The organic phase is dried over MgSO4 and the solvent is then removed under reduced pressure. This gives 20.5 g of (cis-3-allylcyclohexyloxy)-tert-butyl-diphenyl-silane as an oil. C25H34OSi (378.64), MS(ESI): 379 (M+H$^+$), R$_f$(n-heptane:ethyl acetate=2:1)=0.93.

[cis-3-(tert-butyldiphenylsilanyloxy)cyclohexyl]acetaldehyde

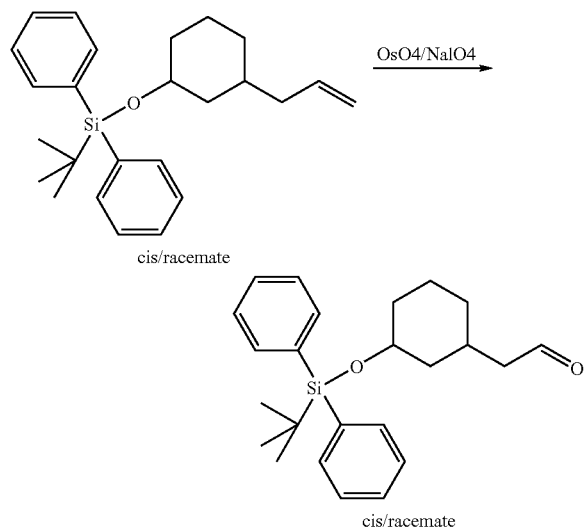

5.5 g of (cis-3-allylcyclohexyloxy)-tert-butyl-diphenyl-silane are dissolved in 100 ml of diethyl ether, and 9.4 g of sodium periodate, dissolved in 100 ml of water, are added. At 0° C., 15 ml of an osmium tetroxide solution (2.5% by weight in tert-butanol) are added, and the mixture is stirred vigorously at room temperature. After 5 hours, a further 5 g of sodium periodate are added, and the mixture is stirred at room temperature for another 3 hours. The reaction mixture is then diluted by addition of 300 ml of methyl tert-butyl ether and washed with saturated sodium thiosulfate solution. The organic phase is dried over MgSO4 and the solvent is then removed under reduced pressure. This gives 6 g of [cis-3-(tert-butyldiphenylsilanyloxy)-cyclohexyl]acetaldehyde as a yellow-brown oil.

C24H32O2Si (380.61), MS(ESI): 381 (M+H$^+$), R$_f$(n-heptane:ethyl acetate=5:1)=0.44.

tert-Butyl 4-[cis-3-(tert-butyldiphenylsilanyloxy)cyclohexyl]but-2-enoate

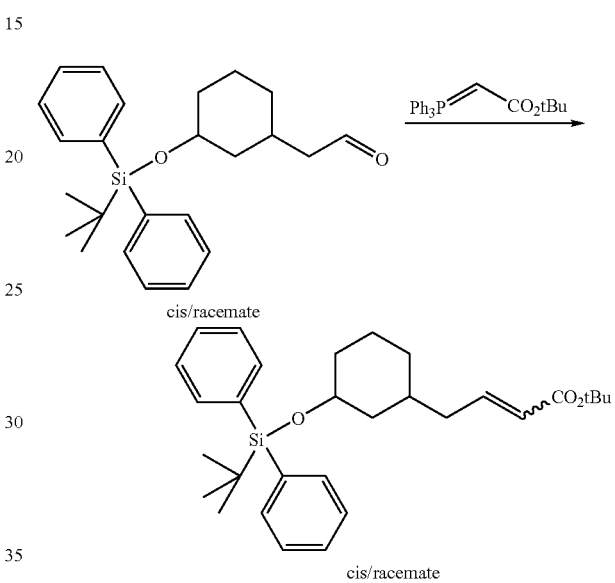

3.4 g of [cis-3-(tert-butyldiphenylsilanyloxy)cyclohexyl]acetaldehyde are dissolved in 100 ml of dichloromethane, and 5 g of tert-butyl (triphenylphosphoranylidene)acetate are added. Under reflux, the mixture is heated at the boil for 1 hour. The mixture is washed with saturated sodium chloride solution and dried over MgSO4, and the solvent is then removed under reduced pressure. The residue is purified on silica gel using the mobile phase n-heptane:ethyl acetate=20:1. This gives 2.4 g of tert-butyl 4-[cis-3-(tert-butyldiphenylsilanyloxy)cyclohexyl]but-2-enoate as an oil. C30H42O3Si (478.75), MS(ESI): 479 (M+H$^+$), R$_f$(n-heptane:ethyl acetate=5:1)=0.56.

tert-Butyl 4-[cis-3-(tert-butyldiphenylsilanyloxy)cyclohexyl]butanoate

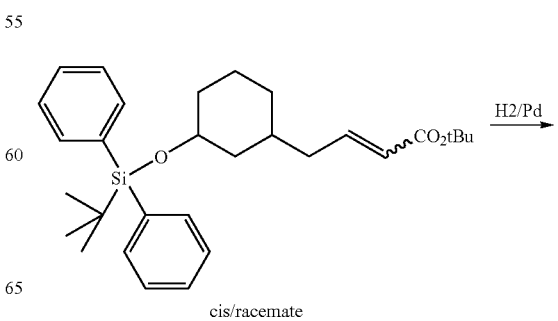

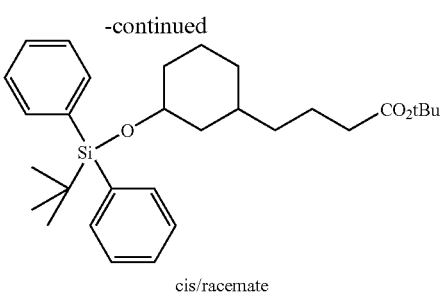

cis/racemate 2.4 g of tert-butyl 4-[cis-3-(tert-butyldiphenylsilanyloxy)cyclohexyl]but-2-enoate are dissolved in 35 ml of methanol, and 200 mg of PD (10% on activated carbon) are added. At room temperature, the mixture is stirred under an atmosphere of hydrogen for 7 hours. The catalyst is filtered off through Celite and the filtrate is concentrated under reduced pressure. This gives 2.3 g of tert-butyl 4-[cis-3-(tert-butyldiphenylsilanyloxy)cyclohexyl]-butanoate as an oil. C30H44O3Si (480.75), MS(ESI): 481 (M+H+).

tert-Butyl 4-[cis-3-(tert-butyldiphenylsilanyloxy)cyclohexyl]-2,2-dimethyl-butyrate

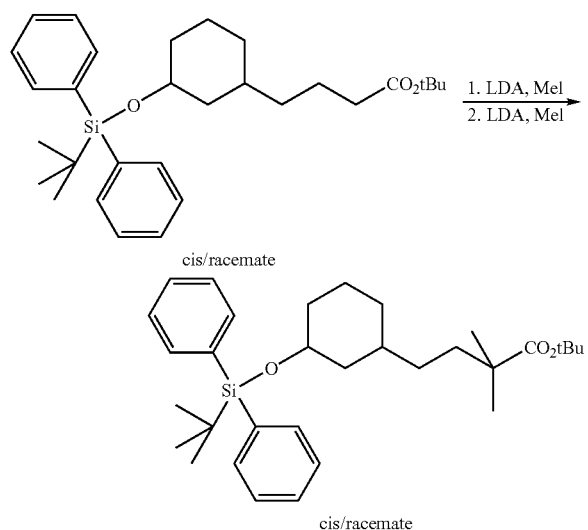

2 g of tert-butyl 4-[cis-3-(tert-butyidiphenylsilanyloxy)cyclohexyl]butanoate are dissolved in 20 ml of tetrahydrofuran, and 3.1 ml of a 2M solution of lithium diisopropylamide in tetrahydrofuran are added at −78° C. The reaction mixture is stirred at −78° C. for 2 hours and then warmed to −30° C., and 1.6 ml of methyl iodide are added. Over a period of 12 hours, the mixture is allowed to warm to room temperature. The reaction mixture is then diluted by addition of 150 ml of methyl tert-butyl ether and washed with saturated NaCl solution. The organic phase is dried over MgSO4 and the solvent is then removed under reduced pressure. The residue is purified on silica gel using the mobile phase n-heptane:ethyl acetate=10:1. This gives 2.1 g of the monomethylated product. This product is dissolved in 20 ml of tetrahydrofuran, and 6 ml of a 2M solution of lithium diisopropylamide in tetrahydrofuran are added at −78° C. The reaction mixture is stirred at −78° C. for 2 hours and then warmed to 0° C., and, after 10 minutes at 0° C., 2.5 ml of methyl iodide are added. Over a period of 12 hours, the mixture is allowed to warm to room temperature. The reaction mixture is then diluted by addition of 150 ml of methyl tert-butyl ether and washed with saturated NaCl solution. The organic phase is dried over MgSO4 and the solvent is then removed under reduced pressure. The residue is purified on silica gel using the mobile phase n-heptane:ethyl acetate=10:1. This gives 1.8 g of tert-butyl 4-[cis-3-(tert-butyidiphenylsilanyloxy)cyclohexyl]-2,2-dimethylbutyrate as an oil.

C32H48O3Si (508.82), R$_f$(n-heptane:ethyl acetate=5:1) =0.49.

tert-Butyl 4-(cis-3-hydroxycyclohexyl)-2,2-dimethylbutyrate

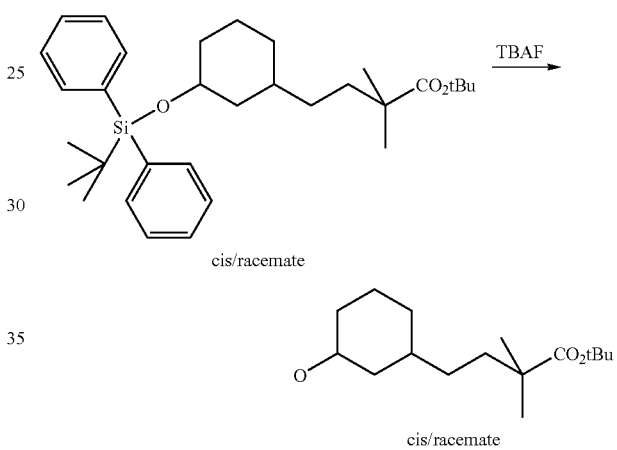

2 g of tert-butyl 4-[cis-3-(tert-butyldiphenylsilanyloxy)cyclohexyl]-2,2-dimethylbutyrate are dissolved in 10 ml of tetrahydrofuran, and 8 ml of a 1 M solution of tetrabutylammonium fluoride in tetrahydrofuran are added.

The mixture is stirred at 60° C. for 2 hours. The reaction mixture is concentrated under reduced pressure and purified on silica gel using the mobile phase n-heptane:ethyl acetate=20:1=>1:1. This gives 730 mg of tert-butyl 4-(cis-3-hydroxycyclohexyl)-2,2-dimethylbutyrate as an oil.

C16H30O3 (270.42), R$_f$(n-heptane:ethyl acetate=5:1) =0.22.

tert-Butyl 2,2-dimethyl-4-[cis-3-(5-methyl-2-p-tolyloxazol-4-ylmethoxy)cyclo-hexyl]butyrate

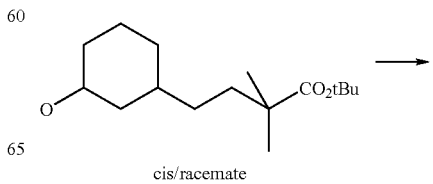

cis/racemate

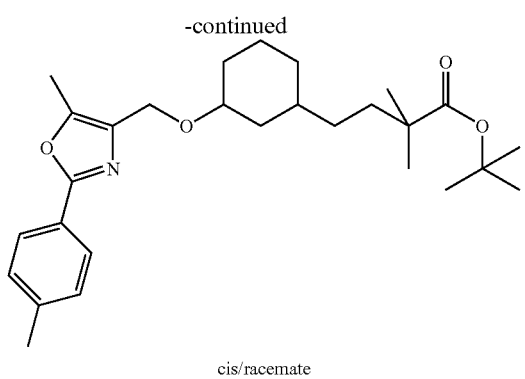

cis/racemate 365 mg of tert-butyl 4-(cis-3-hydroxycyclohexyl)-2,2-dimethylbutyrate are, together with 850 mg of 4-iodomethyl-5-methyl-2-(4 methylphenyl)oxazole, dissolved in 5 ml of dimethylformamide, and 110 mg of sodium hydride (60% strength in paraffin) are added. After 1 hour of stirring at room temperature, 100 ml of methyl tert-butyl ether are added and the reaction mixture is washed three times with water. The organic phase is dried over MgSO4 and the solvent is then removed under reduced pressure. The residue is purified by RP-HPLC. This gives 330 mg of tert-butyl 2,2-dimethyl-4-[cis-3-(5-methyl-2-p-tolyloxazol-4-ylmethoxy)cyclohexyl]butyrate as a white solid. C28H41NO4 (455.64), MS(ESI): 456 (M+H$^+$).

2,2-Dimethyl-4-[cis-3-(5-methyl-2-p-tolyloxazol-4-ylmethoxy)cyclohexyl]-butyric Acid

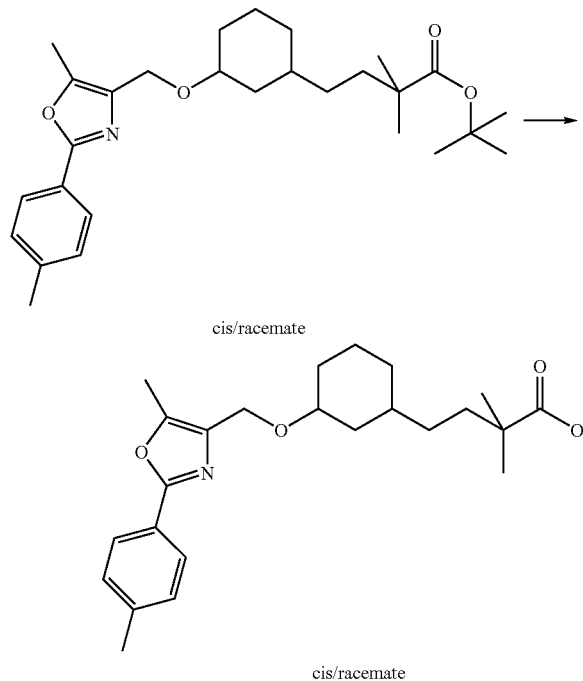

cis/racemate 300 mg of tert-butyl 2,2-dimethyl-4-[cis-3-(5-methyl-2-p-tolyloxazol-4-ylmethoxy)cyclohexyl]butyrate are dissolved in 20 ml of dichloromethane, and 10 ml of trifluoroacetic acid are added. The reaction mixture is stirred at room temperature for 1 hour. 200 ml of toluene are added and the solvents are then concentrated under reduced pressure. The residue is purified by RP-HPLC. This gives 180 mg of 2,2-dimethyl-4-[cis-3-(5-methyl-2-p-tolyloxazol-4-ylmethoxy)cyclohexyl]butyric acid as an oil. C$_{24}$H$_{33}$NO4 (399.53), MS(ESI): 400 (M+H$^+$).

EXAMPLE 72

Analogously to Example 71, tert-butyl 4-(cis-3-hydroxycyclohexyl)-2,2-dimethylbutyrate and 4-iodomethyl-5-methyl-2-(3-trifluoromethylphenyl)-oxazole gave 2,2-dimethyl-4-{3-[5-methyl-2-(3-trifluoromethylphenyl)oxazol-4-ylmethoxy]cyclohexyl}butyric acid.

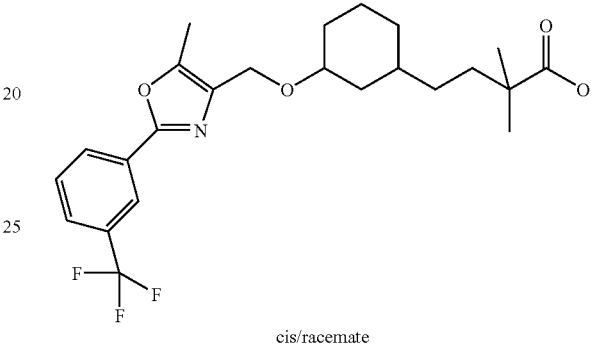

cis/racemate

C24H30F3NO4 (453.50), MS(ESI): 454 (M+H$^+$).

EXAMPLE 73

3-Methyl-2-{2-[cis-3-(5-methyl-2-p-tolyloxazol-4-ylmethoxy)cyclohexyl]-ethyl}butyric Acid tert-Butyl 2-(diethoxyphosphoryl)-3-methylbutyrate

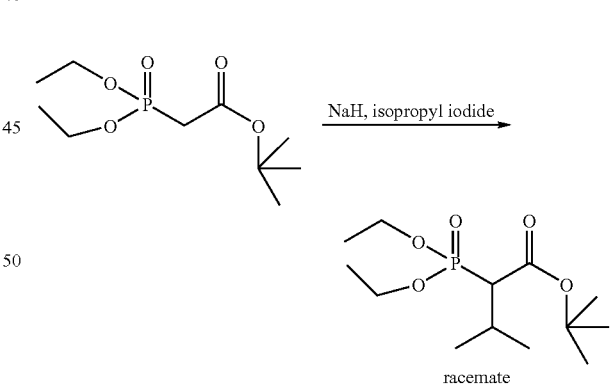

racemate 5.5 ml of tert-butyl diethylphosphonoacetate are dissolved in 20 ml of dimethylformamide, and 820 mg of sodium hydride (60% strength in paraffin oil) are added a little at a time at 0° C. The suspension is stirred at 0° C. for 15 minutes, and 2.4 ml of isopropyl iodide are then added. The mixture is stirred at room temperature for 12 hours. 250 ml of ethyl acetate are then added, and the reaction mixture is washed three times with in each case 150 ml of water. The organic phase is dried over MgSO4 and concentrated under reduced pressure. The residue is purified on silica gel using the mobile phase n-heptane:ethyl acetate=5:1. This gives 4.2 g of tert-butyl 2-(diethoxyphosphoryl)-3-methylbutyrate as an oil. C13H27O5P (294.33), MS(ESI): 239 (M-C₄H₈+H⁺), R_f(n-heptane:ethyl acetate=1:1)=0.34.

tert-Butyl 4-[cis-3-(tert-butyldiphenylsilanyloxy)cyclohexyl]-2-isopropylbutyr-2-enoate

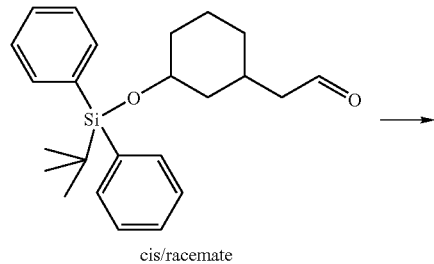

cis/racemate

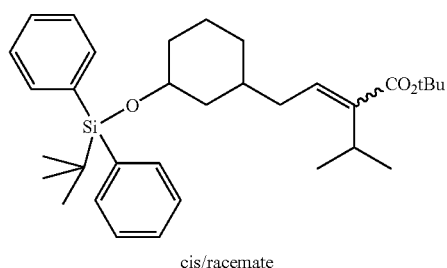

cis/racemate 770 mg of tert-butyl 2-(diethoxyphosphoryl)-3-methylbutyrate are dissolved in 10 ml of tetrahydrofuran, and 0.73 ml of a 2.7 M solution of n-butyllithium in n-hexane is added at −20° C. After 1 hour of stirring at −20° C., 500 mg of [cis-3-(tert-butyldiphenylsilanyloxy)cyclohexyl]acetaldehyde, dissolved in 5 ml of tetrahydrofuran, are added dropwise. The reaction mixture is slowly warmed to room temperature. 20 ml of water are then added, and the mixture is extracted three times with in each case 50 ml of ethyl acetate. The combined organic phases are dried over MgSO4 and the solvent is then removed under reduced pressure. The residue is purified on silica gel using the mobile phase n-heptane:ethyl acetate=30:1. This gives 340 mg of tert-butyl 4-[cis-3-(tert-butyldiphenylsilanyloxy)cyclohexyl]-2-isopropyl-butyr-2-enoate as an oil. C33H48O3Si (520.83), R_f(n-heptane:ethyl acetate=5:1)=0.70.

4-[cis-3-(tert-Butyldiphenylsilanyloxy)cyclohexyl]-2-isopropylbutyric Acid

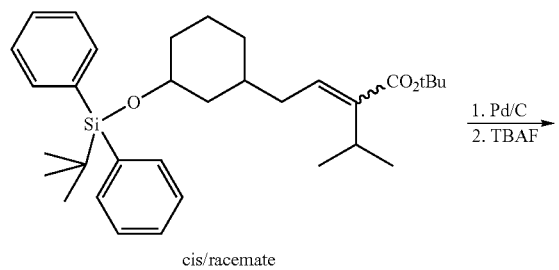

cis/racemate

-continued

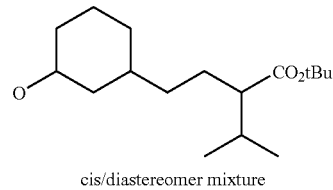

cis/diastereomer mixture 1.5 g of tert-butyl 4-[cis-3-(tert-butyldiphenylsilanyloxy)cyclohexyl]-2-isopropylbutyr-2-enoate are dissolved in 30 ml of ethyl acetate, and 200 mg of Perlman's catalyst are added. The mixture is stirred under an atmosphere of hydrogen (5 bar) for 5 hours. The catalyst is filtered off through Celite and the filtrate is concentrated under reduced pressure. The residue is dissolved in 15 ml of tetrahydrofuran, and 3 ml of a 1 M solution of tetrabutylammonium fluoride in tetrahydrofuran are added. The mixture is stirred at 60° C. for 2 hours. The reaction mixture is concentrated under reduced pressure and purified on silica gel using the mobile phase n-heptane:ethyl acetate=40:1=>10:1. This gives 400 mg of 4-[cis-3-(tert-butyidiphenylsilanyloxy)cyclohexyl]-2-isopropylbutyric acid as an oil.

C17H32O3 (284.44), MS(ESI): 211 (M−C₄H₉O⁻), R_f(n-heptane:ethyl acetate=10:1)=0.15.

Analogously to Example 73, 4-iodomethyl-5-methyl-2-(4-methylphenyl)-oxazole and 4-[cis-3-(tert-butyldiphenylsilanyloxy)cyclohexyl]-2-isopropyl-butyric acid gave 3-methyl-2-{2-[cis-3-(5-methyl-2-p-tolyloxazol-4-yl-methoxy)cyclohexyl]ethyl}butyric acid.

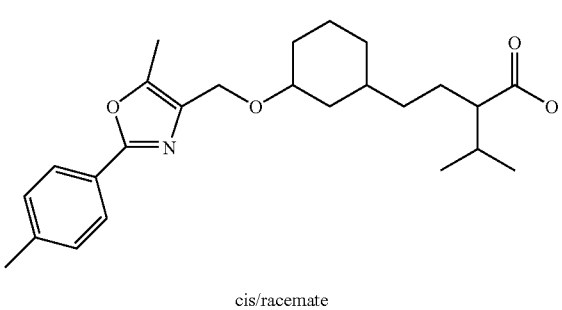

cis/racemate

C25H35NO4 (413.56), MS(ESI): 414 (M+H⁺).

EXAMPLE 74

Analogously to Example 73, 4-iodomethyl-5-methyl-2-(3 methoxyphenyl)-oxazole and 4-[cis-3-(tert-butyldiphenylsilanyloxy)cyclohexyl]-2-isopropyl-butyric acid gave 2-(2-{cis-3-[2-(3-methoxyphenyl)-5-methyloxazol-4-ylmethoxy]cyclohexyl}ethyl)-3-methylbutyric acid.

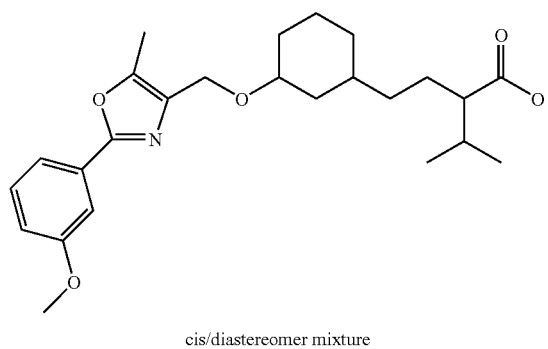

cis/diastereomer mixture

C25H35NO5 (429.56), MS(ESI): 430 (M+H+).

EXAMPLE 75

2-Benzyl-4-[cis-3-(5-methyl-2-p-tolyloxazol-4-ylmethoxy)cyclohexyl]butyric Acid

Analogously to Example 73, tert-butyl diethylphosphonoacetate and benzyl bromide gave tert-butyl 2-(diethoxyphosphoryl)-3-phenylpropionate

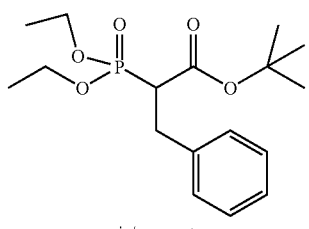

cis/racemate

C17H27O5P (342.38), R$_f$(n-heptane:ethyl acetate=1:1) =0.53.

Analogously to Example 73, tert-butyl 2-(diethoxyphosphoryl)-3-phenylpropionate, [cis-3-(tert-butyldiphenylsilanyloxy)cyclohexyl]-acetaldehyde and 4-iodomethyl-5-methyl-2-(4 methylphenyl)oxazole gave 2-benzyl-4-[cis-3-(5-methyl-2-p-tolyloxazol-4-ylmethoxy)cyclohexyl]butyric acid.

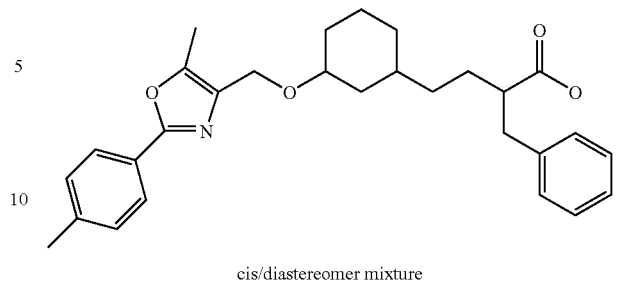

cis/diastereomer mixture

C29H35NO4 (461.61), MS(ESI): 462 (M+H+).

EXAMPLE 76

4-Methyl-2-{2-[cis-3-(5-methyl-2-p-tolyloxazol-4-ylmethoxy)cyclohexyl]-ethyl}pentanoic Acid Analogously to Example 73, tert-butyl 4-[cis-3-(tert-butyldiphenylsilanyloxy)cyclohexyl]butanoate, 3-bromo-2-methylpropene and 4-iodomethyl-5-methyl-2-(4 methylphenyl)oxazole gave tert-butyl 4-methyl-2-{2-[cis-3-(5-methyl-2-p-tolyloxazol-4-ylmethoxy)cyclohexyl]ethyl}pent-4-enoate.

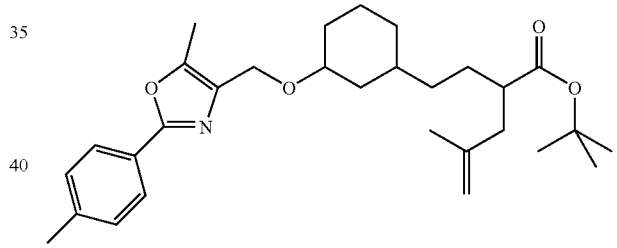

cis/diastereomer mixture

C30H43NO4 (481.68), MS(ESI): 482 (M+H+).

4-Methyl-2-{2-[cis-3-(5-methyl-2-p-tolyloxazol-4-ylmethoxy)cyclo-hexyl]ethyl}pentanoic acid

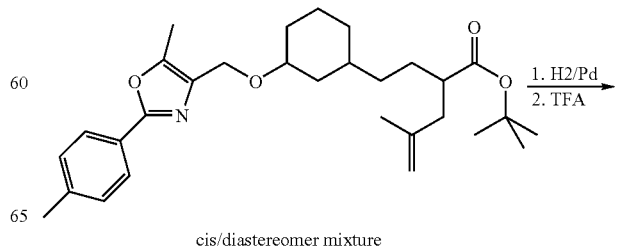

cis/diastereomer mixture

-continued

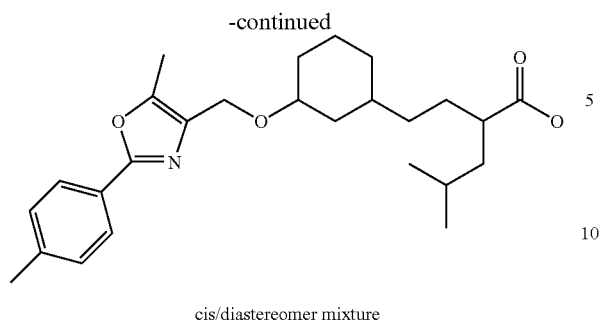

cis/diastereomer mixture 500 mg of tert-butyl 4-methyl-2-{2-[cis-3-(5-methyl-2-p-tolyloxazol-4-ylmethoxy)cyclohexyl]ethyl}pent-4-enoate are dissolved in 20 ml of ethyl acetate, and 50 mg of palladium (10% on activated carbon) are added. The mixture is stirred under an atmosphere of hydrogen (5 bar) for 5 hours. The catalyst is filtered off through Celite and the filtrate is concentrated under reduced pressure. The residue is dissolved in 20 ml of dichloromethane, and 10 ml of trifluoroacetic acid are added. The mixture is stirred at room temperature for 1 hour. 100 ml of toluene are added, and the solvents are then removed under reduced pressure. The residue is purified by RP-HPLC. This gives 100 mg of 4-methyl-2-{2-[cis-3-(5-methyl-2-p-tolyloxazol-4-ylmethoxy)cyclohexyl]ethyl}pentanoic acid as an oil. C26H37NO4 (427.59), MS(ESI): 428 (M+H+).

EXAMPLE 77

2-(2-{cis-3-[5-Methyl-2-(3-trifluoromethylphenyl)oxazol-4-ylmethoxy]cyclo-hexyl}ethyl)-2-propyl-pentanoic acid Analogously to Example 71, tert-butyl 4-[cis-3-(tert-butyldiphenylsilanyloxy)cyclohexyl]butanoate and allyl bromide gave tert-butyl 2-allyl-2-{2-[3-(tert-butyldiphenylsilanyloxy)cyclohexyl]ethyl}pent-4-enoate.

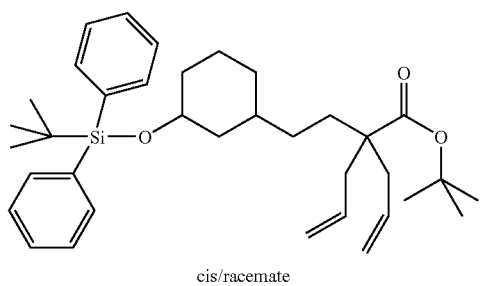

cis/racemate

C36H52O3Si (560.90), R$_f$(n-heptane:ethyl acetate=20:1) =0.60.

Analogously to Example 71 and Example 76, tert-butyl 2-allyl-2-{2-[cis-3-(tert-butyldiphenylsilanyloxy)cyclohexyl]ethyl}pent-4-enoate and 4-iodomethyl-5-methyl-2-(3-trifluoromethylphenyl)oxazole gave 2-(2-{cis-3-[5-methyl-2-(3-trifluoromethylphenyl)oxazol-4-ylmethoxy]cyclohexyl}ethyl)-2-propylpentanoic acid.

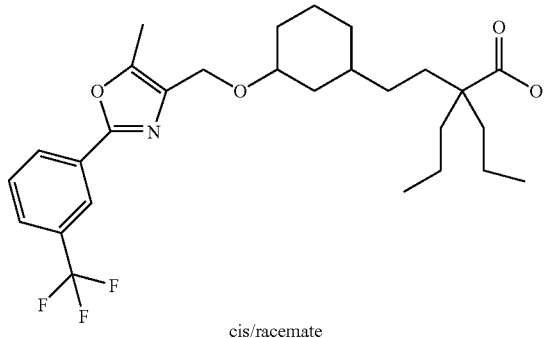

cis/racemate

C28H38F3NO4 (509.61), MS(ESI): 510 (M+H+).

EXAMPLE 78

1-{2-[cis-3-(5-Methyl-2-p-tolyloxazol-4-ylmethoxy)cyclohexyl]ethyl}cyclo-pentanecarboxylic acid tert-Butyl 1-{2-[cis-3-(tert-butyldiphenylsilanyloxy)cyclohexyl]ethyl}cyclo-pent-3-enecarboxylate

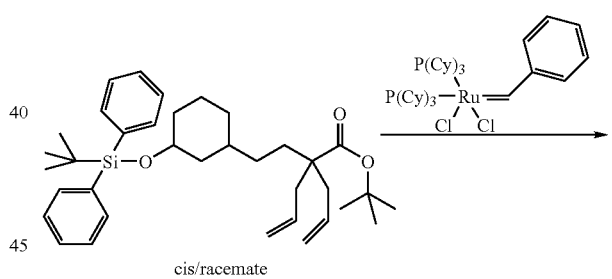

cis/racemate

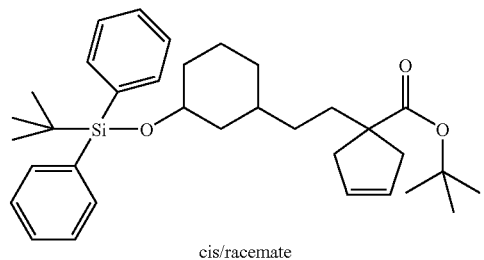

cis/racemate 2 g of tert-butyl 2-allyl-2-{2-[cis-3-(tert-butyldiphenylsilanyloxy)cyclohexyl]-ethyl}pent-4-enoate are dissolved in 100 ml of dichloromethane. For 5 minutes, argon is passed through the solution. 100 mg of Grubbs' catalyst are then added. The mixture is stirred at 40° C. for 2 hours. The solvent is then removed under reduced pressure and the residue is purified on silica gel using the mobile phase n-heptane:ethyl acetate=40:1. This gives 1.4 g of tert-butyl 1-{2-[cis-3-(tert-butyldiphenylsilanyloxy)cyclo-hexyl]ethyl}cyclopent-3-enecarboxylate as an oil. C34H48O3Si (532.85), $R_f$(n-heptane:ethyl acetate=20:1)=0.56.

Analogously to Example 77, tert-butyl 1-{2-[cis-3-(tert-butyldiphenylsilanyloxy)cyclohexyl]ethyl}cyclopent-3-enecarboxylate and 4-iodomethyl-5-methyl-2-(4-methylphenyl)oxazole gave 1-{2-[cis-3-(5-methyl-2-p-tolyloxazol-4-ylmethoxy)cyclohexyl]ethyl}cyclopentanecarboxylic acid.

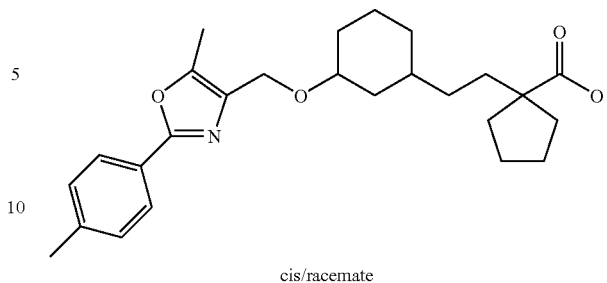

cis/racemate

C26H35NO4 (425.57), MS(ESI): 426 (M+H$^+$).

EXAMPLE 79

2-(4-Methoxyphenoxycarbonyl)-{2-[cis-3-(5-methyl-2-m-tolyloxazol-4-yl-methoxy)cyclohexyl]ethyl}amino)-3-methylbutyric acid

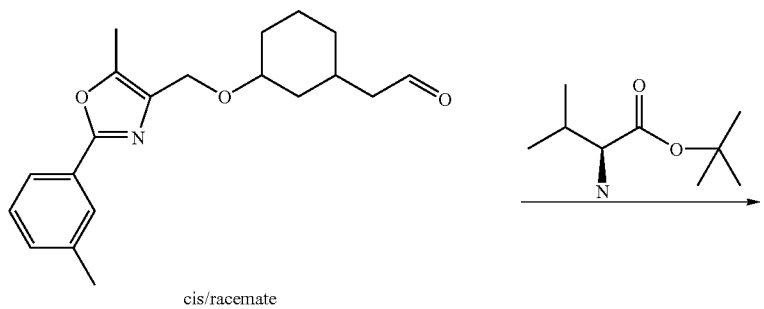

cis/racemate

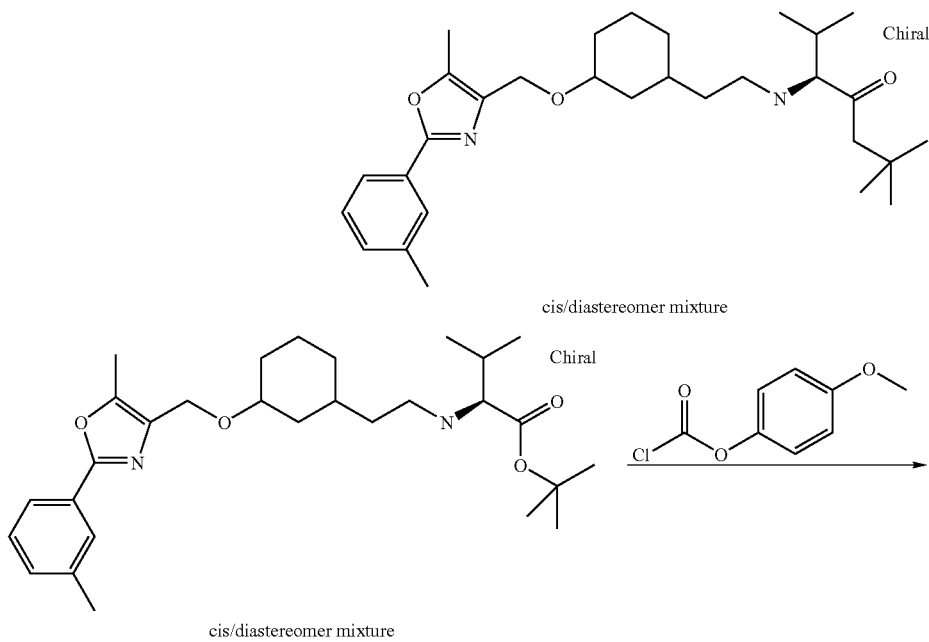

cis/diastereomer mixture cis/diastereomer mixture

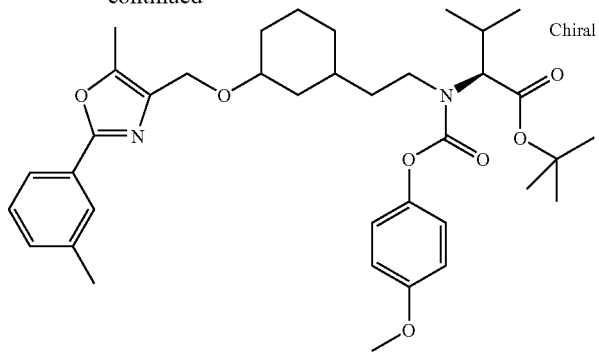
cis/diastereomer mixture
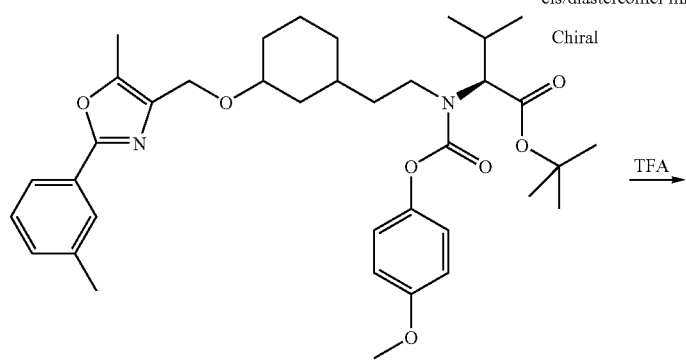
cis/diastereomer mixture
→ TFA
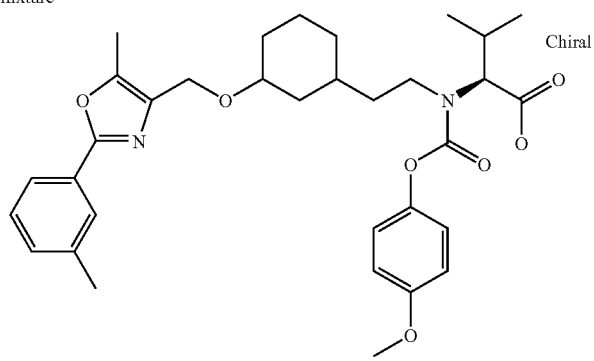
cis/diastereomer mixture
tert-Butyl (S)-3-methyl-2-{2-[cis-3-(5-methyl-2-m-tolyloxazol-4-ylmethoxy)-cyclohexyl]ethylamino}butyrate
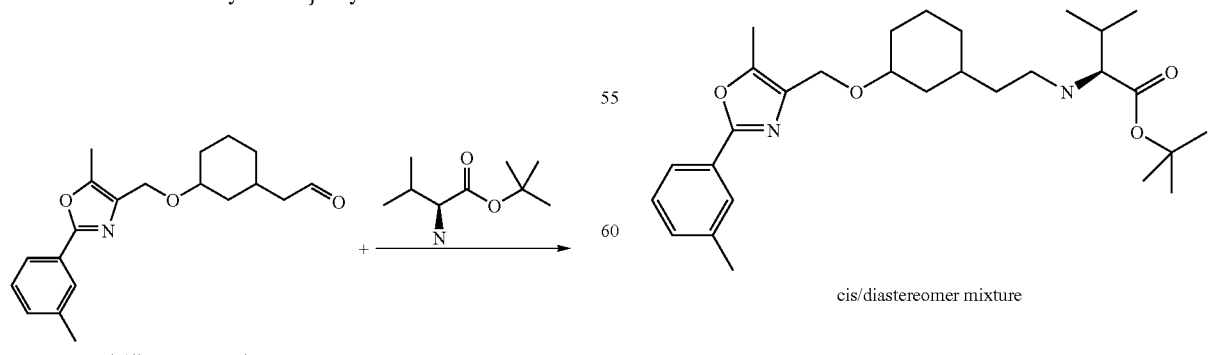
cis/diastereomer mixture
0.1 g of {cis-3-[2-(3-methylphenyl)-5-methyloxazol-4-ylmethoxy]cyclohexyl}-acetaldehyde (prepared according to process E4) is initially charged in methylene chloride, and a spatula tip of magnesium sulfate is added. 64 mg of amine are then added, the mixture is cooled to 0° C., 30 mg of sodium acetate are added and the mixture is stirred for 30 min. 84 mg of sodium triacetoxyborohydride are added, and the mixture is stirred at RT overnight. 8 ml of water are added to the reaction and the mixture is filtered through a kieselguhr cartridge, the cartridge is washed with 50 ml of methylene chloride and the solvent is removed under reduced pressure. This gives 0.13 g of tert-butyl (S)-3-methyl-2-{2-[cis-3-(5-methyl-2-m-tolyloxazol-4-yl-methoxy)cyclohexyl]ethylamino}butyrate. C29H44N2O4 (484), MS (ESI): 485 (M+H).

tert-Butyl (S)-2-((4-methoxyphenoxycarbonyl)-{2-[cis-3-(5-methyl-2-m-tolyl-oxazol-4-ylmethoxy)cyclohexyl]ethyl}amino)-3-methylbutyrate 130 mg of tert-butyl (S)-3-methyl-2-{2-[cis-3-(5-methyl-2-m-tolyloxazol-4-yl-methoxy)cyclohexyl]ethylamino}butyrate are dissolved in 1 ml of methylene chloride, 2 ml of a sat. sodium carbonate solution are added and the mixture is cooled to 0° C., an excess of the acid chloride is then added and the mixture is stirred at RT for 1 h. The entire reaction solution is applied to a kieselguhr cartridge and the cartridge is washed with 20 ml of methylene chloride. The solvent is removed under reduced pressure. This gives 0.1 g of tert-butyl (S)-2-((4-methoxyphenoxycarbonyl)-{2-[cis-3-(5-methyl-2-m-tolyloxazol-4-ylmethoxy)cyclohexyl]ethyl}amino)-3-methylbutyrate.

C37H50N2O7 (635), MS (ESI):636 (M+H)

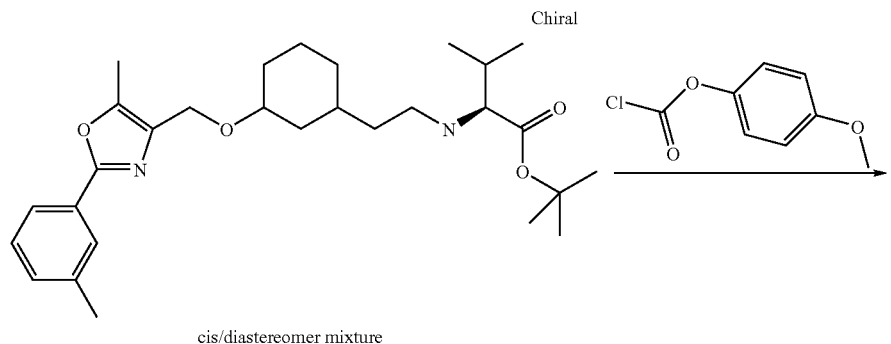

cis/diastereomer mixture

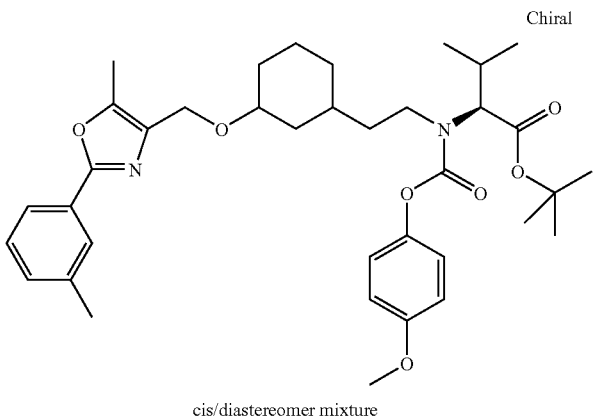

cis/diastereomer mixture (S)-2-((4-Methoxyphenoxycarbonyl)-{2-[cis-3-(5-methyl-2-m-tolyloxazol-4-ylmethoxy)cyclohexyl]ethyl}amino)-3-methylbutyric Acid

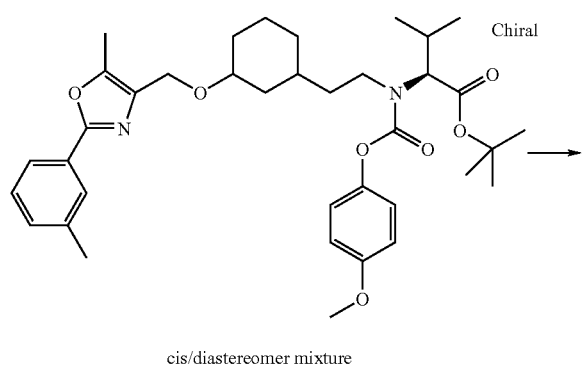

cis/diastereomer mixture cis/diastereomer mixture 0.10 g of tert-butyl (S)-2-((4-methoxyphenoxycarbonyl)-{2-[cis-3-(5-methyl-2-m-tolyloxazol-4-ylmethoxy)cyclohexyl]ethyl}amino)-3-methylbutyrate are dissolved in 2 ml of dichloromethane, and the solution is stirred with 1 ml of trichloroacetic acid at RT overnight. The solvent is then removed completely and the residue is purified by preparative HPLC. This gives 15.6 mg of (S)-2-((4-methoxyphenoxycarbonyl)-{2-[cis-3-(5-methyl-2-m-tolyloxazol-4-ylmethoxy)cyclohexyl]ethyl}amino)-3-methylbutyric acid.

C33H42N2O7 (579), MS (ESI): 580 (M+H)

EXAMPLE 80

Analogously to Example 79, [cis-3-(5-methyl-2-m-tolyloxazol-4-ylmethoxy)-cyclohexyl]acetaldehyde and methyl 1-aminocyclopentanecarboxylate gave 1-(benzyloxycarbonyl-{2-[cis-3-(5-methyl-2-m-tolyloxazol-4-ylmethoxy)-cyclohexyl]ethyl}amino)cyclopentanecarboxylic acid.

cis/racemate

C34H42N2O6 (574.7), MS(ESI): 575 (M+H)

EXAMPLE 81

Analogously to Example 79, cis-3-(5-methyl-2-m-tolyloxazol-4-ylmethoxy)-cyclohexyl]acetaldehyde and methyl 1-aminocyclopentanecarboxylate gave 1-((4-methoxybenzyloxycarbonyl)-{2-[cis-3-(5-methyl-2-m-tolyloxazol-4-ylmethoxy)cyclohexyl]ethyl}amino)cyclopentanecarboxylic acid.

cis/racemate

C35H44N2O7 (604.7), MS(ESI): 605 (M+H)

EXAMPLE 82

Analogously to Example 79, cis-3-(5-methyl-2-m-tolyloxazol-4-ylmethoxy)-cyclohexyl]acetaldehyde and methyl (S)-2-amino-2-methyl-3-phenyl-propionate gave (R)-2-((4- methoxybenzyloxycarbonyl)-{2-[cis-3-(5-methyl-2-m-tolyloxazol-4-ylmethoxy)cyclohexyl]ethyl}amino)-2-methyl-3-phenylpropionic acid.

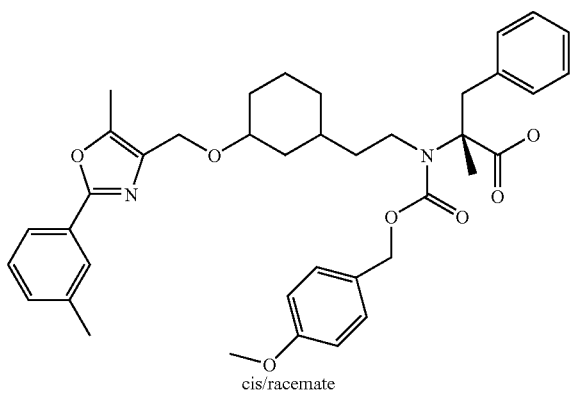

cis/racemate

C39H46N2O7 (654.8), MS(ESI): 656 (M+H)

EXAMPLE 83

Analogously to Example 79, cis-3-(5-methyl-2-m-tolyloxazol-4-ylmethoxy)-cyclohexyl]acetaldehyde and methyl (S)-2-amino-2-methyl-3-phenylpropionate gave (benzyloxycarbonyl-{2-[cis-3-(5-methyl-2-m-tolyl-oxazol-4-ylmethoxy)cyclohexyl]ethyl}amino)acetic acid.

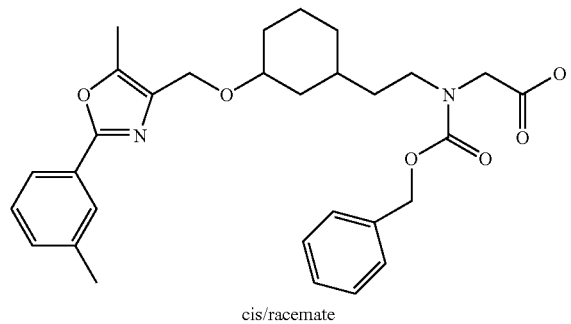

cis/racemate

C30H36N2O7 (520.6), MS(ESI): 521 (M+H)

EXAMPLE 84

Analogously to Example 79, cis-3-(5-methyl-2-m-tolyloxazol-4-ylmethoxy)-cyclohexyl]acetaldehyde and methyl (S)-2-amino-2-methyl-3-phenyl-propionate gave ({2-[cis-3-(5-methyl-2-m-tolyloxazol-4-ylmethoxy)-cyclohexyl]ethyl}phenylacetylamino)acetic acid.

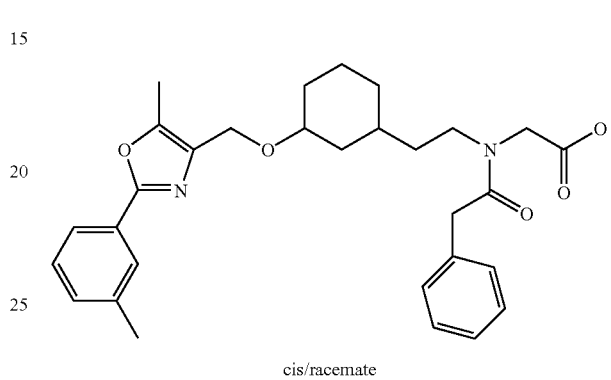

cis/racemate

C30H36N2O5 (504.6), MS(ESI): 505 (M+H)

EXAMPLE 85

Analogously to Example 79, cis-3-(5-methyl-2-m-tolyloxazol-4-ylmethoxy)-cyclohexyl]acetaldehyde and methyl (S)-2-amino-2-methyl-3-phenyl-propionate gave (1-{2-[cis-3-(5-methyl-2-m-tolyloxazol-4-ylmethoxy)-cyclohexyl]ethyl}-3-phenylureido)acetic acid.

---

What is claimed is:

1. A compound having the formula I:

in which:

Ring A is a $(C_3-C_8)$-cycloalkanediyl ring or a $(C_3-C_8)$-cycloalkenediyl ring, R1 and R2 are:
(a) Independently of one another H, F, Cl, Br, $CF_3$, $OCF_3$, $(C_1-C_6)$-alkyl, O—$(C_1-C_6)$-alkyl, $SCF_3$, $SF_5$, $OCF_2$—$CHF_2$, $(C_6-C_{10})$-aryl, $(C_6-C_{10})$-aryloxy, OH, $NO_2$; or
(b) together with the phenyl, ring form fused, partially or unsaturated bicyclic $(C_6-C_{10})$-aryl;

R3 is:
H, $(C_1-C_6)$-alkyl, $(C_3-C_8)$-cycloalkyl, $(C_1-C_3)$-alkyl-$(C_3-C_8)$-cycloalkyl, phenyl, $(C_1-C_3)$-alkyl-phenyl, $(C_5-C_6)$-heteroaryl, $(C_1-C_3)$-alkyl-$(C_5-C_6)$-heteroaryl, or $(C_1-C_3)$-alkyl fully or partially substituted by F;

W is:
(a) CH and o=1, or

X is $(C_1-C_6)$-alkanediyl, wherein one or more carbon atoms of the $(C_1-C_6)$ alkanediyl may be replaced by oxygen atoms;

Y1 is $(CR13R14)_p$, wherein p is 1 or 2;

Y2 is CH2, O, S, SO, $SO_2$ or NR9;

n is 0-2;

R4 is H, (C1-C6)-alkyl; F if Y2 is not O; NR9;

R5 is H, $(C_1-C_6)$-alkyl; F if Y2 is not O; NR9;

R6 is H, $(C_1-C_6)$-alkyl; or F if n is not 0;

R7 is:
H, F (if n is not 0), $(C_1-C_6)$-alkoxy, $(C_2-C_6)$-alkenyl, $(C_2-C_6)$-alkynyl, $(C_3-C_8)$-cycloalkyl, $(C_1-C_6)$-alkyl that may be unsubstituted or substituted by one or more radicals selected from the group consisting of: hydroxyl, phenyl, $(C_5-C_{11})$-heteroaryl, $(C_1-C_6)$-alkoxy and NR11R12, or phenyl that may be unsubstituted or substituted by one or more radicals from the group consisting of hydroxy, $(C_1-C_6)$-alkoxy, F and $CF_3$,
with the proviso that R7 is not NR11R12 or $(C_1-C_6)$-alkoxy if R6=F;

R6 and R7 are together with the carbon atom that carries them $(C_3-C_8)$-cycloalkyl;

R8 is H or $(C_1-C_6)$-alkyl;

R9 is:
H, $(C_1-C_6)$-alkyl, $(C_2-C_6)$-alkenyl, $(C_2-C_6)$-alkynyl, aryl-$(C_1-C_4)$-alkyl, CO—$(C_1-C_6)$-alkyl, CO—$(C_6-C_{10})$-aryl, CO—$(C_1-C_6)$-alkyl-$(C_6-C_{10})$-aryl, CO—$(C_5-C_{11})$-heteroaryl, C(O)—O—$(C_1-C_6)$-alkyl, C(O)—O—$(C_1-C_6)$-alkyl-$(C_6-C_{10})$-aryl, C(O)—O—$(C_6-C_{10})$-aryl, C(O)—O—$(C_5-C_{11})$-heteroaryl, $SO_2$—$(C_1-C_6)$-alkyl, $SO_2$—$(C_1-C_6)$-alkyl-$(C_6-C_{10})$-aryl, $SO_2$—$(C_1-C_6)$-alkyl-$SO_2$—$(C_1-C_6)$-alkyl, $SO_2$—$(C_6-C_{10})$-aryl, $SO_2$—$(C_5-C_{11})$-heteroaryl, wherein aryl or heteroaryl, or both may be unsubstituted or substituted by $(C_1-C_6)$-alkyl, O—$(C_1-C_6)$-alkyl, F, Cl, CO—$(C_1-C_6)$-alkyl;

R10 is H, $(C_1-C_6)$-alkyl or $(C_1-C_6)$-alkyl-phenyl;

R11 is H, $(C_1-C_6)$-alkyl or $(C_1-C_6)$-alkyl-phenyl;

R12 is H, $(C_1-C_6)$-alkyl or $(C_1-C_6)$-alkyl-phenyl;

R13 is H or $(C_1-C_6)$-alkyl; and

R14 is H or $(C_1-C_6)$-alkyl; or a physiologically acceptable salt of the compound;
a solvate of the compound; or
a physiologically active derivative of the compound.

2. The compound of claim 1 in which

Ring A is $(C_3-C_8)$-cycloalkanediyl or $(C_3-C_8)$-cycloalkenediyl, wherein one carbon atom of the $(C_3-C_8)$-cycloalkanediyl ring or the $(C_3-C_8)$ cycloalkenediyl ring may be replaced by an oxygen atom; and X is $(C_1-C_6)$-alkanediyl, wherein the $C_1$ or $C_2$ carbon atom (to Ring A) may be replaced by an oxygen atom.

3. The compound of claim 1, in which

Ring A is cis-cyclohexane-1,3-diyl;

R1 and R2 are:
independently of one another H, F, $CF_3$, $(C_1-C_6)$-alkyl, O—$(C_1-C_6)$-alkyl, or phenyl; or
together with a phenyl ring of the compound form a naphthyl;

R3 is $(C_1-C_6)$-alkyl, $(C_3-C_8)$-cycloalkyl, or phenyl;

W is:
CH if o=1, or
O or S if o=0;

X is $CH_2$—O or $CH_2$—O—$CH_2$;

Y1 is $CH_2$;

Y2 is $CH_2$, O, S, SO, $SO_2$ or NR9;

n is 0;

R4 is H;

R5 is H;

R6 is H, $(C_1-C_6)$-alkyl, or benzyl;

R7 is H, $(C_1-C_6)$-alkyl, $(C_3-C_6)$-cycloalkyl, phenyl, or benzyl,

R6 and R7 together with the carbon atom that carries them are $(C_3-C_6)$-cycloalkyl;

R8 is H; and

R9 is:
H, or
$(C_1-C_6)$-alkyl, which may be unsubstituted or substituted by:
$(C_3-C_6)$-cycloalkyl, phenyl; CO—$(C_1-C_6)$-alkyl, CO—$(C_1-C_6)$-alkyl-phenyl, CO-phenyl, C(O)—O—$(C_1-C_6)$-alkyl, CO—NH-phenyl, $SO_2$—$(C_1$-

$C_4$)-alkyl, $SO_2$—($C_1$-$C_4$)-alkyl-$SO_2$—($C_1$-$C_4$)-alkyl, $SO_2$-tolyl, or a combination thereof, wherein the phenyl of the substituent for its part may be substituted by O—($C_1$-$C_3$)-alkyl;

a physiologically acceptable salt of the compound;

a solvate of the compound; or a physiologically acceptable derivative of the compound.

4. A pharmaceutical composition comprising the compound of claim 1 and a pharmaceutically acceptable carrier.

5. The pharmaceutical composition of claim 4, further comprising an antidiabetic.

6. The pharmaceutical composition of claim 4, further comprising a lipid modulator.

7. The compound of claim 2, in which

Ring A is cis-cyclohexane-1,3-diyl;

R1 and R2 are:

independently of one another H, F, $CF_3$, ($C_1$-$C_6$)-alkyl, O—($C_1$-$C_6$)-alkyl, or phenyl; or together with a phenyl ring of the compound form a naphthyl;

R3 is ($C_1$-$C_6$)-alkyl, ($C_3$-$C_8$)-cycloalkyl, or phenyl;

W is:

CH if o=1, or

O or S if o=0;

X is $CH_2$—O or $CH_2$—O—$CH_2$;

Y1 is $CH_2$;

Y2 is $CH_2$, O, S, SO, $SO_2$ or NR9;

n is 0;

R4 is H;

R5 is H;

R6 is H, ($C_1$-$C_6$)-alkyl, or benzyl;

R7 is H, ($C_1$-$C_6$)-alkyl, ($C_3$-$C_6$)-cycloalkyl, phenyl, or benzyl,

R6 and R7 together with the carbon atom that carries them are ($C_3$-$C_6$)-cycloalkyl;

R8 is H; and

R9 is:

H, or ($C_1$-$C_6$)-alkyl, which may be unsubstituted or substituted by:

($C_3$-$C_6$)-cycloalkyl, phenyl; CO—($C_1$-$C_6$)-alkyl, CO—($C_1$-$C_6$)-alkyl-phenyl, CO-phenyl, C(O)—O—($C_1$-$C_6$)-alkyl, CO—NH-phenyl, $SO_2$—($C_1$-$C_4$)-alkyl, $SO_2$—($C_1$-$C_4$)-alkyl-$SO_2$—($C_1$-$C_4$)-alkyl, $SO_2$-tolyl, or a combination thereof, wherein the phenyl of the substituent for its part may be substituted by O—($C_1$-$C_3$)-alkyl;

a physiologically acceptable salt of the compound;

a solvate of the compound; or a physiologically acceptable derivative of the compound.

8. A pharmaceutical composition comprising the compound of claim 2 and a pharmaceutically acceptable carrier.

9. A pharmaceutical composition comprising the compound of claim 3 and a pharmaceutically acceptable carrier.

10. A pharmaceutical composition comprising the compound of claim 7 and a pharmaceutically acceptable carrier.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 1
cggagtactg tcctccgag                    19

<210> SEQ ID NO 2
<211> LENGTH: 19

```
<212> TYPE: DNA
<213> ORGANISM: Artificial
<220> FEATURE:
<223> OTHER INFORMATION: Binding Site of Yeast Transcription Factor GAL4

<400> SEQUENCE: 2
ctcggaggac agtactccg                                              19
```